(12) United States Patent
Nekoomaram et al.

(10) Patent No.: US 10,429,250 B2
(45) Date of Patent: Oct. 1, 2019

(54) ANALYTE MONITORING SYSTEM AND METHODS FOR MANAGING POWER AND NOISE

(71) Applicant: Abbott Diabetes Care Inc., Alameda, CA (US)

(72) Inventors: Saeed Nekoomaram, San Mateo, CA (US); Martin J. Fennell, Concord, CA (US); Mark Kent Sloan, Redwood City, CA (US); Lei He, Moraga, CA (US); Jeffery Mario Sicurello, Union City, CA (US)

(73) Assignee: Abbott Diabetes Care, Inc., Alameda, CA (US)

( * ) Notice: Subject to any disclaimer, the term of this patent is extended or adjusted under 35 U.S.C. 154(b) by 0 days.

(21) Appl. No.: 14/669,842

(22) Filed: Mar. 26, 2015

(65) Prior Publication Data
US 2015/0198488 A1    Jul. 16, 2015

Related U.S. Application Data

(62) Division of application No. 12/873,298, filed on Aug. 31, 2010, now Pat. No. 8,993,331.
(Continued)

(51) Int. Cl.
*G01K 13/00* (2006.01)
*A61B 5/00* (2006.01)
(Continued)

(52) U.S. Cl.
CPC ............ *G01K 13/00* (2013.01); *A61B 5/0002* (2013.01); *A61B 5/14532* (2013.01); *G01K 1/02* (2013.01);
(Continued)

(58) Field of Classification Search
CPC ........ G01K 13/00; G01K 1/02; A61B 5/0002; A61B 5/14532; A61B 2560/0209; Y10T 436/12
See application file for complete search history.

(56) References Cited

U.S. PATENT DOCUMENTS 2,755,036 A    7/1956  Mikko
3,260,656 A    7/1966  Ross, Jr.
(Continued)

FOREIGN PATENT DOCUMENTS

CA    2396613    3/2008
DE    4234553    1/1995
(Continued)

OTHER PUBLICATIONS

Abruna, H. D., et al., "Rectifying Interfaces Using Two-Layer Films of Electrochemically Polymerized Vinylpyridine and Vinylbipyridine Complexes of Ruthenium and Iron on Electrodes", *Journal of the American Chemical Society*, vol. 103, No. 1, 1981, pp. 1-5.
(Continued)

*Primary Examiner* — Samuel P Siefke
(74) *Attorney, Agent, or Firm* — Vorys, Sater, Seymour and Pease LLP

(57) ABSTRACT

Disclosed herein are methods and systems for conserving energy of a power source of an analyte monitoring device. Also disclosed herein are methods and systems for reducing noise during data transmissions to and from the analyte monitoring device.

16 Claims, 9 Drawing Sheets

Related U.S. Application Data

(60) Provisional application No. 61/238,557, filed on Aug. 31, 2009, provisional application No. 61/247,537, filed on Sep. 30, 2009.

(51) Int. Cl.
*A61B 5/145* (2006.01)
*G01K 1/02* (2006.01)

(52) U.S. Cl.
CPC ..... *A61B 2560/0209* (2013.01); *Y10T 436/12* (2015.01)

(56) References Cited

U.S. PATENT DOCUMENTS

| | | |
|---|---|---|
| 3,304,413 A | 2/1967 | Lehmann et al. |
| 3,581,062 A | 5/1971 | Aston |
| 3,651,318 A | 3/1972 | Czekajewski |
| 3,653,841 A | 4/1972 | Klein |
| 3,698,386 A | 10/1972 | Fried |
| 3,719,564 A | 3/1973 | Lilly, Jr. et al. |
| 3,768,014 A | 10/1973 | Smith et al. |
| 3,776,832 A | 12/1973 | Oswin et al. |
| 3,837,339 A | 9/1974 | Aisenberg et al. |
| 3,919,051 A | 11/1975 | Koch et al. |
| 3,926,760 A | 12/1975 | Allen et al. |
| 3,949,388 A | 4/1976 | Fuller |
| 3,972,320 A | 8/1976 | Kalman |
| 3,979,274 A | 9/1976 | Newman |
| 4,003,379 A | 1/1977 | Ellinwood, Jr. |
| 4,008,717 A | 2/1977 | Kowarski |
| 4,016,866 A | 4/1977 | Lawton |
| 4,021,718 A | 5/1977 | Konrad |
| 4,031,449 A | 6/1977 | Trombly |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,129,128 A | 12/1978 | McFarlane |
| 4,151,845 A | 5/1979 | Clemens |
| 4,154,231 A | 5/1979 | Russell |
| 4,168,205 A | 9/1979 | Danniger et al. |
| 4,172,770 A | 10/1979 | Semersky et al. |
| 4,178,916 A | 12/1979 | McNamara |
| 4,193,026 A | 3/1980 | Finger et al. |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,245,634 A | 1/1981 | Albisser et al. |
| 4,247,297 A | 1/1981 | Berti et al. |
| 4,271,449 A | 6/1981 | Grogan |
| 4,318,784 A | 3/1982 | Higgins et al. |
| 4,327,725 A | 5/1982 | Cortese et al. |
| 4,331,869 A | 5/1982 | Rollo |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,375,399 A | 3/1983 | Havas et al. |
| 4,384,586 A | 5/1983 | Christiansen |
| 4,390,621 A | 6/1983 | Bauer |
| 4,392,933 A | 7/1983 | Nakamura et al. |
| 4,401,122 A | 8/1983 | Clark, Jr. |
| 4,404,066 A | 9/1983 | Johnson |
| 4,407,959 A | 10/1983 | Tsuji et al. |
| 4,417,588 A | 11/1983 | Houghton et al. |
| 4,418,148 A | 11/1983 | Oberhardt |
| 4,420,564 A | 12/1983 | Tsuji et al. |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,441,968 A | 4/1984 | Emmer et al. |
| 4,444,892 A | 4/1984 | Malmros |
| 4,445,090 A | 4/1984 | Melocik et al. |
| 4,450,842 A | 5/1984 | Zick et al. |
| 4,458,686 A | 7/1984 | Clark, Jr. |
| 4,461,691 A | 7/1984 | Frank |
| 4,464,170 A | 8/1984 | Clemens et al. |
| 4,467,811 A | 8/1984 | Clark, Jr. |
| 4,469,110 A | 9/1984 | Slama |
| 4,475,901 A | 10/1984 | Kraegen et al. |
| 4,477,314 A | 10/1984 | Richter et al. |
| 4,478,976 A | 10/1984 | Goertz et al. |
| 4,483,924 A | 11/1984 | Tsuji et al. |
| 4,484,987 A | 11/1984 | Gough |
| 4,494,950 A | 1/1985 | Fischell |
| 4,509,531 A | 4/1985 | Ward |
| 4,512,348 A | 4/1985 | Uchigaki et al. |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,569,589 A | 2/1986 | Neufeld |
| 4,571,292 A | 2/1986 | Liu et al. |
| 4,573,994 A | 3/1986 | Fischell et al. |
| 4,581,336 A | 4/1986 | Malloy et al. |
| 4,583,035 A | 4/1986 | Sloan |
| 4,595,011 A | 6/1986 | Phillips |
| 4,595,479 A | 6/1986 | Kimura et al. |
| 4,601,707 A | 7/1986 | Albisser et al. |
| 4,619,754 A | 10/1986 | Niki et al. |
| 4,619,793 A | 10/1986 | Lee |
| 4,627,445 A | 12/1986 | Garcia et al. |
| 4,627,908 A | 12/1986 | Miller |
| 4,633,878 A | 1/1987 | Bombardien |
| 4,633,881 A | 1/1987 | Moore et al. |
| 4,637,403 A | 1/1987 | Garcia et al. |
| 4,648,408 A | 3/1987 | Hutcheson et al. |
| 4,650,547 A | 3/1987 | Gough |
| 4,653,513 A | 3/1987 | Dombrowski |
| 4,654,197 A | 3/1987 | Lilja et al. |
| 4,655,880 A | 4/1987 | Liu |
| 4,655,885 A | 4/1987 | Hill et al. |
| 4,658,463 A | 4/1987 | Sugita et al. |
| 4,671,288 A | 6/1987 | Gough |
| 4,674,652 A | 6/1987 | Aten et al. |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,903 A | 8/1987 | Cable et al. |
| 4,686,624 A | 8/1987 | Blum et al. |
| 4,703,324 A | 10/1987 | White |
| 4,703,756 A | 11/1987 | Gough et al. |
| 4,711,245 A | 12/1987 | Higgins et al. |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,731,726 A | 3/1988 | Allen, III |
| 4,749,985 A | 6/1988 | Corsberg |
| 4,750,496 A | 6/1988 | Reinhardt |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |

(56) References Cited

U.S. PATENT DOCUMENTS

| | | |
|---|---|---|
| 4,776,944 A | 10/1988 | Janata et al. |
| 4,777,953 A | 10/1988 | Ash et al. |
| 4,779,618 A | 10/1988 | Mund et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,803,625 A | 2/1989 | Fu et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| 4,835,372 A | 5/1989 | Gombrich et al. |
| RE32,947 E | 6/1989 | Dormer et al. |
| 4,837,049 A | 6/1989 | Byers et al. |
| 4,840,893 A | 6/1989 | Hill et al. |
| RE32,974 E | 7/1989 | Porat et al. |
| 4,844,076 A | 7/1989 | Lesho et al. |
| 4,845,035 A | 7/1989 | Fanta et al. |
| 4,847,785 A | 7/1989 | Stephens |
| 4,848,351 A | 7/1989 | Finch |
| 4,854,322 A | 8/1989 | Ash et al. |
| 4,856,340 A | 8/1989 | Garrison |
| 4,857,713 A | 8/1989 | Brown |
| 4,858,617 A | 8/1989 | Sanders |
| 4,870,561 A | 9/1989 | Love et al. |
| 4,871,351 A | 10/1989 | Feingold |
| 4,871,440 A | 10/1989 | Nagata et al. |
| 4,874,499 A | 10/1989 | Smith et al. |
| 4,874,500 A | 10/1989 | Madou et al. |
| 4,890,620 A | 1/1990 | Gough |
| 4,890,621 A | 1/1990 | Hakky |
| 4,894,137 A | 1/1990 | Takizawa et al. |
| 4,897,162 A | 1/1990 | Lewandowski et al. |
| 4,897,173 A | 1/1990 | Nankai et al. |
| 4,899,839 A | 2/1990 | Dessertine et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,920,969 A | 5/1990 | Suzuki |
| 4,920,977 A | 5/1990 | Haynes |
| 4,923,586 A | 5/1990 | Katayama et al. |
| 4,925,268 A | 5/1990 | Iyer et al. |
| 4,927,516 A | 5/1990 | Yamaguchi et al. |
| 4,931,795 A | 6/1990 | Gord |
| 4,934,369 A | 6/1990 | Maxwell |
| 4,935,105 A | 6/1990 | Churchouse |
| 4,935,345 A | 6/1990 | Guibeau et al. |
| 4,936,956 A | 6/1990 | Wrighton |
| 4,938,860 A | 7/1990 | Wogoman |
| 4,942,127 A | 7/1990 | Wada et al. |
| 4,944,299 A | 7/1990 | Silvian |
| 4,945,045 A | 7/1990 | Forrest et al. |
| 4,950,378 A | 8/1990 | Nagata |
| 4,953,552 A | 9/1990 | DeMarzo |
| 4,954,129 A | 9/1990 | Giuliani et al. |
| 4,957,115 A | 9/1990 | Selker |
| 4,958,632 A | 9/1990 | Duggan |
| 4,968,400 A | 11/1990 | Shimomura et al. |
| 4,969,468 A | 11/1990 | Byers et al. |
| 4,970,145 A | 11/1990 | Bennetto et al. |
| 4,974,929 A | 12/1990 | Curry |
| 4,979,509 A | 12/1990 | Hakky |
| 4,986,271 A | 1/1991 | Wilkins |
| 4,990,845 A | 2/1991 | Gord |
| 4,991,582 A | 2/1991 | Byers et al. |
| 4,994,068 A | 2/1991 | Hufnagie |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,002,054 A | 3/1991 | Ash et al. |
| 5,007,427 A | 4/1991 | Suzuki et al. |
| 5,016,172 A | 5/1991 | Dessertine |
| 5,016,201 A | 5/1991 | Bryan et al. |
| 5,019,974 A | 5/1991 | Beckers |
| 5,034,192 A | 7/1991 | Wrighton et al. |
| 5,035,860 A | 7/1991 | Kleingeld et al. |
| 5,036,860 A | 8/1991 | Leigh et al. |
| 5,036,861 A | 8/1991 | Sembrowich et al. |
| 5,037,527 A | 8/1991 | Hayashi et al. |
| 5,049,487 A | 9/1991 | Phillips et al. |
| 5,050,612 A | 9/1991 | Matsumura |
| 5,051,688 A | 9/1991 | Murase et al. |
| 5,055,171 A | 10/1991 | Peck |
| 5,058,592 A | 10/1991 | Whisler |
| 5,061,941 A | 10/1991 | Lizzi et al. |
| 5,063,081 A | 11/1991 | Cozzette et al. |
| 5,068,536 A | 11/1991 | Rosenthal |
| 5,070,535 A | 12/1991 | Hochmair et al. |
| 5,073,500 A | 12/1991 | Saito et al. |
| 5,077,476 A | 12/1991 | Rosenthal |
| 5,078,854 A | 1/1992 | Burgess et al. |
| 5,082,550 A | 1/1992 | Rishpon et al. |
| 5,082,786 A | 1/1992 | Nakamoto |
| 5,084,828 A | 1/1992 | Kaufman et al. |
| 5,089,112 A | 2/1992 | Skotheim et al. |
| 5,094,951 A | 3/1992 | Rosenberg |
| 5,095,904 A | 3/1992 | Seligman et al. |
| 5,096,560 A | 3/1992 | Takai et al. |
| 5,096,836 A | 3/1992 | Macho et al. |
| 5,097,834 A | 3/1992 | Skrabal |
| 5,101,814 A | 4/1992 | Palti |
| 5,106,365 A | 4/1992 | Hernandez |
| 5,108,564 A | 4/1992 | Szuminsky et al. |
| 5,109,850 A | 5/1992 | Blanco et al. |
| 5,111,539 A | 5/1992 | Hiruta et al. |
| 5,111,818 A | 5/1992 | Suzuji et al. |
| 5,112,455 A | 5/1992 | Cozzette et al. |
| 5,114,678 A | 5/1992 | Crawford et al. |
| 5,120,420 A | 6/1992 | Nankai et al. |
| 5,120,421 A | 6/1992 | Glass et al. |
| 5,122,925 A | 6/1992 | Inpyn |
| 5,124,661 A | 6/1992 | Zellin et al. |
| 5,126,034 A | 6/1992 | Carter et al. |
| 5,126,247 A | 6/1992 | Palmer et al. |
| 5,130,009 A | 7/1992 | Marsoner et al. |
| 5,133,856 A | 7/1992 | Yamaguchi et al. |
| 5,134,391 A | 7/1992 | Okada |
| 5,135,003 A | 8/1992 | Souma |
| 5,135,004 A | 8/1992 | Adams et al. |
| 5,139,023 A | 8/1992 | Stanley et al. |
| 5,140,393 A | 8/1992 | Hijikihgawa et al. |
| 5,141,868 A | 8/1992 | Shanks et al. |
| 5,161,532 A | 11/1992 | Joseph |
| 5,165,407 A | 11/1992 | Wilson et al. |
| 5,168,046 A | 12/1992 | Hamamoto et al. |
| 5,174,291 A | 12/1992 | Schoonen et al. |
| 5,176,644 A | 1/1993 | Srisathapat et al. |
| 5,176,662 A | 1/1993 | Bartholomew et al. |
| 5,182,707 A | 1/1993 | Cooper et al. |
| 5,184,359 A | 2/1993 | Tsukamura et al. |
| 5,185,256 A | 2/1993 | Nankai et al. |
| 5,190,041 A | 3/1993 | Palti |
| 5,192,415 A | 3/1993 | Yoshioka et al. |
| 5,192,416 A | 3/1993 | Wang et al. |
| 5,193,539 A | 3/1993 | Schulman et al. |
| 5,193,540 A | 3/1993 | Schulman et al. |
| 5,197,322 A | 3/1993 | Indravudh |
| 5,198,367 A | 3/1993 | Aizawa et al. |
| 5,200,051 A | 4/1993 | Cozzette et al. |
| 5,202,261 A | 4/1993 | Musho et al. |
| 5,205,920 A | 4/1993 | Oyama et al. |
| 5,206,145 A | 4/1993 | Cattell |
| 5,208,154 A | 5/1993 | Weaver et al. |
| 5,209,229 A | 5/1993 | Gilli |
| 5,215,887 A | 6/1993 | Saito |
| 5,216,597 A | 6/1993 | Beckers |
| 5,217,442 A | 6/1993 | Davis |

(56) References Cited

U.S. PATENT DOCUMENTS

| | | |
|---|---|---|
| 5,217,595 A | 6/1993 | Smith et al. |
| 5,227,042 A | 7/1993 | Zawodzinski et al. |
| 5,229,282 A | 7/1993 | Yoshioka et al. |
| 5,236,143 A | 8/1993 | Dragon |
| 5,237,993 A | 8/1993 | Skrabal |
| 5,245,314 A | 9/1993 | Kah et al. |
| 5,246,867 A | 9/1993 | Lakowicz et al. |
| 5,250,439 A | 10/1993 | Musho et al. |
| 5,251,126 A | 10/1993 | Kahn et al. |
| 5,257,971 A | 11/1993 | Lord et al. |
| 5,257,980 A | 11/1993 | Van Antwerp et al. |
| 5,261,401 A | 11/1993 | Baker et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,265,888 A | 11/1993 | Yamamoto et al. |
| 5,266,179 A | 11/1993 | Nankai et al. |
| 5,269,212 A | 12/1993 | Peters et al. |
| 5,271,815 A | 12/1993 | Wong |
| 5,272,060 A | 12/1993 | Hamamoto et al. |
| 5,275,159 A | 1/1994 | Griebel |
| 5,278,079 A | 1/1994 | Gubinski et al. |
| 5,279,294 A | 1/1994 | Anderson et al. |
| 5,282,950 A | 2/1994 | Dietze et al. |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,289,497 A | 2/1994 | Jackobson et al. |
| 5,291,887 A | 3/1994 | Stanley et al. |
| 5,293,546 A | 3/1994 | Tadros et al. |
| 5,293,877 A | 3/1994 | O'Hara et al. |
| 5,299,571 A | 4/1994 | Mastrototaro |
| 5,304,468 A | 4/1994 | Phillips et al. |
| 5,307,263 A | 4/1994 | Brown |
| 5,309,919 A | 5/1994 | Snell et al. |
| 5,310,885 A | 5/1994 | Maier et al. |
| 5,320,098 A | 6/1994 | Davidson |
| 5,320,725 A | 6/1994 | Gregg et al. |
| 5,322,063 A | 6/1994 | Allen et al. |
| 5,324,303 A | 6/1994 | Strong et al. |
| 5,324,316 A | 6/1994 | Schulman et al. |
| 5,326,449 A | 7/1994 | Cunningham |
| 5,333,615 A | 8/1994 | Craelius et al. |
| 5,337,258 A | 8/1994 | Dennis |
| 5,337,747 A | 8/1994 | Neftei |
| 5,340,722 A | 8/1994 | Wolfbeis et al. |
| 5,342,408 A | 8/1994 | deCoriolis et al. |
| 5,342,789 A | 8/1994 | Chick et al. |
| 5,352,348 A | 10/1994 | Young et al. |
| 5,356,348 A | 10/1994 | Bellio et al. |
| 5,356,786 A | 10/1994 | Heller et al. |
| 5,358,135 A | 10/1994 | Robbins et al. |
| 5,358,514 A | 10/1994 | Schulman et al. |
| 5,360,404 A | 11/1994 | Novacek et al. |
| 5,364,797 A | 11/1994 | Olson et al. |
| 5,366,609 A | 11/1994 | White et al. |
| 5,368,028 A | 11/1994 | Palti |
| 5,370,622 A | 12/1994 | Livingston et al. |
| 5,371,687 A | 12/1994 | Holmes, II et al. |
| 5,371,734 A | 12/1994 | Fischer |
| 5,371,787 A | 12/1994 | Hamilton |
| 5,372,133 A | 12/1994 | Hogen Esch |
| 5,372,427 A | 12/1994 | Padovani et al. |
| 5,376,070 A | 12/1994 | Purvis et al. |
| 5,376,251 A | 12/1994 | Kaneko et al. |
| 5,377,258 A | 12/1994 | Bro |
| 5,378,628 A | 1/1995 | Gratzel et al. |
| 5,379,238 A | 1/1995 | Stark |
| 5,379,764 A | 1/1995 | Barnes et al. |
| 5,380,422 A | 1/1995 | Negishis et al. |
| 5,382,346 A | 1/1995 | Uenoyama et al. |
| 5,387,327 A | 2/1995 | Khan |
| 5,390,671 A | 2/1995 | Lord et al. |
| 5,391,250 A | 2/1995 | Cheney, II et al. |
| 5,393,903 A | 2/1995 | Gratzel et al. |
| 5,395,504 A | 3/1995 | Saurer et al. |
| 5,399,823 A | 3/1995 | McCusker |
| 5,400,782 A | 3/1995 | Beaubiah |
| 5,400,794 A | 3/1995 | Gorman |
| 5,408,999 A | 4/1995 | Singh et al. |
| 5,410,326 A | 4/1995 | Goldstein |
| 5,410,471 A | 4/1995 | Alyfuku et al. |
| 5,410,474 A | 4/1995 | Fox |
| 5,411,647 A | 5/1995 | Johnson et al. |
| 5,413,690 A | 5/1995 | Kost et al. |
| 5,422,246 A | 6/1995 | Koopal et al. |
| 5,425,868 A | 6/1995 | Pedersen |
| 5,429,602 A | 7/1995 | Hauser |
| 5,431,160 A | 7/1995 | Wilkins |
| 5,431,691 A | 7/1995 | Snell et al. |
| 5,431,921 A | 7/1995 | Thombre |
| 5,433,710 A | 7/1995 | Van Antwerp et al. |
| 5,437,973 A | 8/1995 | Vadgama et al. |
| 5,437,999 A | 8/1995 | Dieboid et al. |
| 5,438,271 A | 8/1995 | White et al. |
| 5,438,983 A | 8/1995 | Falcone |
| 5,445,611 A | 8/1995 | Eppstein et al. |
| 5,445,920 A | 8/1995 | Saito |
| 5,456,692 A | 10/1995 | Smith, Jr. et al. |
| 5,456,940 A | 10/1995 | Funderburk |
| 5,458,140 A | 10/1995 | Eppstein et al. |
| 5,460,618 A | 10/1995 | Harreld |
| 5,462,051 A | 10/1995 | Oka et al. |
| 5,462,525 A | 10/1995 | Srisathapat et al. |
| 5,462,645 A | 10/1995 | Albery et al. |
| 5,466,218 A | 11/1995 | Srisathapat et al. |
| 5,467,778 A | 11/1995 | Catt et al. |
| 5,469,846 A | 11/1995 | Khan |
| 5,472,317 A | 12/1995 | Field et al. |
| 5,476,460 A | 12/1995 | Montalvo |
| 5,477,855 A | 12/1995 | Schindler et al. |
| 5,482,473 A | 1/1996 | Lord et al. |
| 5,484,404 A | 1/1996 | Schulman et al. |
| 5,487,751 A | 1/1996 | Radons et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,499,243 A | 3/1996 | Hall |
| 5,501,956 A | 3/1996 | Wada et al. |
| 5,505,709 A | 4/1996 | Funderburk |
| 5,505,713 A | 4/1996 | Van Antwerp et al. |
| 5,507,288 A | 4/1996 | Bocker et al. |
| 5,508,171 A | 4/1996 | Walling et al. |
| 5,509,410 A | 4/1996 | Hill et al. |
| 5,514,103 A | 5/1996 | Srisathapat et al. |
| 5,514,253 A | 5/1996 | Davis et al. |
| 5,514,718 A | 5/1996 | Lewis et al. |
| 5,518,006 A | 5/1996 | Mawhirt et al. |
| 5,520,787 A | 5/1996 | Hanagan et al. |
| 5,522,865 A | 6/1996 | Schulman et al. |
| 5,525,511 A | 6/1996 | D'Costa |
| 5,526,120 A | 6/1996 | Jina et al. |
| 5,527,307 A | 6/1996 | Srisathapat et al. |
| 5,529,676 A | 6/1996 | Maley et al. |
| 5,531,878 A | 7/1996 | Vadgama et al. |
| 5,532,686 A | 7/1996 | Urbas et al. |
| 5,538,511 A | 7/1996 | Van Antwerp et al. |
| 5,544,196 A | 8/1996 | Tiedmann, Jr. et al. |
| 5,545,152 A | 8/1996 | Funderburk et al. |
| 5,545,191 A | 8/1996 | Mann et al. |
| 5,549,113 A | 8/1996 | Halleck et al. |
| 5,549,115 A | 8/1996 | Morgan et al. |
| 5,552,027 A | 9/1996 | Birkle et al. |
| 5,554,166 A | 9/1996 | Lange et al. |
| 5,556,524 A | 9/1996 | Albers |
| 5,560,357 A | 10/1996 | Faupei et al. |
| 5,562,713 A | 10/1996 | Silvian |
| 5,565,085 A | 10/1996 | Ikeda et al. |

(56) References Cited

U.S. PATENT DOCUMENTS

| | | |
|---|---|---|
| 5,567,302 A | 10/1996 | Song et al. |
| 5,568,806 A | 10/1996 | Cheney, II et al. |
| 5,569,186 A | 10/1996 | Lord et al. |
| 5,569,212 A | 10/1996 | Brown |
| 5,573,647 A | 11/1996 | Maley et al. |
| 5,575,895 A | 11/1996 | Ikeda et al. |
| 5,580,527 A | 12/1996 | Bell et al. |
| 5,580,794 A | 12/1996 | Allen |
| 5,581,206 A | 12/1996 | Chevallier et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halili et al. |
| 5,589,326 A | 12/1996 | Deng et al. |
| 5,593,852 A | 1/1997 | Heller et al. |
| 5,594,906 A | 1/1997 | Holmes, II et al. |
| 5,596,150 A | 1/1997 | Arndy et al. |
| 5,596,994 A | 1/1997 | Bro |
| 5,600,301 A | 2/1997 | Robinson, III |
| 5,601,435 A | 2/1997 | Quy |
| 5,601,694 A | 2/1997 | Maley et al. |
| 5,605,152 A | 2/1997 | Slate et al. |
| 5,609,575 A | 3/1997 | Larson et al. |
| 5,611,900 A | 3/1997 | Worden et al. |
| 5,615,135 A | 3/1997 | Waclawsky et al. |
| 5,615,671 A | 4/1997 | Schoonen et al. |
| 5,616,222 A | 4/1997 | Maley et al. |
| 5,617,851 A | 4/1997 | Lipkovker |
| 5,623,925 A | 4/1997 | Swenson et al. |
| 5,623,933 A | 4/1997 | Amano et al. |
| 5,628,309 A | 5/1997 | Brown |
| 5,628,310 A | 5/1997 | Rao et al. |
| 5,628,324 A | 5/1997 | Sarbach |
| 5,628,890 A | 5/1997 | Carter et al. |
| 5,629,981 A | 5/1997 | Nerlikar |
| 5,634,468 A | 6/1997 | Platt et al. |
| 5,637,095 A | 6/1997 | Nason et al. |
| 5,640,764 A | 6/1997 | Strojnik |
| 5,640,954 A | 6/1997 | Pfeiffer et al. |
| 5,643,212 A | 7/1997 | Coutre et al. |
| 5,647,853 A | 7/1997 | Feldmann et al. |
| 5,650,062 A | 7/1997 | Ikeda et al. |
| 5,651,767 A | 7/1997 | Schulman et al. |
| 5,651,869 A | 7/1997 | Yoshioka et al. |
| 5,653,239 A | 8/1997 | Pompei et al. |
| 5,659,454 A | 8/1997 | Vermesse |
| 5,660,163 A | 8/1997 | Schulman et al. |
| 5,665,065 A | 9/1997 | Colman et al. |
| 5,665,222 A | 9/1997 | Heller et al. |
| 5,667,983 A | 9/1997 | Abel et al. |
| 5,670,031 A | 9/1997 | Hintsche et al. |
| 5,678,571 A | 10/1997 | Brown |
| 5,679,690 A | 10/1997 | Andre et al. |
| 5,680,858 A | 10/1997 | Hansen et al. |
| 5,682,233 A | 10/1997 | Brinda |
| 5,686,717 A | 11/1997 | Knowles et al. |
| 5,695,623 A | 12/1997 | Michel et al. |
| 5,695,949 A | 12/1997 | Galen et al. |
| 5,701,894 A | 12/1997 | Cherry et al. |
| 5,704,922 A | 1/1998 | Brown |
| 5,707,502 A | 1/1998 | McCaffrey et al. |
| 5,708,247 A | 1/1998 | McAleer et al. |
| 5,710,630 A | 1/1998 | Essenpreis et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,711,868 A | 1/1998 | Maley et al. |
| 5,718,234 A | 2/1998 | Warden et al. |
| 5,720,733 A | 2/1998 | Brown |
| 5,720,862 A | 2/1998 | Hamamoto et al. |
| 5,721,783 A | 2/1998 | Anderson |
| 5,722,397 A | 3/1998 | Eppstein |
| 5,724,030 A | 3/1998 | Urbas et al. |
| 5,726,646 A | 3/1998 | Bane et al. |
| 5,727,548 A | 3/1998 | Hill et al. |
| 5,729,225 A | 3/1998 | Ledzius |
| 5,730,124 A | 3/1998 | Yamauchi |
| 5,730,654 A | 3/1998 | Brown |
| 5,733,313 A | 3/1998 | Barreras, Sr. et al. |
| 5,735,273 A | 4/1998 | Kurnik et al. |
| 5,735,285 A | 4/1998 | Albert et al. |
| 5,741,211 A | 4/1998 | Renirie et al. |
| 5,741,688 A | 4/1998 | Oxenboll et al. |
| 5,746,217 A | 5/1998 | Erickson et al. |
| 5,748,103 A | 5/1998 | Flach et al. |
| 5,749,907 A | 5/1998 | Mann |
| 5,750,926 A | 5/1998 | Schulman et al. |
| 5,758,290 A | 5/1998 | Nealon et al. |
| 5,769,873 A | 6/1998 | Zadeh |
| 5,770,028 A | 6/1998 | Maley et al. |
| 5,771,001 A | 6/1998 | Cobb |
| 5,771,890 A | 6/1998 | Tamada |
| 5,772,586 A | 6/1998 | Heinonen et al. |
| 5,777,060 A | 7/1998 | Van Antwerp |
| 5,779,665 A | 7/1998 | Mastrototaro et al. |
| 5,781,024 A | 7/1998 | Blomberg et al. |
| 5,782,814 A | 7/1998 | Brown et al. |
| 5,785,681 A | 7/1998 | Indravudh |
| 5,786,439 A | 7/1998 | Van Antwerp et al. |
| 5,786,584 A | 7/1998 | Button et al. |
| 5,788,678 A | 8/1998 | Van Antwerp |
| 5,791,344 A | 8/1998 | Schulman et al. |
| 5,792,117 A | 8/1998 | Brown |
| 5,793,292 A | 8/1998 | Ivey |
| 5,800,420 A | 9/1998 | Gross et al. |
| 5,804,047 A | 9/1998 | Karube et al. |
| 5,804,048 A | 9/1998 | Wong et al. |
| 5,807,315 A | 9/1998 | Van Antwerp et al. |
| 5,807,375 A | 9/1998 | Gross et al. |
| 5,814,599 A | 9/1998 | Mitragotri et al. |
| 5,820,551 A | 10/1998 | Hill et al. |
| 5,820,570 A | 10/1998 | Erickson et al. |
| 5,820,622 A | 10/1998 | Gross et al. |
| 5,822,715 A | 10/1998 | Worthington et al. |
| 5,825,488 A | 10/1998 | Kohl et al. |
| 5,827,179 A | 10/1998 | Lichter et al. |
| 5,827,183 A | 10/1998 | Kurnik et al. |
| 5,827,184 A | 10/1998 | Netherly et al. |
| 5,828,943 A | 10/1998 | Brown |
| 5,830,064 A | 11/1998 | Bradish et al. |
| 5,830,132 A | 11/1998 | Robinson |
| 5,830,341 A | 11/1998 | Gilmartin |
| 5,832,448 A | 11/1998 | Brown |
| 5,833,603 A | 11/1998 | Kovacs et al. |
| 5,834,224 A | 11/1998 | Ruger et al. |
| 5,837,454 A | 11/1998 | Cozzette et al. |
| 5,837,546 A | 11/1998 | Allen et al. |
| 5,840,020 A | 11/1998 | Heinonen et al. |
| 5,842,983 A | 12/1998 | Abel et al. |
| 5,843,140 A | 12/1998 | Strojnik |
| 5,846,702 A | 12/1998 | Deng et al. |
| 5,846,744 A | 12/1998 | Athey et al. |
| 5,851,197 A | 12/1998 | Marano et al. |
| 5,854,078 A | 12/1998 | Asher et al. |
| 5,854,189 A | 12/1998 | Kruse et al. |
| 5,856,758 A | 1/1999 | Joffe et al. |
| 5,857,967 A | 1/1999 | Frid et al. |
| 5,857,983 A | 1/1999 | Douglas et al. |
| 5,860,917 A | 1/1999 | Comanor et al. |
| 5,872,713 A | 2/1999 | Douglas et al. |
| 5,876,484 A | 3/1999 | Raskin et al. |
| 5,879,163 A | 3/1999 | Brown et al. |
| 5,879,311 A | 3/1999 | Duchon et al. |
| 5,880,829 A | 3/1999 | Kauhaniemi et al. |
| 5,882,494 A | 3/1999 | Van Antwerp |
| 5,885,211 A | 3/1999 | Eppstein et al. |
| 5,887,133 A | 3/1999 | Brown et al. |
| 5,891,049 A | 4/1999 | Cyrus et al. |
| 5,897,493 A | 4/1999 | Brown |
| 5,898,025 A | 4/1999 | Burg et al. |
| 5,899,855 A | 5/1999 | Brown |
| 5,913,310 A | 6/1999 | Brown |

(56) References Cited

U.S. PATENT DOCUMENTS

| | | |
|---|---|---|
| 5,917,346 A | 6/1999 | Gord |
| 5,918,603 A | 7/1999 | Brown |
| 5,919,141 A | 7/1999 | Money et al. |
| 5,925,021 A | 7/1999 | Castellano et al. |
| 5,931,791 A | 8/1999 | Saltzstein et al. |
| 5,933,136 A | 8/1999 | Brown |
| 5,935,099 A | 8/1999 | Petterson |
| 5,935,224 A | 8/1999 | Svancarek et al. |
| 5,939,609 A | 8/1999 | Knapp et al. |
| 5,940,801 A | 8/1999 | Brown |
| 5,942,979 A | 8/1999 | Luppino |
| 5,945,345 A | 8/1999 | Blatt et al. |
| 5,947,921 A | 9/1999 | Johnson et al. |
| 5,948,512 A | 9/1999 | Kubota et al. |
| 5,950,632 A | 9/1999 | Reber et al. |
| 5,951,300 A | 9/1999 | Brown |
| 5,951,485 A | 9/1999 | Cyrus et al. |
| 5,951,492 A | 9/1999 | Douglas et al. |
| 5,951,521 A | 9/1999 | Mastrototaro et al. |
| 5,951,836 A | 9/1999 | McAleer et al. |
| 5,954,643 A | 9/1999 | Van Antwerp |
| 5,954,685 A | 9/1999 | Tierny |
| 5,954,700 A | 9/1999 | Kovelman |
| 5,956,501 A | 9/1999 | Brown |
| 5,957,854 A | 9/1999 | Besson et al. |
| 5,957,890 A | 9/1999 | Mann et al. |
| 5,957,958 A | 9/1999 | Schulman et al. |
| 5,960,403 A | 9/1999 | Brown |
| 5,961,451 A | 10/1999 | Reber et al. |
| 5,964,993 A | 10/1999 | Blubaugh, Jr. et al. |
| 5,965,380 A | 10/1999 | Heller et al. |
| 5,968,839 A | 10/1999 | Blatt et al. |
| 5,971,922 A | 10/1999 | Arita et al. |
| 5,971,941 A | 10/1999 | Simons et al. |
| 5,974,124 A | 10/1999 | Schlueter, Jr. et al. |
| 5,977,476 A | 11/1999 | Guha et al. |
| 5,981,294 A | 11/1999 | Blatt et al. |
| 5,989,409 A | 11/1999 | Kurnik et al. |
| 5,994,476 A | 11/1999 | Shin et al. |
| 5,995,860 A | 11/1999 | Sun et al. |
| 5,997,476 A | 12/1999 | Brown |
| 5,999,848 A | 12/1999 | Gord et al. |
| 5,999,849 A | 12/1999 | Gord et al. |
| 6,001,067 A | 12/1999 | Shults et al. |
| 6,002,954 A | 12/1999 | Van Antwerp et al. |
| 6,002,961 A | 12/1999 | Mitragotri et al. |
| 6,004,441 A | 12/1999 | Fujiwara et al. |
| 6,011,984 A | 1/2000 | Van Antwerp et al. |
| 6,014,577 A | 1/2000 | Henning et al. |
| 6,018,678 A | 1/2000 | Mitragotri et al. |
| 6,023,629 A | 2/2000 | Tamada |
| 6,024,699 A | 2/2000 | Surwit et al. |
| 6,026,320 A | 2/2000 | Carlson et al. |
| 6,027,459 A | 2/2000 | Shain et al. |
| 6,027,692 A | 2/2000 | Galen et al. |
| 6,028,413 A | 2/2000 | Brockmann |
| 6,032,059 A | 2/2000 | Henning et al. |
| 6,032,199 A | 2/2000 | Lim et al. |
| 6,033,866 A | 3/2000 | Guo et al. |
| 6,035,237 A | 3/2000 | Schulman et al. |
| 6,040,194 A | 3/2000 | Chick et al. |
| 6,041,253 A | 3/2000 | Kost et al. |
| 6,043,437 A | 3/2000 | Schulman et al. |
| 6,049,727 A | 4/2000 | Crothall |
| 6,052,565 A | 4/2000 | Ishikura et al. |
| 6,055,316 A | 4/2000 | Perlman et al. |
| 6,056,718 A | 5/2000 | Funderburk et al. |
| 6,063,459 A | 5/2000 | Velte |
| 6,066,243 A | 5/2000 | Anderson et al. |
| 6,066,448 A | 5/2000 | Wohlstadter et al. |
| 6,067,474 A | 5/2000 | Schulman et al. |
| 6,068,615 A | 5/2000 | Brown et al. |
| 6,071,249 A | 6/2000 | Cunningham et al. |
| 6,071,251 A | 6/2000 | Cunningham et al. |
| 6,071,294 A | 6/2000 | Simons et al. |
| 6,071,391 A | 6/2000 | Gotoh et al. |
| 6,073,031 A | 6/2000 | Helstab et al. |
| 6,081,736 A | 6/2000 | Colvin et al. |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,091,987 A | 7/2000 | Thompson |
| 6,093,156 A | 7/2000 | Cunningham et al. |
| 6,093,167 A | 7/2000 | Houben et al. |
| 6,093,172 A | 7/2000 | Funderburk et al. |
| 6,096,364 A | 8/2000 | Bok et al. |
| 6,097,480 A | 8/2000 | Kaplan |
| 6,097,831 A | 8/2000 | Wieck et al. |
| 6,099,484 A | 8/2000 | Douglas et al. |
| 6,101,478 A | 8/2000 | Brown |
| 6,103,033 A | 8/2000 | Say et al. |
| 6,106,780 A | 8/2000 | Douglas et al. |
| 6,110,148 A | 8/2000 | Brown et al. |
| 6,110,152 A | 8/2000 | Kovelman |
| 6,113,578 A | 9/2000 | Brown |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,125,978 A | 10/2000 | Ando et al. |
| 6,130,623 A | 10/2000 | MacLellan et al. |
| 6,134,461 A | 10/2000 | Say et al. |
| 6,134,504 A | 10/2000 | Douglas et al. |
| 6,139,718 A | 10/2000 | Kurnik et al. |
| 6,141,573 A | 10/2000 | Kurnik et al. |
| 6,142,939 A | 11/2000 | Eppstein et al. |
| 6,143,164 A | 11/2000 | Heller et al. |
| 6,144,837 A | 11/2000 | Quy |
| 6,144,869 A | 11/2000 | Berner et al. |
| 6,144,871 A | 11/2000 | Saito et al. |
| 6,144,922 A | 11/2000 | Douglas et al. |
| 6,148,094 A | 11/2000 | Kinsella |
| 6,150,128 A | 11/2000 | Uretsky |
| 6,151,586 A | 11/2000 | Brown |
| 6,153,062 A | 11/2000 | Saito et al. |
| 6,153,069 A | 11/2000 | Pottgen et al. |
| 6,159,147 A | 12/2000 | Lichter et al. |
| 6,161,095 A | 12/2000 | Brown |
| 6,162,611 A | 12/2000 | Heller et al. |
| 6,162,639 A | 12/2000 | Douglas |
| 6,164,284 A | 12/2000 | Schulman et al. |
| 6,167,362 A | 12/2000 | Brown et al. |
| 6,168,563 B1 | 1/2001 | Brown |
| 6,170,318 B1 | 1/2001 | Lewis |
| 6,175,752 B1 | 1/2001 | Say et al. |
| 6,180,416 B1 | 1/2001 | Kurnik et al. |
| 6,186,145 B1 | 2/2001 | Brown |
| 6,192,891 B1 | 2/2001 | Gravel et al. |
| 6,193,873 B1 | 2/2001 | Ohara et al. |
| 6,196,970 B1 | 3/2001 | Brown |
| 6,198,957 B1 | 3/2001 | Green |
| 6,200,265 B1 | 3/2001 | Walsh et al. |
| 6,201,979 B1 | 3/2001 | Kurnik et al. |
| 6,201,980 B1 | 3/2001 | Darrow et al. |
| 6,203,495 B1 | 3/2001 | Bardy et al. |
| 6,206,841 B1 | 3/2001 | Cunningham et al. |
| 6,207,400 B1 | 3/2001 | Kwon |
| 6,208,894 B1 | 3/2001 | Schulman et al. |
| 6,210,272 B1 | 4/2001 | Brown |
| 6,210,976 B1 | 4/2001 | Sabbadini |
| 6,212,416 B1 | 4/2001 | Ward et al. |
| 6,218,809 B1 | 4/2001 | Downs et al. |
| 6,219,565 B1 | 4/2001 | Cupp et al. |
| 6,219,574 B1 | 4/2001 | Cormier et al. |
| 6,224,745 B1 | 5/2001 | Baltruschat |
| 6,232,130 B1 | 5/2001 | Wolf |
| 6,232,370 B1 | 5/2001 | Kubota et al. |
| 6,233,471 B1 | 5/2001 | Berner et al. |
| 6,233,539 B1 | 5/2001 | Brown |
| 6,239,925 B1 | 5/2001 | Ardrey et al. |
| 6,241,862 B1 | 6/2001 | McAleer et al. |

(56) References Cited

U.S. PATENT DOCUMENTS

| | | |
|---|---|---|
| 6,246,330 B1 | 6/2001 | Nielsen |
| 6,246,992 B1 | 6/2001 | Brown |
| 6,248,065 B1 | 6/2001 | Brown |
| 6,248,067 B1 | 6/2001 | Causey, III et al. |
| 6,248,093 B1 | 6/2001 | Moberg |
| 6,251,260 B1 | 6/2001 | Heller et al. |
| 6,252,032 B1 | 6/2001 | Van Antwerp et al. |
| 6,253,804 B1 | 7/2001 | Safabash |
| 6,254,586 B1 | 7/2001 | Mann et al. |
| 6,256,643 B1 | 7/2001 | Cork et al. |
| 6,259,587 B1 | 7/2001 | Sheldon et al. |
| 6,259,937 B1 | 7/2001 | Schulman et al. |
| 6,260,022 B1 | 7/2001 | Brown |
| 6,266,645 B1 | 7/2001 | Simpson |
| 6,267,724 B1 | 7/2001 | Taylor |
| 6,268,161 B1 | 7/2001 | Han et al. |
| 6,270,445 B1 | 8/2001 | Dean, Jr. et al. |
| 6,270,455 B1 | 8/2001 | Brown |
| 6,272,364 B1 | 8/2001 | Kurnik |
| 6,275,717 B1 | 8/2001 | Gross et al. |
| 6,280,416 B1 | 8/2001 | Van Antwerp et al. |
| 6,280,587 B1 | 8/2001 | Matsumoto |
| 6,281,006 B1 | 8/2001 | Heller et al. |
| 6,283,943 B1 | 9/2001 | Dy et al. |
| 6,284,126 B1 | 9/2001 | Kurnik et al. |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,281 B1 | 9/2001 | Heller |
| 6,294,997 B1 | 9/2001 | Paratore et al. |
| 6,295,463 B1 | 9/2001 | Stenzler |
| 6,295,506 B1 | 9/2001 | Heinonen et al. |
| 6,298,254 B2 | 10/2001 | Tamada |
| 6,299,347 B1 | 10/2001 | Pompei |
| 6,299,578 B1 | 10/2001 | Kurnik et al. |
| 6,299,757 B1 | 10/2001 | Feldman et al. |
| 6,301,499 B1 | 10/2001 | Carlson et al. |
| 6,304,766 B1 | 10/2001 | Colvin, Jr. et al. |
| 6,306,104 B1 | 10/2001 | Cunningham et al. |
| 6,307,867 B1 | 10/2001 | Roobol et al. |
| 6,309,351 B1 | 10/2001 | Kurnik et al. |
| 6,309,884 B1 | 10/2001 | Cooper et al. |
| 6,313,749 B1 | 11/2001 | Horne et al. |
| 6,314,317 B1 | 11/2001 | Willis |
| 6,315,721 B2 | 11/2001 | Schulman et al. |
| 6,319,540 B1 | 11/2001 | Van Antwerp et al. |
| 6,326,160 B1 | 12/2001 | Dunn et al. |
| 6,329,161 B1 | 12/2001 | Heller et al. |
| 6,329,929 B1 | 12/2001 | Weijand et al. |
| 6,330,426 B2 | 12/2001 | Brown et al. |
| 6,330,464 B1 | 12/2001 | Colvin, Jr. et al. |
| 6,331,518 B2 | 12/2001 | Hemm et al. |
| 6,334,778 B1 | 1/2002 | Brown |
| 6,336,900 B1 | 1/2002 | Alleckson et al. |
| 6,338,790 B1 | 1/2002 | Feldman et al. |
| 6,340,421 B1 | 1/2002 | Vachon et al. |
| 6,341,232 B1 | 1/2002 | Conn et al. |
| 6,356,776 B1 | 3/2002 | Berner et al. |
| 6,359,270 B1 | 3/2002 | Bridson |
| 6,359,594 B1 | 3/2002 | Junod |
| 6,360,888 B1 | 3/2002 | McIvor et al. |
| 6,366,793 B1 | 4/2002 | Bell et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,370,410 B2 | 4/2002 | Kurnik et al. |
| 6,377,828 B1 | 4/2002 | Chaiken et al. |
| 6,379,301 B1 | 4/2002 | Worthington et al. |
| 6,383,767 B1 | 5/2002 | Polak |
| 6,385,473 B1 | 5/2002 | Haines et al. |
| 6,387,048 B1 | 5/2002 | Schulman et al. |
| 6,391,643 B1 | 5/2002 | Chen et al. |
| 6,393,318 B1 | 5/2002 | Conn et al. |
| 6,398,562 B1 | 6/2002 | Butler et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,332 B1 | 7/2002 | Mastrototaro et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,434,409 B1 | 8/2002 | Pfeiffer et al. |
| 6,438,414 B1 | 8/2002 | Conn et al. |
| 6,440,068 B1 | 8/2002 | Brown et al. |
| 6,442,637 B1 | 8/2002 | Hawkins et al. |
| 6,442,672 B1 | 8/2002 | Ganapathy |
| 6,443,942 B2 | 9/2002 | Van Antwerp et al. |
| 6,449,255 B1 | 9/2002 | Waclawsky et al. |
| 6,454,710 B1 | 9/2002 | Ballerstadt et al. |
| 6,462,162 B2 | 10/2002 | Van Antwerp et al. |
| 6,464,848 B1 | 10/2002 | Matsumoto |
| 6,466,810 B1 | 10/2002 | Ward et al. |
| 6,468,222 B1 | 10/2002 | Mault et al. |
| 6,471,689 B1 | 10/2002 | Joseph et al. |
| 6,472,122 B1 | 10/2002 | Schulman et al. |
| 6,475,750 B1 | 11/2002 | Han et al. |
| 6,477,395 B2 | 11/2002 | Schulman et al. |
| 6,478,736 B1 | 11/2002 | Mault |
| 6,480,730 B2 | 11/2002 | Darrow et al. |
| 6,480,744 B2 | 11/2002 | Ferek-Petric |
| 6,482,156 B2 | 11/2002 | Iliff |
| 6,482,158 B2 | 11/2002 | Mault |
| 6,482,604 B2 | 11/2002 | Kwon |
| 6,484,045 B1 | 11/2002 | Holker et al. |
| 6,484,046 B1 | 11/2002 | Say et al. |
| 6,485,138 B1 | 11/2002 | Kubota et al. |
| 6,493,069 B1 | 12/2002 | Nagashimada et al. |
| 6,494,830 B1 | 12/2002 | Wessel |
| 6,496,728 B2 | 12/2002 | Li et al. |
| 6,496,729 B2 | 12/2002 | Thompson |
| 6,497,655 B1 | 12/2002 | Linberg et al. |
| 6,505,059 B1 | 1/2003 | Kollias et al. |
| 6,505,121 B1 | 1/2003 | Russel |
| 6,512,939 B1 | 1/2003 | Colvin et al. |
| 6,513,532 B2 | 2/2003 | Mault et al. |
| 6,514,718 B2 | 2/2003 | Heller et al. |
| 6,515,593 B1 | 2/2003 | Stark et al. |
| 6,520,326 B2 | 2/2003 | McIvor et al. |
| 6,529,755 B2 | 3/2003 | Kurnik et al. |
| 6,529,772 B2 | 3/2003 | Carlson et al. |
| 6,530,915 B1 | 3/2003 | Eppstein et al. |
| 6,534,322 B1 | 3/2003 | Sabbadini |
| 6,534,323 B1 | 3/2003 | Sabbadini |
| 6,535,753 B1 | 3/2003 | Raskas |
| 6,537,243 B1 | 3/2003 | Henning et al. |
| 6,540,675 B2 | 4/2003 | Aceti et al. |
| 6,541,266 B2 | 4/2003 | Modzelweskei et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,549,796 B2 | 4/2003 | Sohrab |
| 6,551,276 B1 | 4/2003 | Mann et al. |
| 6,551,494 B1 | 4/2003 | Heller et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,564,807 B1 | 5/2003 | Schulman et al. |
| 6,565,509 B1 | 5/2003 | Say et al. |
| 6,571,128 B2 | 5/2003 | Lebel et al. |
| 6,571,200 B1 | 5/2003 | Mault |
| 6,572,545 B2 | 6/2003 | Knobbe et al. |
| 6,574,510 B2 | 6/2003 | Von Arx et al. |
| 6,576,101 B1 | 6/2003 | Heller et al. |
| 6,576,117 B1 | 6/2003 | Iketaki et al. |
| 6,577,899 B2 | 6/2003 | Lebel et al. |
| 6,579,231 B1 | 6/2003 | Phipps |

(56) References Cited

U.S. PATENT DOCUMENTS

| | | |
|---|---|---|
| 6,579,498 B1 | 6/2003 | Eglise |
| 6,579,690 B1 | 6/2003 | Bonnecaze et al. |
| 6,580,364 B1 | 6/2003 | Munch et al. |
| 6,584,335 B1 | 6/2003 | Haar et al. |
| 6,585,644 B2 | 7/2003 | Lebel et al. |
| 6,587,705 B1 | 7/2003 | Kim et al. |
| 6,591,125 B1 | 7/2003 | Buse et al. |
| 6,591,126 B2 | 7/2003 | Roeper et al. |
| 6,594,514 B2 | 7/2003 | Berner et al. |
| 6,595,919 B2 | 7/2003 | Berner et al. |
| 6,595,929 B2 | 7/2003 | Stivoric et al. |
| 6,602,678 B2 | 8/2003 | Kwon et al. |
| 6,602,909 B1 | 8/2003 | Jarowski |
| 6,605,200 B1 | 8/2003 | Mao et al. |
| 6,605,201 B1 | 8/2003 | Mao et al. |
| 6,607,509 B2 | 8/2003 | Bobroff et al. |
| 6,608,562 B1 | 8/2003 | Kimura et al. |
| 6,610,012 B2 | 8/2003 | Mault |
| 6,611,206 B2 | 8/2003 | Eshelman et al. |
| 6,612,306 B1 | 9/2003 | Mault |
| 6,615,078 B1 | 9/2003 | Burson et al. |
| 6,616,613 B1 | 9/2003 | Goodman |
| 6,618,603 B2 | 9/2003 | Varalli et al. |
| 6,620,106 B2 | 9/2003 | Mault |
| 6,627,058 B1 | 9/2003 | Chan |
| 6,627,154 B1 | 9/2003 | Goodman et al. |
| 6,629,934 B2 | 10/2003 | Mault et al. |
| 6,633,772 B2 | 10/2003 | Ford et al. |
| 6,635,014 B2 | 10/2003 | Starkweather et al. |
| 6,635,167 B1 * | 10/2003 | Batman et al. ............... 205/775 |
| 6,641,533 B2 | 11/2003 | Causey, III et al. |
| 6,642,015 B2 | 11/2003 | Vachon et al. |
| 6,645,142 B2 | 11/2003 | Braig et al. |
| 6,645,368 B1 | 11/2003 | Beaty et al. |
| 6,648,821 B2 | 11/2003 | Lebel et al. |
| 6,653,091 B1 | 11/2003 | Dunn et al. |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,671,554 B2 | 12/2003 | Gibson et al. |
| 6,673,625 B2 | 1/2004 | Satcher, Jr. et al. |
| 6,682,938 B1 | 1/2004 | Satcher, Jr. et al. |
| 6,683,040 B2 | 1/2004 | Bragulla et al. |
| 6,687,522 B2 | 2/2004 | Tamada |
| 6,687,546 B2 | 2/2004 | Lebel et al. |
| 6,689,056 B1 | 2/2004 | Kilcoyne et al. |
| 6,690,276 B1 | 2/2004 | Marino |
| 6,692,446 B2 | 2/2004 | Hoek |
| 6,693,069 B2 | 2/2004 | Korber et al. |
| 6,694,158 B2 | 2/2004 | Polak |
| 6,694,191 B2 | 2/2004 | Starkweather et al. |
| 6,695,860 B1 | 2/2004 | Ward et al. |
| 6,698,269 B2 | 3/2004 | Baber et al. |
| 6,701,270 B1 | 3/2004 | Miller et al. |
| 6,702,857 B2 | 3/2004 | Brauker et al. |
| 6,704,587 B1 | 3/2004 | Kumar et al. |
| 6,708,057 B2 | 3/2004 | Marganroth |
| 6,711,423 B2 | 3/2004 | Colvin, Jr. |
| 6,723,046 B2 | 4/2004 | Lichtenstein et al. |
| 6,728,560 B2 | 4/2004 | Kollias et al. |
| 6,730,025 B1 | 5/2004 | Platt |
| 6,731,976 B2 | 5/2004 | Penn et al. |
| 6,733,446 B2 | 5/2004 | Lebel et al. |
| 6,734,162 B2 | 5/2004 | Van Antwerp et al. |
| 6,735,183 B2 | 5/2004 | O'Toole et al. |
| 6,735,479 B2 | 5/2004 | Fabian et al. |
| 6,736,777 B2 | 5/2004 | Kim et al. |
| 6,736,797 B1 | 5/2004 | Larsen et al. |
| 6,737,401 B2 | 5/2004 | Kim et al. |
| 6,738,654 B2 | 5/2004 | Sohrab |
| 6,740,075 B2 | 5/2004 | Lebel et al. |
| 6,741,163 B1 | 5/2004 | Roberts |
| 6,741,876 B1 | 5/2004 | Scecina et al. |
| 6,741,877 B1 | 5/2004 | Shults et al. |
| 6,746,582 B2 | 6/2004 | Heller et al. |
| 6,748,445 B1 | 6/2004 | Darcey et al. |
| 6,749,587 B2 | 6/2004 | Flaherty |
| 6,750,311 B1 | 6/2004 | Van Antwerp et al. |
| 6,758,810 B2 | 7/2004 | Lebel et al. |
| 6,766,183 B2 | 7/2004 | Walsh et al. |
| 6,766,201 B2 | 7/2004 | Von Arx et al. |
| 6,768,425 B2 | 7/2004 | Flaherty et al. |
| 6,770,030 B1 | 8/2004 | Schaupp et al. |
| 6,770,729 B2 | 8/2004 | Van Antwerp et al. |
| 6,771,995 B2 | 8/2004 | Kurnik et al. |
| 6,773,563 B2 | 8/2004 | Matsumoto |
| 6,780,156 B2 | 8/2004 | Haueter et al. |
| 6,780,297 B2 | 8/2004 | Matsumoto et al. |
| 6,780,871 B2 | 8/2004 | Glick et al. |
| 6,784,274 B2 | 8/2004 | Van Antwerp et al. |
| 6,790,178 B1 | 9/2004 | Mault et al. |
| 6,794,195 B2 | 9/2004 | Colvin, Jr. |
| 6,800,451 B2 | 10/2004 | Daniloff et al. |
| 6,804,544 B2 | 10/2004 | Van Antwerp et al. |
| 6,804,558 B2 | 10/2004 | Haller et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,810,309 B2 | 10/2004 | Sadler et al. |
| 6,811,533 B2 | 11/2004 | Lebel et al. |
| 6,811,534 B2 | 11/2004 | Bowman, IV et al. |
| 6,811,659 B2 | 11/2004 | Vachon |
| 6,812,031 B1 | 11/2004 | Carlsson |
| 6,813,519 B2 | 11/2004 | Lebel et al. |
| 6,816,742 B2 | 11/2004 | Kim et al. |
| 6,835,553 B2 | 12/2004 | Han et al. |
| RE38,681 E | 1/2005 | Kurnik et al. |
| 6,840,912 B2 | 1/2005 | Kloepfer et al. |
| 6,844,023 B2 | 1/2005 | Schulman et al. |
| 6,849,237 B2 | 2/2005 | Housefield et al. |
| 6,850,790 B2 | 2/2005 | Berner et al. |
| 6,852,104 B2 | 2/2005 | Blomquist |
| 6,852,500 B1 | 2/2005 | Hoss et al. |
| 6,852,694 B2 | 2/2005 | Van Antwerp et al. |
| 6,853,854 B1 | 2/2005 | Proniewicz et al. |
| 6,856,928 B2 | 2/2005 | Harmon |
| 6,858,403 B2 | 2/2005 | Han et al. |
| 6,862,465 B2 | 3/2005 | Shults et al. |
| 6,862,466 B2 | 3/2005 | Ackerman |
| 6,872,200 B2 | 3/2005 | Mann et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,885,883 B2 | 4/2005 | Parris et al. |
| 6,889,331 B2 | 5/2005 | Soerensen et al. |
| 6,892,085 B2 | 5/2005 | McIvor et al. |
| 6,893,396 B2 | 5/2005 | Schulze et al. |
| 6,895,263 B2 | 5/2005 | Shin et al. |
| 6,895,265 B2 | 5/2005 | Silver |
| 6,899,683 B2 | 5/2005 | Mault et al. |
| 6,899,684 B2 | 5/2005 | Mault et al. |
| 6,902,207 B2 | 6/2005 | Lickliter |
| 6,902,905 B2 | 6/2005 | Burson et al. |
| 6,904,301 B2 | 6/2005 | Raskas |
| 6,907,127 B1 | 6/2005 | Kravitz et al. |
| 6,915,147 B2 | 7/2005 | Lebel et al. |
| 6,918,874 B1 | 7/2005 | Hatch et al. |
| 6,922,578 B2 | 7/2005 | Eppstein et al. |
| RE38,775 E | 8/2005 | Kurnik et al. |
| 6,923,764 B2 | 8/2005 | Aceti et al. |
| 6,923,936 B2 | 8/2005 | Swanson et al. |
| 6,926,670 B2 | 8/2005 | Rich et al. |
| 6,927,246 B2 | 8/2005 | Noronha et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,936,029 B2 | 8/2005 | Mann et al. |
| 6,937,222 B2 | 8/2005 | Numao |
| 6,940,403 B2 | 9/2005 | Kail, IV |
| 6,940,590 B2 | 9/2005 | Colvin, Jr. et al. |
| 6,941,163 B2 | 9/2005 | Ford et al. |

(56) References Cited

U.S. PATENT DOCUMENTS

| | | |
|---|---|---|
| 6,950,708 B2 | 9/2005 | Bowman, IV et al. |
| 6,952,603 B2 | 10/2005 | Gerber et al. |
| 6,954,673 B2 | 10/2005 | Von Arx et al. |
| 6,955,650 B2 | 10/2005 | Mault et al. |
| 6,957,102 B2 | 10/2005 | Silver et al. |
| 6,957,107 B2 | 10/2005 | Rogers et al. |
| 6,958,705 B2 | 10/2005 | Lebel et al. |
| 6,968,294 B2 | 11/2005 | Gutta et al. |
| 6,968,375 B1 | 11/2005 | Brown |
| 6,971,274 B2 | 12/2005 | Olin |
| 6,974,437 B2 | 12/2005 | Lebel et al. |
| 6,978,182 B2 | 12/2005 | Mazar et al. |
| 6,979,326 B2 | 12/2005 | Mann et al. |
| 6,983,176 B2 | 1/2006 | Gardner et al. |
| 6,985,870 B2 | 1/2006 | Martucci et al. |
| 6,987,474 B2 | 1/2006 | Freeman et al. |
| 6,990,317 B2 | 1/2006 | Arnold |
| 6,990,366 B2 | 1/2006 | Say et al. |
| 6,991,096 B2 | 1/2006 | Gottlieb et al. |
| 6,997,907 B2 | 2/2006 | Safabash et al. |
| 6,997,920 B2 | 2/2006 | Mann et al. |
| 6,998,247 B2 | 2/2006 | Monfre et al. |
| 6,999,810 B2 | 2/2006 | Berner et al. |
| 7,003,336 B2 | 2/2006 | Holker et al. |
| 7,003,340 B2 | 2/2006 | Say et al. |
| 7,003,341 B2 | 2/2006 | Say et al. |
| 7,004,901 B2 | 2/2006 | Fish |
| 7,005,857 B2 | 2/2006 | Stiene et al. |
| 7,009,511 B2 | 3/2006 | Mazar et al. |
| 7,011,630 B2 | 3/2006 | Desai et al. |
| 7,018,366 B2 | 3/2006 | Easter |
| 7,018,568 B2 | 3/2006 | Tierney |
| 7,020,508 B2 | 3/2006 | Stivoric et al. |
| 7,022,072 B2 | 4/2006 | Fox et al. |
| 7,024,236 B2 | 4/2006 | Ford et al. |
| 7,024,245 B2 | 4/2006 | Lebel et al. |
| 7,025,743 B2 | 4/2006 | Mann et al. |
| 7,027,931 B1 | 4/2006 | Jones et al. |
| 7,029,444 B2 | 4/2006 | Shin et al. |
| 7,039,810 B1 | 5/2006 | Nichols |
| 7,041,068 B2 | 5/2006 | Freeman et al. |
| 7,041,468 B2 | 5/2006 | Drucker et al. |
| 7,043,305 B2 | 5/2006 | KenKnight et al. |
| 7,049,277 B2 | 5/2006 | Bagulla et al. |
| 7,052,251 B2 | 5/2006 | Nason et al. |
| 7,052,472 B1 | 5/2006 | Miller et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,030 B2 | 6/2006 | Von Arx et al. |
| 7,060,031 B2 | 6/2006 | Webb et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,089,780 B2 | 8/2006 | Sunshine et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,114,502 B2 | 10/2006 | Schulman et al. |
| 7,124,027 B1 | 10/2006 | Ernst et al. |
| 7,125,382 B2 | 10/2006 | Zhou et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,150,975 B2 | 12/2006 | Tamada et al. |
| 7,154,398 B2 | 12/2006 | Chen et al. |
| 7,155,112 B2 | 12/2006 | Uno et al. |
| 7,155,290 B2 | 12/2006 | Von Arx et al. |
| 7,163,511 B2 | 1/2007 | Conn et al. |
| 7,167,818 B2 | 1/2007 | Brown |
| 7,171,274 B2 | 1/2007 | Starkweather et al. |
| 7,174,199 B2 | 2/2007 | Berner et al. |
| 7,183,068 B2 | 2/2007 | Burson et al. |
| 7,183,102 B2 | 2/2007 | Monfre et al. |
| 7,189,341 B2 | 3/2007 | Li et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,221,977 B1 | 5/2007 | Weaver et al. |
| 7,222,054 B2 | 5/2007 | Geva |
| 7,226,442 B2 | 6/2007 | Sheppard et al. |
| 7,226,978 B2 | 6/2007 | Tapsak et al. |
| 7,228,162 B2 | 6/2007 | Ward et al. |
| 7,228,163 B2 | 6/2007 | Ackerman |
| 7,228,182 B2 | 6/2007 | Healy et al. |
| 7,233,817 B2 | 6/2007 | Yen |
| 7,237,712 B2 | 7/2007 | DeRocco et al. |
| 7,241,266 B2 | 7/2007 | Zhou et al. |
| 7,258,665 B2 | 8/2007 | Kohls et al. |
| 7,261,691 B1 | 8/2007 | Asomani |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,291,107 B2 | 11/2007 | Hellwig et al. |
| 7,295,867 B2 | 11/2007 | Berner et al. |
| 7,297,112 B2 | 11/2007 | Zhou et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,324,850 B2 | 1/2008 | Persen et al. |
| 7,335,294 B2 | 2/2008 | Heller et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,398,183 B2 | 7/2008 | Holland et al. |
| 7,399,277 B2 | 7/2008 | Saidara et al. |
| 7,402,153 B2 | 7/2008 | Steil et al. |
| 7,408,132 B2 | 8/2008 | Wambsganss et al. |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,492,254 B2 | 2/2009 | Bandy et al. |
| 7,494,465 B2 | 2/2009 | Brister et al. |
| 7,497,827 B2 | 3/2009 | Brister et al. |
| 7,506,046 B2 | 3/2009 | Rhodes |
| 7,519,408 B2 | 4/2009 | Rasdal et al. |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,668,596 B2 | 2/2010 | Von Arx et al. |
| 7,699,775 B2 | 4/2010 | Desai et al. |
| 7,701,052 B2 | 4/2010 | Borland et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,741,734 B2 | 6/2010 | Joannopoulos et al. |

(56) References Cited

U.S. PATENT DOCUMENTS

| | | |
|---|---|---|
| 7,766,829 B2 | 8/2010 | Sloan et al. |
| 7,768,387 B2 | 8/2010 | Fennell et al. |
| 7,771,352 B2 | 8/2010 | Shults et al. |
| 7,774,145 B2 | 8/2010 | Brauker et al. |
| 7,775,444 B2 | 8/2010 | DeRocco et al. |
| 7,778,680 B2 | 8/2010 | Goode, Jr. et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,804,197 B2 | 9/2010 | Iisaka et al. |
| 7,811,231 B2 | 10/2010 | Jin et al. |
| 7,813,809 B2 | 10/2010 | Strother et al. |
| 7,826,382 B2 | 11/2010 | Sicurello et al. |
| 7,826,981 B2 | 11/2010 | Goode, Jr. et al. |
| 7,831,310 B2 | 11/2010 | Lebel et al. |
| 7,833,151 B2 | 11/2010 | Khait et al. |
| 7,860,574 B2 | 12/2010 | Von Arx et al. |
| 7,882,611 B2 | 2/2011 | Shah et al. |
| 7,889,069 B2 | 2/2011 | Fifolt et al. |
| 7,899,511 B2 | 3/2011 | Shults et al. |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,948,369 B2 | 5/2011 | Fennell et al. |
| 7,955,258 B2 | 6/2011 | Goscha et al. |
| 7,970,448 B2 | 6/2011 | Shults et al. |
| 7,974,672 B2 | 7/2011 | Shults et al. |
| 7,978,063 B2 | 7/2011 | Baldus et al. |
| 7,999,674 B2 | 8/2011 | Kamen |
| 8,000,918 B2 | 8/2011 | Fjield et al. |
| 8,010,174 B2 | 8/2011 | Goode et al. |
| 8,010,256 B2 | 8/2011 | Oowada |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,123,686 B2 | 2/2012 | Fennell et al. |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,149,103 B2 | 4/2012 | Fennell et al. |
| 8,150,321 B2 | 4/2012 | Winter et al. |
| 8,150,516 B2 | 4/2012 | Levine et al. |
| 8,179,266 B2 | 5/2012 | Hermle |
| 8,233,456 B1 | 7/2012 | Kopikare et al. |
| 8,260,393 B2 | 9/2012 | Kamath et al. |
| 8,282,549 B2 | 10/2012 | Brauker et al. |
| 8,417,312 B2 | 4/2013 | Kamath et al. |
| 8,478,389 B1 | 7/2013 | Brockway et al. |
| 8,560,037 B2 | 10/2013 | Goode, Jr. et al. |
| 8,622,903 B2 | 1/2014 | Jin et al. |
| 8,638,411 B2 | 1/2014 | Park et al. |
| 8,849,459 B2 * | 9/2014 | Ramey et al. ................ 700/266 |
| 8,914,090 B2 | 12/2014 | Jain et al. |
| 8,937,540 B2 | 1/2015 | Fennell |
| 2001/0011224 A1 | 8/2001 | Brown |
| 2001/0011795 A1 | 8/2001 | Ohtsuka et al. |
| 2001/0016310 A1 | 8/2001 | Brown et al. |
| 2001/0016682 A1 | 8/2001 | Berner et al. |
| 2001/0016683 A1 | 8/2001 | Darrow et al. |
| 2001/0020124 A1 | 9/2001 | Tamada |
| 2001/0029340 A1 | 10/2001 | Mault et al. |
| 2001/0032278 A1 | 10/2001 | Brown et al. |
| 2001/0037060 A1 | 11/2001 | Thompson et al. |
| 2001/0037069 A1 | 11/2001 | Carlson et al. |
| 2001/0037366 A1 | 11/2001 | Webb et al. |
| 2001/0039504 A1 | 11/2001 | Linberg et al. |
| 2001/0041830 A1 | 11/2001 | Varalli et al. |
| 2001/0041831 A1 | 11/2001 | Starkweather et al. |
| 2001/0044581 A1 | 11/2001 | Mault |
| 2001/0044588 A1 | 11/2001 | Mault |
| 2001/0047125 A1 | 11/2001 | Quy |
| 2001/0047127 A1 | 11/2001 | New et al. |
| 2001/0049096 A1 | 12/2001 | Brown |
| 2001/0049470 A1 | 12/2001 | Mault et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0013522 A1 | 1/2002 | Lav et al. |
| 2002/0013538 A1 | 1/2002 | Teller |
| 2002/0016530 A1 | 2/2002 | Brown |
| 2002/0016719 A1 | 2/2002 | Nemeth et al. |
| 2002/0019022 A1 | 2/2002 | Dunn et al. |
| 2002/0019584 A1 | 2/2002 | Schulze et al. |
| 2002/0019586 A1 | 2/2002 | Teller et al. |
| 2002/0019748 A1 | 2/2002 | Brown |
| 2002/0023852 A1 | 2/2002 | McIvor et al. |
| 2002/0026111 A1 | 2/2002 | Ackerman |
| 2002/0026937 A1 | 3/2002 | Mault |
| 2002/0027164 A1 | 3/2002 | Mault et al. |
| 2002/0028995 A1 | 3/2002 | Mault |
| 2002/0040208 A1 | 4/2002 | Flaherty et al. |
| 2002/0042090 A1 | 4/2002 | Heller et al. |
| 2002/0045808 A1 | 4/2002 | Ford et al. |
| 2002/0046300 A1 | 4/2002 | Hanko et al. |
| 2002/0047867 A1 | 4/2002 | Mault et al. |
| 2002/0049482 A1 | 4/2002 | Fabian et al. |
| 2002/0053637 A1 | 5/2002 | Conn et al. |
| 2002/0062069 A1 | 5/2002 | Mault |
| 2002/0063060 A1 | 5/2002 | Gascoyne et al. |
| 2002/0065454 A1 | 5/2002 | Lebel et al. |
| 2002/0068858 A1 | 6/2002 | Braig et al. |
| 2002/0072784 A1 | 6/2002 | Sheppard et al. |
| 2002/0072858 A1 | 6/2002 | Cheng |
| 2002/0074162 A1 | 6/2002 | Su et al. |
| 2002/0077765 A1 | 6/2002 | Mault |
| 2002/0077766 A1 | 6/2002 | Mault |
| 2002/0081559 A1 | 6/2002 | Brown et al. |
| 2002/0083461 A1 | 6/2002 | Hutcheson et al. |
| 2002/0084196 A1 | 7/2002 | Liamos et al. |
| 2002/0087056 A1 | 7/2002 | Aceti et al. |
| 2002/0091312 A1 | 7/2002 | Berner et al. |
| 2002/0091796 A1 | 7/2002 | Higginson et al. |
| 2002/0093969 A1 | 7/2002 | Lin et al. |
| 2002/0103425 A1 | 8/2002 | Mault |
| 2002/0103499 A1 | 8/2002 | Perez et al. |
| 2002/0106709 A1 | 8/2002 | Potts et al. |
| 2002/0107433 A1 | 8/2002 | Mault |
| 2002/0107476 A1 | 8/2002 | Mann et al. |
| 2002/0109600 A1 | 8/2002 | Mault et al. |
| 2002/0109621 A1 | 8/2002 | Khair et al. |
| 2002/0117639 A1 | 8/2002 | Paolini et al. |
| 2002/0118528 A1 | 8/2002 | Su et al. |
| 2002/0119711 A1 | 8/2002 | Van Antwerp et al. |

(56) References Cited

U.S. PATENT DOCUMENTS

| | | |
|---|---|---|
| 2002/0124017 A1 | 9/2002 | Mault |
| 2002/0126036 A1 | 9/2002 | Flaherty et al. |
| 2002/0128594 A1 | 9/2002 | Das et al. |
| 2002/0130042 A1 | 9/2002 | Moerman et al. |
| 2002/0133378 A1 | 9/2002 | Mault et al. |
| 2002/0147135 A1 | 10/2002 | Schnell |
| 2002/0161286 A1 | 10/2002 | Gerber et al. |
| 2002/0161288 A1 | 10/2002 | Shin et al. |
| 2002/0169394 A1 | 11/2002 | Eppstein et al. |
| 2002/0169635 A1 | 11/2002 | Shillingburg |
| 2002/0177764 A1 | 11/2002 | Sohrab |
| 2002/0185130 A1 | 12/2002 | Wright et al. |
| 2002/0193679 A1 | 12/2002 | Malave et al. |
| 2003/0004403 A1 | 1/2003 | Drinan et al. |
| 2003/0009203 A1 | 1/2003 | Lebel et al. |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032077 A1 | 2/2003 | Itoh et al. |
| 2003/0032867 A1 | 2/2003 | Crothall et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0042137 A1 | 3/2003 | Mao et al. |
| 2003/0050537 A1 | 3/2003 | Wessel |
| 2003/0050546 A1 | 3/2003 | Desai et al. |
| 2003/0060689 A1 | 3/2003 | Kohls et al. |
| 2003/0060692 A1 | 3/2003 | Ruchti et al. |
| 2003/0060753 A1 | 3/2003 | Starkweather et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0076792 A1 | 4/2003 | Theimer |
| 2003/0081370 A1 | 5/2003 | Haskell et al. |
| 2003/0100040 A1 | 5/2003 | Bonnecaze et al. |
| 2003/0100821 A1 | 5/2003 | Heller et al. |
| 2003/0105407 A1 | 6/2003 | Pearce et al. |
| 2003/0108976 A1 | 6/2003 | Braig et al. |
| 2003/0114897 A1 | 6/2003 | Von Arx et al. |
| 2003/0119457 A1 | 6/2003 | Standke |
| 2003/0122021 A1 | 7/2003 | McConnell et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0144579 A1 | 7/2003 | Buss |
| 2003/0146841 A1 | 8/2003 | Koenig |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158707 A1 | 8/2003 | Doi |
| 2003/0168338 A1 | 9/2003 | Gao et al. |
| 2003/0175806 A1 | 9/2003 | Rule et al. |
| 2003/0175992 A1 | 9/2003 | Toranto et al. |
| 2003/0176183 A1 | 9/2003 | Drucker et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0199790 A1 | 10/2003 | Boecker et al. |
| 2003/0199791 A1 | 10/2003 | Boecker et al. |
| 2003/0199903 A1 | 10/2003 | Boecker et al. |
| 2003/0203498 A1 | 10/2003 | Neel et al. |
| 2003/0204290 A1 | 10/2003 | Sadler et al. |
| 2003/0208110 A1 | 11/2003 | Mault et al. |
| 2003/0208113 A1 | 11/2003 | Mault et al. |
| 2003/0208114 A1 | 11/2003 | Ackerman |
| 2003/0208133 A1 | 11/2003 | Mault |
| 2003/0208409 A1 | 11/2003 | Mault |
| 2003/0212317 A1 | 11/2003 | Kovatchev et al. |
| 2003/0212364 A1 | 11/2003 | Mann et al. |
| 2003/0212379 A1 | 11/2003 | Bylund et al. |
| 2003/0212579 A1 | 11/2003 | Brown et al. |
| 2003/0216630 A1 | 11/2003 | Jersey-Willuhn et al. |
| 2003/0217966 A1 | 11/2003 | Tapsak et al. |
| 2003/0226695 A1 | 12/2003 | Mault |
| 2003/0229514 A2 | 12/2003 | Brown |
| 2003/0232370 A1 | 12/2003 | Trifiro |
| 2003/0235817 A1 | 12/2003 | Bartkowiak et al. |
| 2004/0010207 A1 | 1/2004 | Flaherty et al. |
| 2004/0011671 A1 | 1/2004 | Shults et al. |
| 2004/0017300 A1 | 1/2004 | Kotzin et al. |
| 2004/0018486 A1 | 1/2004 | Dunn et al. |
| 2004/0030226 A1 | 2/2004 | Quy |
| 2004/0030531 A1 | 2/2004 | Miller et al. |
| 2004/0030581 A1 | 2/2004 | Levin et al. |
| 2004/0034289 A1 | 2/2004 | Teller et al. |
| 2004/0039255 A1 | 2/2004 | Simonsen et al. |
| 2004/0039256 A1 | 2/2004 | Kawatahara et al. |
| 2004/0039298 A1 | 2/2004 | Abreu et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0063435 A1 | 4/2004 | Sakamoto et al. |
| 2004/0064068 A1 | 4/2004 | DeNuzzio et al. |
| 2004/0069164 A1 | 4/2004 | Nakamura et al. |
| 2004/0072357 A1 | 4/2004 | Stiene et al. |
| 2004/0073095 A1 | 4/2004 | Causey, III et al. |
| 2004/0096959 A1 | 5/2004 | Stiene et al. |
| 2004/0100376 A1 | 5/2004 | Lye et al. |
| 2004/0105411 A1 | 6/2004 | Boatwright et al. |
| 2004/0106858 A1 | 6/2004 | Say et al. |
| 2004/0106859 A1 | 6/2004 | Say et al. |
| 2004/0108226 A1 | 6/2004 | Polychronakos et al. |
| 2004/0116786 A1 | 6/2004 | Iijima et al. |
| 2004/0122353 A1 | 6/2004 | Shahmirian et al. |
| 2004/0122489 A1 | 6/2004 | Mazar et al. |
| 2004/0122530 A1 | 6/2004 | Hansen et al. |
| 2004/0133164 A1 | 7/2004 | Funderburk et al. |
| 2004/0133390 A1 | 7/2004 | Osorio et al. |
| 2004/0136377 A1 | 7/2004 | Miyazaki et al. |
| 2004/0138588 A1 | 7/2004 | Saikley et al. |
| 2004/0146909 A1 | 7/2004 | Duong et al. |
| 2004/0147872 A1 | 7/2004 | Thompson |
| 2004/0152622 A1 | 8/2004 | Keith et al. |
| 2004/0152961 A1 | 8/2004 | Carlson et al. |
| 2004/0153585 A1 | 8/2004 | Kawatahara et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0172284 A1 | 9/2004 | Sullivan et al. |
| 2004/0176672 A1 | 9/2004 | Silver et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0202576 A1 | 10/2004 | Aceti et al. |
| 2004/0204687 A1 | 10/2004 | Mogensen et al. |
| 2004/0204868 A1 | 10/2004 | Maynard et al. |
| 2004/0206916 A1 | 10/2004 | Colvin, Jr. et al. |
| 2004/0208780 A1 | 10/2004 | Faries, Jr. et al. |
| 2004/0212536 A1 | 10/2004 | Mori et al. |
| 2004/0221057 A1 | 11/2004 | Darcey et al. |
| 2004/0225199 A1 | 11/2004 | Evanyk et al. |
| 2004/0225338 A1 | 11/2004 | Lebel et al. |
| 2004/0235446 A1 | 11/2004 | Flaherty et al. |

(56) References Cited

U.S. PATENT DOCUMENTS

| | | |
|---|---|---|
| 2004/0236200 A1 | 11/2004 | Say et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254433 A1 | 12/2004 | Bandis et al. |
| 2004/0254434 A1 | 12/2004 | Goodnow et al. |
| 2004/0260363 A1 | 12/2004 | Arx et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0017864 A1 | 1/2005 | Tsoukalis |
| 2005/0027177 A1 | 2/2005 | Shin et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0049179 A1 | 3/2005 | Davidson et al. |
| 2005/0049473 A1 | 3/2005 | Desai et al. |
| 2005/0054909 A1 | 3/2005 | Petisce et al. |
| 2005/0059372 A1 | 3/2005 | Arayashiki et al. |
| 2005/0065464 A1 | 3/2005 | Talbot et al. |
| 2005/0070777 A1 | 3/2005 | Cho et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0112169 A1 | 5/2005 | Brauker et al. |
| 2005/0112544 A1 | 5/2005 | Xu et al. |
| 2005/0113648 A1 | 5/2005 | Yang et al. |
| 2005/0113653 A1 | 5/2005 | Fox et al. |
| 2005/0113657 A1 | 5/2005 | Alarcon et al. |
| 2005/0113658 A1 | 5/2005 | Jacobson et al. |
| 2005/0113886 A1 | 5/2005 | Fischell et al. |
| 2005/0114068 A1 | 5/2005 | Chey et al. |
| 2005/0116683 A1 | 6/2005 | Cheng et al. |
| 2005/0118726 A1 | 6/2005 | Schultz et al. |
| 2005/0121322 A1 | 6/2005 | Say et al. |
| 2005/0124873 A1 | 6/2005 | Shults et al. |
| 2005/0131346 A1 | 6/2005 | Douglas |
| 2005/0137471 A1 | 6/2005 | Haar et al. |
| 2005/0137530 A1 | 6/2005 | Campbell et al. |
| 2005/0143635 A1 | 6/2005 | Kamath et al. |
| 2005/0143636 A1 | 6/2005 | Zhang et al. |
| 2005/0148003 A1 | 7/2005 | Kieth et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0177398 A1 | 8/2005 | Watanabe et al. |
| 2005/0181012 A1 | 8/2005 | Saint et al. |
| 2005/0182306 A1 | 8/2005 | Sloan |
| 2005/0182358 A1 | 8/2005 | Veit et al. |
| 2005/0182451 A1 | 8/2005 | Griffin et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203707 A1 | 9/2005 | Tsutsui et al. |
| 2005/0204134 A1 | 9/2005 | Von Arx et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0221504 A1 | 10/2005 | Petruno et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0242479 A1 | 11/2005 | Petisce et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0251083 A1 | 11/2005 | Carr-Brendel et al. |
| 2005/0261660 A1 | 11/2005 | Choi |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004270 A1 | 1/2006 | Bedard et al. |
| 2006/0004271 A1 | 1/2006 | Peyser et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0052679 A1 | 3/2006 | Kotulla et al. |
| 2006/0058588 A1 | 3/2006 | Zdeblick |
| 2006/0058602 A1 | 3/2006 | Kwiatkowski et al. |
| 2006/0063218 A1 | 3/2006 | Bartkowiak et al. |
| 2006/0074564 A1 | 4/2006 | Bartowiak et al. |
| 2006/0129733 A1 | 6/2006 | Solbelman |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189863 A1 | 8/2006 | Peyser et al. |
| 2006/0193375 A1 | 8/2006 | Lee et al. |

(56) References Cited

U.S. PATENT DOCUMENTS

| | | |
|---|---|---|
| 2006/0195029 A1 | 8/2006 | Shults et al. |
| 2006/0200112 A1 | 9/2006 | Paul |
| 2006/0202805 A1 | 9/2006 | Schulman et al. |
| 2006/0202859 A1 | 9/2006 | Mastrototaro et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247710 A1 | 11/2006 | Goetz et al. |
| 2006/0247985 A1 | 11/2006 | Liamos et al. |
| 2006/0253296 A1 | 11/2006 | Liisberg et al. |
| 2006/0258918 A1 | 11/2006 | Burd et al. |
| 2006/0258929 A1 | 11/2006 | Goode, Jr. et al. |
| 2006/0263763 A1 | 11/2006 | Simpson et al. |
| 2006/0264785 A1 | 11/2006 | Dring et al. |
| 2006/0264888 A1 | 11/2006 | Moberg et al. |
| 2006/0270922 A1 | 11/2006 | Brauker et al. |
| 2006/0272652 A1 | 12/2006 | Stocker et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0007133 A1 | 1/2007 | Mang et al. |
| 2007/0016381 A1 | 1/2007 | Kamath et al. |
| 2007/0017983 A1 | 1/2007 | Frank et al. |
| 2007/0026440 A1 | 2/2007 | Broderick et al. |
| 2007/0027381 A1 | 2/2007 | Stafford |
| 2007/0027507 A1 | 2/2007 | Burdett et al. |
| 2007/0032706 A1 | 2/2007 | Kamath et al. |
| 2007/0033074 A1 | 2/2007 | Nitzan et al. |
| 2007/0038044 A1 | 2/2007 | Dobbles et al. |
| 2007/0053341 A1 | 3/2007 | Lizzi |
| 2007/0055799 A1 | 3/2007 | Koehler et al. |
| 2007/0060814 A1 | 3/2007 | Stafford |
| 2007/0060869 A1 | 3/2007 | Tolle et al. |
| 2007/0066873 A1 | 3/2007 | Kamath et al. |
| 2007/0066877 A1 | 3/2007 | Arnold et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0090511 A1 | 4/2007 | Borland et al. |
| 2007/0093786 A1 | 4/2007 | Goldsmith et al. |
| 2007/0100222 A1 | 5/2007 | Mastrototaro et al. |
| 2007/0106135 A1 | 5/2007 | Sloan et al. |
| 2007/0124002 A1 | 5/2007 | Estes et al. |
| 2007/0135697 A1 | 6/2007 | Reggiardo |
| 2007/0149873 A1 | 6/2007 | Say et al. |
| 2007/0149874 A1 | 6/2007 | Say et al. |
| 2007/0149875 A1 | 6/2007 | Ouyang et al. |
| 2007/0151869 A1 | 7/2007 | Heller et al. |
| 2007/0153705 A1 | 7/2007 | Rosar et al. |
| 2007/0156033 A1 | 7/2007 | Causey, III et al. |
| 2007/0156094 A1 | 7/2007 | Safabash et al. |
| 2007/0161879 A1 | 7/2007 | Say et al. |
| 2007/0161880 A1 | 7/2007 | Say et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173712 A1 | 7/2007 | Shah et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179370 A1 | 8/2007 | Say et al. |
| 2007/0179372 A1 | 8/2007 | Say et al. |
| 2007/0191699 A1 | 8/2007 | Say et al. |
| 2007/0191700 A1 | 8/2007 | Say et al. |
| 2007/0191701 A1 | 8/2007 | Feldman et al. |
| 2007/0191702 A1 | 8/2007 | Yodfat et al. |
| 2007/0203407 A1 | 8/2007 | Hoss et al. |
| 2007/0203408 A1 | 8/2007 | Say et al. |
| 2007/0203410 A1 | 8/2007 | Say et al. |
| 2007/0203411 A1 | 8/2007 | Say et al. |
| 2007/0203966 A1 | 8/2007 | Brauker et al. |
| 2007/0208245 A1 | 9/2007 | Brauker et al. |
| 2007/0208247 A1 | 9/2007 | Say et al. |
| 2007/0213610 A1 | 9/2007 | Say et al. |
| 2007/0213657 A1 | 9/2007 | Jennewine et al. |
| 2007/0215491 A1 | 9/2007 | Heller et al. |
| 2007/0218097 A1 | 9/2007 | Heller et al. |
| 2007/0219496 A1 | 9/2007 | Kamen et al. |
| 2007/0222609 A1 | 9/2007 | Duron et al. |
| 2007/0232877 A1 | 10/2007 | He |
| 2007/0232880 A1 | 10/2007 | Siddiqui et al. |
| 2007/0235331 A1 | 10/2007 | Simpson et al. |
| 2007/0244380 A1 | 10/2007 | Say et al. |
| 2007/0244383 A1 | 10/2007 | Talbot et al. |
| 2007/0249919 A1 | 10/2007 | Say et al. |
| 2007/0249920 A1 | 10/2007 | Say et al. |
| 2007/0249922 A1 | 10/2007 | Peyser et al. |
| 2007/0253021 A1 | 11/2007 | Mehta et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0271285 A1 | 11/2007 | Eichorn et al. |
| 2007/0285238 A1 | 12/2007 | Batra |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009304 A1 | 1/2008 | Fry |
| 2008/0009692 A1 | 1/2008 | Stafford |
| 2008/0017522 A1 | 1/2008 | Heller et al. |
| 2008/0018433 A1 | 1/2008 | Pitt-Pladdy |
| 2008/0021666 A1 | 1/2008 | Goode, Jr. et al. |
| 2008/0027586 A1 | 1/2008 | Hern et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0055070 A1 | 3/2008 | Bange et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0060955 A1 | 3/2008 | Goodnow |
| 2008/0062055 A1 | 3/2008 | Cunningham et al. |
| 2008/0064937 A1 | 3/2008 | McGarraugh et al. |
| 2008/0064943 A1 | 3/2008 | Talbot et al. |
| 2008/0067627 A1 | 3/2008 | Boeck et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0108942 A1 | 5/2008 | Brister et al. |
| 2008/0119705 A1 | 5/2008 | Patel et al. |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0179187 A1 | 7/2008 | Ouyang et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |

(56) References Cited

U.S. PATENT DOCUMENTS

| | | |
|---|---|---|
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208113 A1 | 8/2008 | Damiano et al. |
| 2008/0212600 A1 | 9/2008 | Yoo |
| 2008/0214900 A1 | 9/2008 | Fennell et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234943 A1 | 9/2008 | Ray et al. |
| 2008/0235469 A1 | 9/2008 | Drew |
| 2008/0242961 A1 | 10/2008 | Brister et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0275313 A1 | 11/2008 | Brister et al. |
| 2008/0278331 A1 | 11/2008 | Hayter et al. |
| 2008/0278332 A1 | 11/2008 | Fennell et al. |
| 2008/0278333 A1 | 11/2008 | Fennell et al. |
| 2008/0281171 A1 | 11/2008 | Fennell et al. |
| 2008/0281179 A1 | 11/2008 | Fennell et al. |
| 2008/0281840 A1 | 11/2008 | Fennell et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0296155 A1 | 12/2008 | Shults et al. |
| 2008/0300919 A1 | 12/2008 | Charlton et al. |
| 2008/0300920 A1 | 12/2008 | Brown et al. |
| 2008/0301158 A1 | 12/2008 | Brown et al. |
| 2008/0301436 A1 | 12/2008 | Yao et al. |
| 2008/0301665 A1 | 12/2008 | Charlton et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0319295 A1 | 12/2008 | Bernstein et al. |
| 2008/0319296 A1 | 12/2008 | Bernstein et al. |
| 2008/0320587 A1 | 12/2008 | Vauclair et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054747 A1 | 2/2009 | Fennell |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076359 A1 | 3/2009 | Peyser et al. |
| 2009/0076360 A1 | 3/2009 | Brister et al. |
| 2009/0076361 A1 | 3/2009 | Kamath et al. |
| 2009/0085768 A1 | 4/2009 | Patel et al. |
| 2009/0085873 A1 | 4/2009 | Betts et al. |
| 2009/0093687 A1 | 4/2009 | Telfort et al. |
| 2009/0094680 A1 | 4/2009 | Gupta et al. |
| 2009/0099436 A1 | 4/2009 | Brister et al. |
| 2009/0105554 A1 | 4/2009 | Stahmann et al. |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0146826 A1 | 6/2009 | Gofman et al. |
| 2009/0149717 A1 | 6/2009 | Brauer et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204340 A1 | 8/2009 | Feldman et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0234200 A1 | 9/2009 | Husheer |
| 2009/0237216 A1 | 9/2009 | Twitchell, Jr. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247931 A1 | 10/2009 | Damgaard-Sorensen |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0296742 A1 | 12/2009 | Sicurello et al. |
| 2009/0298182 A1 | 12/2009 | Schulat et al. |
| 2009/0299155 A1 | 12/2009 | Yang et al. |

(56) References Cited

U.S. PATENT DOCUMENTS

| | | |
|---|---|---|
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2009/0318792 A1 | 12/2009 | Fennell et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0025238 A1 | 2/2010 | Gottlieb et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0198034 A1 | 2/2010 | Thomas et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0110931 A1 | 5/2010 | Shim et al. |
| 2010/0119693 A1 | 5/2010 | Tapsak et al. |
| 2010/0119881 A1 | 5/2010 | Patel et al. |
| 2010/0121169 A1 | 5/2010 | Petisce et al. |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168545 A1 | 7/2010 | Kamath et al. |
| 2010/0174266 A1 | 7/2010 | Estes |
| 2010/0185175 A1 | 7/2010 | Kamen et al. |
| 2010/0190435 A1 | 7/2010 | Cook et al. |
| 2010/0191085 A1 | 7/2010 | Budiman |
| 2010/0198142 A1 | 8/2010 | Sloan et al. |
| 2010/0213080 A1 | 8/2010 | Celentano et al. |
| 2010/0235439 A1 | 9/2010 | Goodnow et al. |
| 2010/0267161 A1 | 10/2010 | Wu et al. |
| 2010/0275108 A1 | 10/2010 | Sloan et al. |
| 2010/0277342 A1 | 11/2010 | Sicurello et al. |
| 2010/0312176 A1 | 12/2010 | Lauer et al. |
| 2010/0313105 A1 | 12/2010 | Nekoomaram et al. |
| 2010/0324403 A1 | 12/2010 | Brister et al. |
| 2010/0331646 A1 | 12/2010 | Hoss et al. |
| 2010/0332142 A1 | 12/2010 | Shadforth et al. |
| 2011/0004276 A1 | 1/2011 | Blair et al. |
| 2011/0031986 A1 | 2/2011 | Bhat et al. |
| 2011/0054282 A1 | 3/2011 | Nekoomaram et al. |
| 2011/0060530 A1 | 3/2011 | Fennell |
| 2011/0074349 A1 | 3/2011 | Ghovanloo |
| 2011/0125040 A1 | 5/2011 | Crawford et al. |
| 2011/0148905 A1 | 6/2011 | Simmons et al. |
| 2011/0152637 A1 | 6/2011 | Kateraas et al. |
| 2011/0184268 A1 | 7/2011 | Taub |
| 2011/0191059 A1* | 8/2011 | Farrell et al. ............ 702/130 |
| 2011/0193704 A1 | 8/2011 | Harper et al. |
| 2011/0213225 A1 | 9/2011 | Bernstein et al. |
| 2011/0230741 A1 | 9/2011 | Liang et al. |
| 2011/0257895 A1 | 10/2011 | Brauker et al. |
| 2011/0270112 A1 | 11/2011 | Manera et al. |
| 2011/0287528 A1 | 11/2011 | Fern et al. |
| 2012/0108931 A1 | 5/2012 | Taub et al. |
| 2012/0148054 A1 | 6/2012 | Rank et al. |
| 2012/0190989 A1 | 7/2012 | Kaiser et al. |
| 2012/0215092 A1 | 8/2012 | Harris, III et al. |
| 2013/0035575 A1 | 2/2013 | Mayou et al. |
| 2013/0235166 A1 | 9/2013 | Jones et al. |

FOREIGN PATENT DOCUMENTS

| | | |
|---|---|---|
| EP | 0010375 | 4/1980 |
| EP | 0026995 | 4/1981 |
| EP | 0048090 | 3/1982 |
| EP | 0078636 | 5/1983 |
| EP | 0080304 | 6/1983 |
| EP | 0098592 | 1/1984 |
| EP | 0125139 | 11/1984 |
| EP | 0127958 | 12/1984 |
| EP | 0136362 | 4/1985 |
| EP | 0170375 | 2/1986 |
| EP | 0177743 | 4/1986 |
| EP | 0184909 | 6/1986 |
| EP | 0206218 | 12/1986 |
| EP | 0230472 | 8/1987 |
| EP | 0241309 | 10/1987 |
| EP | 0245073 | 11/1987 |
| EP | 0255291 | 2/1988 |
| EP | 0278647 | 8/1988 |
| EP | 0320109 | 6/1989 |
| EP | 0353328 | 2/1990 |
| EP | 0359831 | 3/1990 |
| EP | 0368209 | 5/1990 |
| EP | 0390390 | 10/1990 |
| EP | 0396788 | 11/1990 |
| EP | 0400918 | 12/1990 |
| EP | 0453283 | 10/1991 |
| EP | 0470290 | 2/1992 |
| EP | 0504835 | 9/1992 |
| EP | 0286118 | 1/1995 |
| EP | 0653718 | 5/1995 |
| EP | 0680727 | 11/1995 |
| EP | 0724859 | 8/1996 |
| EP | 0800082 | 10/1997 |
| EP | 0805574 | 11/1997 |
| EP | 0880936 | 12/1998 |
| EP | 0970655 | 1/2000 |
| EP | 0973289 | 1/2000 |
| EP | 0678308 | 5/2000 |
| EP | 1034734 | 9/2000 |
| EP | 1048264 | 11/2000 |
| EP | 1579690 | 11/2002 |
| EP | 1292218 | 3/2003 |
| EP | 1077634 | 7/2003 |
| EP | 1445746 | 8/2004 |
| EP | 1568309 | 8/2005 |
| EP | 1666091 | 6/2006 |
| EP | 1703697 | 9/2006 |
| EP | 1704893 | 9/2006 |
| EP | 1897487 | 11/2009 |
| EP | 1897492 | 11/2009 |
| EP | 2113864 | 11/2009 |
| EP | 1897488 | 12/2009 |
| EP | 1681992 | 4/2010 |
| EP | 1448489 | 8/2010 |
| EP | 1971396 | 8/2010 |
| EP | 2201969 | 3/2011 |
| EP | 1413245 | 6/2011 |
| EP | 2153382 | 2/2012 |
| EP | 2284773 | 2/2012 |
| GB | 1394171 | 5/1975 |
| GB | 1579690 | 11/1980 |
| GB | 1599241 | 9/1981 |
| GB | 2073891 | 10/1981 |
| GB | 2154003 | 8/1985 |
| GB | 2194892 | 3/1988 |
| GB | 2204408 | 11/1988 |
| GB | 2225637 | 6/1990 |

(56) References Cited

FOREIGN PATENT DOCUMENTS

| | | |
|---|---|---|
| GB | 2254436 | 10/1992 |
| GB | 2409951 | 7/2005 |
| SU | 1281988 | 1/1987 |
| WO | WO-1985/005119 | 11/1985 |
| WO | WO-1986/000513 | 1/1986 |
| WO | WO-1987/000513 | 1/1987 |
| WO | WO-1987/006040 | 10/1987 |
| WO | WO-1989/002246 | 3/1989 |
| WO | WO-1989/005119 | 6/1989 |
| WO | WO-1989/008713 | 9/1989 |
| WO | WO-1990/000367 | 1/1990 |
| WO | WO-1990/005300 | 5/1990 |
| WO | WO-1990/005910 | 5/1990 |
| WO | WO-1991/001680 | 2/1991 |
| WO | WO-1991/004704 | 4/1991 |
| WO | WO-1991/015993 | 10/1991 |
| WO | WO-1992/001947 | 2/1992 |
| WO | WO-1992/013271 | 8/1992 |
| WO | WO-1994/020602 | 9/1994 |
| WO | WO-1994/027140 | 11/1994 |
| WO | WO-1995/028878 | 2/1995 |
| WO | WO-1995/006240 | 3/1995 |
| WO | WO-1996/007908 | 3/1996 |
| WO | WO-1996/025089 | 8/1996 |
| WO | WO-1996/030431 | 10/1996 |
| WO | WO-1996/035370 | 11/1996 |
| WO | WO-1997/002847 | 1/1997 |
| WO | WO-1997/019344 | 5/1997 |
| WO | WO-1997/020207 | 6/1997 |
| WO | WO-1997/033513 | 9/1997 |
| WO | WO-1997/041421 | 11/1997 |
| WO | WO-1997/042882 | 11/1997 |
| WO | WO-1997/042883 | 11/1997 |
| WO | WO-1997/042886 | 11/1997 |
| WO | WO-1997/042888 | 11/1997 |
| WO | WO-1997/043962 | 11/1997 |
| WO | WO-1997/046868 | 12/1997 |
| WO | WO-1998/009167 | 3/1998 |
| WO | WO-1998/024366 | 6/1998 |
| WO | WO-1998/035053 | 8/1998 |
| WO | WO-1998/052045 | 11/1998 |
| WO | WO-1998/052293 | 11/1998 |
| WO | WO-1999/005966 | 2/1999 |
| WO | WO-1999/032883 | 7/1999 |
| WO | WO-1999/056613 | 11/1999 |
| WO | WO-2000/013580 | 3/2000 |
| WO | WO-2000/018294 | 4/2000 |
| WO | WO-2000/019887 | 4/2000 |
| WO | WO-2000/020626 | 4/2000 |
| WO | WO-2000/033065 | 6/2000 |
| WO | WO-2000/049940 | 8/2000 |
| WO | WO-2000/059370 | 10/2000 |
| WO | WO-2000/060350 | 10/2000 |
| WO | WO-2000/062664 | 10/2000 |
| WO | WO-2000/062665 | 10/2000 |
| WO | WO-2000/074753 | 12/2000 |
| WO | WO-2000/078210 | 12/2000 |
| WO | WO-2000/078992 | 12/2000 |
| WO | WO-2001/024038 | 4/2001 |
| WO | WO-2001/033216 | 5/2001 |
| WO | WO-2001/052727 | 7/2001 |
| WO | WO-2001/052935 | 7/2001 |
| WO | WO-2001/054753 | 8/2001 |
| WO | WO-2001/057238 | 8/2001 |
| WO | WO-2001/057239 | 8/2001 |
| WO | WO-2001/067009 | 9/2001 |
| WO | WO-2002/013686 | 2/2002 |
| WO | WO-2002/016905 | 2/2002 |
| WO | WO-2002/017210 | 2/2002 |
| WO | WO-2002/058537 | 8/2002 |
| WO | WO-2002/078512 | 10/2002 |
| WO | WO-2003/036583 | 5/2003 |
| WO | WO-2003/076893 | 9/2003 |
| WO | WO-2003/082091 | 10/2003 |
| WO | WO-2003/085372 | 10/2003 |
| WO | WO-2004/047445 | 6/2004 |
| WO | WO-2004/061420 | 7/2004 |
| WO | WO-2004/098405 | 11/2004 |
| WO | WO-2005/010756 | 2/2005 |
| WO | WO-2005/041766 | 5/2005 |
| WO | WO-2005/045744 | 5/2005 |
| WO | WO-2005/089103 | 9/2005 |
| WO | WO-2005/117269 | 12/2005 |
| WO | WO-2006/024671 | 3/2006 |
| WO | WO-2006/032653 | 3/2006 |
| WO | WO-2006/037109 | 4/2006 |
| WO | WO-2006/064397 | 6/2006 |
| WO | WO-2006/079114 | 7/2006 |
| WO | WO-2006/118947 | 11/2006 |
| WO | WO-2006/119084 | 11/2006 |
| WO | WO-2006/124099 | 11/2006 |
| WO | WO-2007/002189 | 1/2007 |
| WO | WO-2007/007459 | 1/2007 |
| WO | WO-2007/027381 | 3/2007 |
| WO | WO-2008/086541 | 7/2008 |
| WO | WO-2008/150428 | 12/2008 |
| WO | WO-2008/153825 | 12/2008 |
| WO | WO-2009/075697 | 6/2009 |
| WO | WO-2010/077329 | 8/2010 |
| WO | WO-2011/022418 | 2/2011 |

OTHER PUBLICATIONS

Albery, W. J., et al., "Amperometric Enzyme Electrodes Part II: Conducting Salts as Electrode Materials for the Oxidation of Glucose Oxidase", *Journal of ElectroAnalytical Chemistry*, vol. 194, 1985, pp. 223-235.

Albery, W. J., et al., "Amperometric Enzyme Electrodes", *Philosophical Transactions of the Royal Society of London*, vol. 316, 1987, pp. 107-119.

Alcock, S. J., et al., "Continuous Analyte Monitoring to Aid Clinical Practice", *IEEE Engineering in Medicine and Biology Magazine*, 1994, pp. 319-325.

Anderson, L. B., et al., "Thin-Layer Electrochemistry: Steady-State Methods of Studying Rate Processes", *Journal of ElectroAnalytical Chemistry*, vol. 10, 1965, pp. 295-305.

Armour, J. C., et al., "Application of Chronic Intravascular Blood Glucose Sensor in Dogs", *Diabetes*, vol. 39, 1990, pp. 1519-1526.

Bartlett, P. N., et al., "Covalent Binding of Electron Relays to Glucose Oxidase", Journal of.The Chemical Society, Chemical Communications, 1987, pp. 1603-1604.

Bartlett, P. N., et al., "Modification of Glucose Oxidase by Tetrathiafulvalene", *Journal of the Chemical Society, Chemical Communications*, 1990, pp. 1135-1136.

Bartlett, P. N., et al., "Strategies for the Development of Amperometric Enzyme Electrodes", *Biosensors*, vol. 3, 1987/88, pp. 359-379.

Bennion, N., et al., "Alternate Site Glucose Testing: A Crossover Design", *Diabetes Technology & Therapeutics*, vol. 4, No. 1, 2002, pp. 25-33.

Bindra, D. S., et al., "Design and in Vitro Studies of a Needle-Type Glucose Sensor for Subcutaneous Monitoring", *Analytical Chemistry*, vol. 63 No. 17, 1991, pp. 1692-1696.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.

Boedeker Plastics, Inc., "Polyethylene Specifications", *Web Page of Boedeker.com*, 2007, pp. 1-3.

Brandt, J., et al., "Covalent Attachment of Proteins to Polysaccharide Carriers by Means of Benzoquinone", *Biochimica et Biophysica Acta*, vol. 386, 1975, pp. 196-202.

Brooks, S. L., et al., "Development of an On-Line Glucose Sensor for Fermentation Monitoring", *Biosensors*, vol. 3, 1987/88, pp. 45-56.

(56) References Cited

OTHER PUBLICATIONS

Brownlee, M., et al., "A Glucose-Controlled Insulin-Delivery System: Semisynthetic Insulin Bound to Lectin", *Science*, vol. 206, 1979, 1190-1191.

Cass, A. E., et al., "Ferricinum Ion As an Electron Acceptor for Oxido-Reductases", *Journal of ElectroAnalytical Chemistry*, vol. 190, 1985, pp. 117-127.

Cass, A. E., et al., "Ferrocene-Medicated Enzyme Electrode for Amperometric Determination of Glucose", *Analytical Chemistry*, vol. 56, No. 4, 1984, 667-671.

Castner, J. F., et al., "Mass Transport and Reaction Kinetic Parameters Determined Electrochemically for Immobilized Glucose Oxidase", *Biochemistry*, vol. 23 No. 10, 1984, 2203-2210.

Claremont, D. J., et al., "Biosensors for Continuous In Vivo Glucose Monitoring", *Proceedings of the Annual International Conference of the IEEE Engineering in Medicine and Biology Society*, vol. 10, 1988.

Clark Jr., L. C., et al., "Differential Anodic Enzyme Polarography for the Measurement of Glucose", *Oxygen Transport to Tissue: Instrumentation, Methods, and Physiology*, 1973, pp. 127-133.

Clark Jr., L. C., et al., "Electrode Systems for Continuous Monitoring in Cardiovascular Surgery", *Annals New York Academy of Sciences*, 1962, pp. 29-45.

Clark Jr., L. C., et al., "Long-term Stability of Electroenzymatic Glucose Sensors Implanted in Mice", *American Society of Artificial Internal Organs Transactions*, vol. XXXIV, 1988, pp. 259-265.

Clarke, W. L., et al., "Evaluating Clinical Accuracy of Systems for Self-Monitoring of Blood Glucose", *Diabetes Care*, vol. 10, No. 5, 1987, pp. 622-628.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.

Csoregi, E., et al., "On-Line Glucose Monitoring by Using Microdialysis Sampling and Amperometric Detection Based on 'Wired' Glucose Oxidase in Carbon Paste", *Mikrochimica Acta*, vol. 121, 1995, pp. 31-40.

Dai, W. S., et al., "Hydrogel Membranes with Mesh Size Asymmetry Based on the Gradient Crosslinking of Poly(vinyl alcohol),", *Journal of Membrane Science*, vol. 156, 1999, pp. 67-79.

Davis, G., "Electrochemical Techniques for the Development of Amperometric Biosensors", *Biosensors*, vol. 1, 1985, pp. 161-178.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry*, vol. 91, No. 6, 1987, pp. 1285-1289.

Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", *Journal of the American Chemical Society*, vol. 110, No. 8, 1988, pp. 2615-2620.

Degani, Y., et al., "Electrical Communication Between Redox Centers of Glucose Oxidase and Electrodes via Electrostatically and Covalently Bound Redox Polymers", *Journal of the American Chemical Society*, vol. 111, 1989, pp. 2357-2358.

Denisevich, P., et al., "Unidirectional Current Flow and Charge State Trapping at Redox Polymer Interfaces on Bilayer Electrodes: Principles, Experimental Demonstration, and Theory", *Journal of the American Chemical Society*, vol. 103, 1981, pp. 4727-4737.

Dicks, J. M., et al., "Ferrocene Modified Polypyrrole with Immobilised Glucose Oxidase and its Application in Amperometric Glucose Microbiosensors", *Annales de Biologie Clinique*, vol. 47, 1989, pp. 607-619.

Diem, P., et al., "Clinical Performance of a Continuous Viscometric Affinity Sensor for Glucose", *Diabetes Technology & Therapeutics*, vol. 6, 2004, pp. 790-799.

Ellis, C. D., et al., "Selectivity and Directed Charge Transfer through an Electroactive Metallopolymer Film", *Journal of the American Chemical Society*, vol. 103, No. 25, 1981, pp. 7480-7483.

Engstrom, R. C., "Electrochemical Pretreatment of Glassy Carbon Electrodes", *Analytical Chemistry*, vol. 54, No. 13, 1982, pp. 2310-2314.

Engstrom, R. C., et al., "Characterization of Electrochemically Pretreated Glassy Carbon Electrodes", *Analytical Chemistry*, vol. 56, No. 2, 1984, pp. 136-141.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Feldman, B., et al., "Electron Transfer Kinetics at Redox Polymer/Solution Interfaces Using Microelectrodes and Twin Electrode Thin Layer Cells", *Journal of ElectroAnalytical Chemistry*, vol. 194, 1985, pp. 63-81.

Fischer, H., et al., "Intramolecular Electron Transfer Medicated by 4,4'-Bypyridine and Related Bridging Groups", *Journal of the American Chemical Society*, vol. 98, No. 18, 1976, pp. 5512-5517.

Flentge, F., et al., "An Enzyme-Reactor for Electrochemical Monitoring of Choline and Acetylcholine: Applications in High-Performance Liquid Chromatography, Bran Tissue, Microdialysis and Cerebrospinal Fluid," *Analytical Biochemistry*, vol. 204, 1992, pp. 305-310.

Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions 1*, vol. 82, 1986, pp. 1259-1264.

Foulds, N. C., et al., "Immobilization of Glucose Oxidase in Ferrocene-Modified Pyrrole Polymers", *Analytical Chemistry*, vol. 60, No. 22, 1988, pp. 2473-2478.

Frew, J. E., et al., "Electron-Transfer Biosensors", *Philosophical Transactions of the Royal Society of London*, vol. 316, 1987, pp. 95-106.

Garg, S., et al., "Improvement in Glycemic Excursions with a Transcutaneous, Real-Time Continuous Glucose Sensor", *Diabetes Care*, vol. 29, No. 1, 2006, pp. 44-50.

Godsland, I. F., et al., "Maximizing the Success Rate of Minimal Model Insulin Sensitivity Measurement in Humans: The Importance of Basal Glucose Levels," *Clinical Science*, vol. 101, 2001, pp. 1-9.

Gorton, L., et al., "Selective Detection in Flow Analysis Based on the Combination of Immobilized Enzymes and Chemically Modified Electrodes", *Analytica Chimica Acta*, vol. 250, 1991, pp. 203-248.

Graham, N. B., "Poly(ethylene oxide) and Related Hydrogels," *Hydrogels in Medicine and Pharmacy*, vol. II: Polymers, Chapter 4, 1987, pp. 95-113.

Gregg, B. A., et al., "Cross-Linked Redox Gels Containing Glucose Oxidase for Amperometric Bionsensor Applications", *Analytical Chemistry*, vol. 62, No. 3, 1990, pp. 258-263.

Gregg, B. A., et al., "Redox Polymer Films Containing Enzymes. 1. A Redox-Conducting Epoxy Cement: Synthesis, Characterization, and Electrocatalytic Oxidation of Hydroquinone", *Journal of Physical Chemistry*, vol. 95, No. 15, 1991, 5970-5975.

Hale, P. D., et al., "A New Class of Amperometric Biosensor Incorporating a Polymeric Electron-Transfer Mediator", *Journal of the American Chemical Society*, vol. 111, No. 9, 1989, pp. 3482-3484.

Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.

Hawkridge, F. M., et al., "Indirect Coulometric Titration of Biological Electron Transport Components", *Analytical Chemistry*, vol. 45, No. 7, 1973, pp. 1021-1027.

(56) References Cited

OTHER PUBLICATIONS

Heller, A., "Electrical Connection Enzyme Redox Centers to Electrodes", *Journal of Physical Chemistry*, vol. 96, No. 9, 1990, pp. 3579-3587.
Heller, A., "Electrical Wiring of Redox Enzymes", *Accounts of Chemical Research* vol. 23, No. 5, 1990, 128-134.
Heller, A., et al., "Amperometric Biosensors Based on Three-Dimensional Hydrogel-Forming Epoxy Networks", *Sensors and Actuators B*, vol. 13-14, 1993, pp. 180-183.
Ianniello, R. M., et al., "Differential Pulse Voltammetric Study of Direct Electron Transfer in Glucose Oxidase Chemically Modified Graphite Electrodes", *Analytical Chemistry*, vol. 54, No. 7, 1982, pp. 1098-1101.
Ianniello, R. M., et al., "Immobilized Enzyme Chemically Modified Electrode as an Amperometric Sensor", *Analytical Chemistry*, vol. 53, No. 13, 1981, pp. 2090-2095.
Ikeda, T., et al., "Glucose Oxidase-Immobilized Benzoquinone-Carbon Paste Electrode as a Glucose Sensor", *Agricultural and Biological Chemistry*, vol. 49, No. 2, 1985, pp. 541-543.
Ikeda, T., et al., "Kinetics of Outer-Sphere Electron Transfers Between Metal Complexes in Solutions and Polymeric Films on Modified Electrodes", *Journal of the American Chemical Society*, vol. 103, No. 25, 1981, pp. 7422-7425.
Isermann, R., "Supervision, Fault-Detection and Fault-Diagnosis Methods—An Introduction", *Control Engineering Practice*, vol. 5, No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Johnson, J. M., et al., "Potential-Dependent Enzymatic Activity in an Enzyme Thin-Layer Cell", *Analytical Chemistry*, vol. 54, No. 8, 1982, pp. 1377-1383.
Johnson, K. W., "Reproducible Electrodeposition of Biomolecules for the Fabrication of Miniature Electroenzymatic Biosensors", *Sensors and Actuators B*, vol. 5, 1991, pp. 85-89.
Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.
Johnson, P. C., "Peripheral Circulation", *John Wiley & Sons*, 1978, pp. 198.
Jonsson, G., et al., "An Amperometric Glucose Sensor Made by Modification of a Graphite Electrode Surface With Immobilized Glucose Oxidase and Adsorbed Mediator", *Biosensors*, vol. 1, 1985, pp. 355-368.
Josowicz, M., et al., "Electrochemical Pretreatment of Thin Film Platinum Electrodes", *Journal of the Electrochemical Society*, vol. 135 No. 1, 1988, pp. 112-115.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", *Diabetes Care*, vol. 24, No. 7, 2001, pp. 1303-1304.
Kaplan, S. M., "Wiley Electrical and Electronics Engineering Dictionary", *IEEE Press*, 2004, pp. 141, 142, 548, 549.
Katakis, I., et al., "Electrostatic Control of the Electron Transfer Enabling Binding of Recombinant Glucose Oxidase and Redox Polyelectrolytes", *Journal of the American Chemical Society*, vol. 116, No. 8, 1994, pp. 3617-3618.
Katakis, I., et al., "L-α-Glycerophosphate and L-Lactate Electrodes Based on the Electrochemical 'Wiring' of Oxidases", *Analytical Chemistry*, vol. 64, No. 9, 1992, pp. 1008-1013.
Kemp, G. J., "Theoretical Aspects of One-Point Calibration: Causes and Effects of Some Potential Errors, and Their Dependence on Concentration," *Clinical Chemistry*, vol. 30, No. 7, 1984, pp. 1163-1167.
Kenausis, G., et al., "'Wiring' of Glucose Oxidase and Lactate Oxidase Within a Hydrogel Made with Poly(vinyl pyridine) complexed with [Os(4,4'-dimethoxy-2,2'-bipyridine)$_2$Cl]$^{+2}$", *Journal of the Chemical Society, Faraday Transactions*, vol. 92, No. 20, 1996, pp. 4131-4136.
Kerner, W., et al., "The Function of a Hydrogen Peroxide-Detecting Electroenzymatic Glucose Electrode is Markedly Impaired in Human Subcutaneous Tissue and Plasma," *Biosensors & Bioelectronics*, vol. 8, 1993, pp. 473-482.
Kondepati, V., et al., "Recent Progress in Analytical Instrumentation for Glycemic Control in Diabetic and Critically Ill Patients", *Analytical Bioanalytical Chemistry*, vol. 388, 2007, pp. 545-563.
Korf, J., et al., "Monitoring of Glucose and Lactate Using Microdialysis: Applications in Neonates and Rat Brain," *Developmental Neuroscience*, vol. 15, 1993, pp. 240-246.
Koudelka, M., et al., "In-Vivo Behaviour of Hypodermically Implanted Microfabricated Glucose Sensors", *Biosensors & Bioelectronics*, vol. 6, 1991, pp. 31-36.
Kulys, J., et al., "Mediatorless Peroxidase Electrode and Preparation of Bienzyme Sensors", *Bioelectrochemistry and Bioenergetics*, vol. 24, 1990, pp. 305-311.
Lager, W., et al., "Implantable Electrocatalytic Glucose Sensor", *Hormone Metabolic Research*, vol. 26, 1994, pp. 526-530.
Laurell, T., "A Continuous Glucose Monitoring System Based on Microdialysis", *Journal of Medical Engineering & Technology*, vol. 16, No. 5, 1992, pp. 187-193.
Lindner, E., et al., "Flexible (Kapton-Based) Microsensor Arrays of High Stability for Cardiovascular Applications", *Journal of the Chemical Society, Faraday Transactions*, vol. 89, No. 2, 1993, pp. 361-367.
Lo, B., et al., "Key Technical Challenges and Current Implementations of Body Sensor Networks", *Body Sensor Networks*, 2005, pp. 1-5.
Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.
Lortz, J., et al., "What is Bluetooth? We Explain the Newest Short-Range Connectivity Technology", *Smart Computing Learning Series, Wireless Computing*, vol. 8, Issue 5, 2002, pp. 72-74.
Maidan, R., et al., "Elimination of Electrooxidizable Interferant-Produced Currents in Amperometric Biosensors", *Analytical Chemistry*, vol. 64, No. 23, 1992, pp. 2889-2896.
Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.
Marko-Varga, G., et al., "Enzyme-Based Biosensor as a Selective Detection Unit in Column Liquid Chromatography", *Journal of Chromatography A*, vol. 660, 1994, pp. 153-167.
Mastrototaro, J. J., et al., "An Electroenzymatic Glucose Sensor Fabricated on a Flexible Substrate", *Sensors and Actuators B*, vol. 5, 1991, pp. 139-144.
Mauras, N., et al., "Lack of Accuracy of Continuous Glucose Sensors in Healthy, Nondiabetic Children: Results of the Diabetes Research in Children Network (DirecNet) Accuracy Study," *Journal of Pediatrics*, 2004, pp. 770-775.
McGarraugh, G., et al., "Glucose Measurements Using Blood Extracted from the Forearm and the Finger", *TheraSense, Inc.*, 2001, 16 Pages.
McGarraugh, G., et al., "Physiological Influences on Off-Finger Glucose Testing", *Diabetes Technology & Therapeutics*, vol. 3, No. 3, 2001, pp. 367-376.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.
McNeil, C. J., et al., "Thermostable Reduced Nicotinamide Adenine Dinucleotide Oxidase: Application to Amperometric Enzyme Assay", *Analytical Chemistry*, vol. 61, No. 1, 1989, pp. 25-29.
Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60-68.

(56) References Cited

OTHER PUBLICATIONS

Moatti-Sirat, D., et al., "Evaluating In Vitro and In Vivo the Interference of Ascorbate and Acetaminophen on Glucose Detection by a Needle-Type Glucose Sensor", *Biosensors & Bioelectronics*, vol. 7, 1992, pp. 345-352.
Moatti-Sirat, D., et al., "Reduction of Acetaminophen Interference in Glucose Sensors by a Composite Nafion Membrane: Demonstration in Rats and Man", *Diabetologia*, vol. 37, 1994, pp. 610-616.
Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.
Morbiducci, U, et al., "Improved Usability of the Minimal Model of Insulin Sensitivity Based on an Automated Approach and Genetic Algorithms for Parameter Estimation", *Clinical Science*, vol. 112 2007, pp. 257-263.
Mougiakakou, et al., "A Real Time Simulation Model of Glucose-Insulin Metabolism for Type 1 Diabetes Patients", *Proceedings of the 2005 IEEE*, 2005, pp. 298-301.
Nagy, G., et al., "A New Type of Enzyme Electrode: The Ascorbic Acid Eliminator Electrode", *Life Sciences*, vol. 31, No. 23, 1982, pp. 2611-2616.
Nakamura, S., et al., "Effect of Periodate Oxidation on the Structure and Properties of Glucose Oxidase", *Biochimica et Biophysica Acta.*, vol. 445, 1976, pp. 294-308.
Narasimham, K., et al., "p-Benzoquinone Activation of Metal Oxide Electrodes for Attachment of Enzymes", *Enzyme and Microbial Technology*, vol. 7, 1985, pp. 283-286.
Ohara, T. J., "Osmium Bipyridyl Redox Polymers Used in Enzyme Electrodes", *Platinum Metals Review*, vol. 39, No. 2, 1995, pp. 54-62.
Ohara, T. J., et al., "'Wired' Enzyme Electrodes for Amperometric Determination of Glucose or Lactate in the Presence of Interfering Substances", *Analytical Chemistry*, vol. 66, No. 15, 1994, pp. 2451-2457.
Ohara, T. J., et al., "Glucose Electrodes Based on Cross-Linked [Os(bpy)$_2$Cl]$^{+/2+}$ Complexed Poly(1-Vinylimidazole) Films", *Analytical Chemistry*, vol. 65, No. 23, 1993, pp. 3512-3517.
Olievier, C. N., et al., "In Vivo Measurement of Carbon Dioxide Tension with a Miniature Electrodes", *Pflugers Archiv: European Journal of Physiology*, vol. 373, 1978, pp. 269-272.
Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487-494.
Palleschi, G., et al., "A Study of Interferences in Glucose Measurements in Blood by Hydrogen Peroxide Based Glucose Probes", *Analytical Biochemistry*, vol. 159, 1986, pp. 114-121.
Pankratov, I., et al., "Sol-Gel Derived Renewable-Surface Biosensors", *Journal of ElectroAnalytical Chemistry*, vol. 393, 1995, pp. 35-41.
Parker, R., et al., "Robust H∞ Glucose Control in Diabetes Using a Physiological Model", *AIChE Journal*, vol. 46, No. 12, 2000, pp. 2537-2549.
Pathak, C., et al., "Rapid Photopolymerization of Immunoprotective Gels in Contact with Cells and Tissue", *Journal of the American Chemical Society*, vol. 114, No. 21, 1992, pp. 8311-8312.
Pickup, J., "Developing Glucose Sensors for In Vivo Use", *Tibtech*, vol. 11, 1993, pp. 285-291.
Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pickup, J., et al., "Potentially-Implantable, Amperometric Glucose Sensors with Mediated Electron Transfer: Improving the Operating Stability", *Biosensors*, vol. 4, 1989, pp. 109-119.

Pishko, M. V., et al., "Amperometric Glucose Microelectrodes Prepared Through Immobilization of Glucose Oxidase in Redox Hydrogels", *Analytical Chemistry*, vol. 63, No. 20, 1 991, pp. 2268-2272.
Poitout, V., et al., "A Glucose Monitoring System for on Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658-663.
Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587-592.
Poitout, V., et al., "In Vitro and In Vivo Evaluation in Dogs of a Miniaturized Glucose Sensor", *ASAIO Transactions*, vol. 37, No. 3, 1991, pp. M298-M300.
Pollak, A., et al., "Enzyme Immobilization by Condensation Copolymerization into Cross-Linked Polyacrylamide Gels", *Journal of the American Chemical Society*, vol. 102, No. 20, 1980, pp. 6324-6336.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Reach, G., et al., "Can Continuous Glucose Monitoring Be Used for the Treatment of Diabetes?", *Analytical Chemistry*, vol. 64, No. 6, 1992, pp. 381-386.
Rebrin, K., et al., "Automated Feedback Control of Subcutaneous Glucose Concentration in Diabetic Dogs", *Diabetologia*, vol. 32, 1989, pp. 573-576.
Reusch, W., "Other Topics: Organometallic Chemistry: Organometallic Compounds: Main Group Organometallic Compounds," *Virtual Textbook of Organic Chemistry*, 1999, Rev. 2007, 25 pages.
Rodriguez, N., et al., "Flexible Communication and Control Protocol for Injectable Neuromuscular Interfaces", IEEE Transactions on Biomedical Circuits and Systems, vol. 1, No. 2007, pp. 19-27.
Roe, J. N., et al., "Bloodless Glucose Measurements", *Critical Review in Therapeutic Drug Carrier Systems*, vol. 15, Issue 3, 1998, pp. 199-241.
Sacks (Ed), "Guidelines and Recommendations for Laboratory Analysis in the Diagnosis and Management of Diabetes Mellitus," *The National Academy of Clinical Biochemistry Presents Laboratory Medicine Practice Guidelines*, vol. 13, 2002, pp. 8-11, 21-23, 52-56, 63.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salditt, P., "Trends in Medical Device Design and Manufacturing", *SMTA News and Journal of Surface Mount Technology*, vol. 17, 2004, pp. 19-24.
Salehi, C., et al., "A Telemetry-Instrumentation System for Long-Term Implantable Glucose and Oxygen Sensors", *Analytical Letters*, vol. 29, No. 13, 1996, pp. 2289-2308.
Samuels, G. J., et al., "An Electrode-Supported Oxidation Catalyst Based on Ruthenium (IV). pH 'Encapsulation' in a Polymer Film", *Journal of the American Chemical Society*, vol. 103, No. 1981, pp. 307-312.
Sasso, S. V., et al., "Electropolymerized 1,2-Diaminobenzene as a Means to Prevent Interferences and Fouling and to Stabilize Immobilized Enzyme in Electrochemical Biosensors", *Analytical Chemistry*, vol. 62 No. 11, 1990, pp. 1111-1117.
Scheller, F. W., et al., "Second Generation Biosensors," *Biosensors & Bioelectronics*, vol. 6, 1991, pp. 245-253.
Scheller, F., et al., "Enzyme Electrodes and Their Application", *Philosophical Transactions of The Royal Society of London B*, vol. 316, 1987, pp. 85-94.
Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97-109.

(56) References Cited

OTHER PUBLICATIONS

Schmidt, F. J., et al., "Calibration of a Wearable Glucose Sensor", *The International Journal of Artificial Organs*, vol. 15, No. 1, 1992, pp. 55-61.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sittampalam, G., et al., "Surface-Modified Electrochemical Detector for Liquid Chromatography", *Analytical Chemistry*, vol. 55, No. 9, 1983, pp. 1608-1610.

Skoog, D. A., et al., "Evaluation of Analytical Data," *Fundamentals of Analytical Chemistry*, 1966, pp. 55.

Soegijoko, S., et al., "External Artificial Pancreas: A New Control Unit Using Microprocessor", *Hormone and Metabolic Research Supplement Series*, vol. 12, 1982, pp. 165-169.

Sprules, S. D., et al., "Evaluation of a New Disposable Screen-Printed Sensor Strip for the Measurement of NADH and Its Modification to Produce a Lactate Biosensor Employing Microliter Volumes", *Electroanalysis*, vol. 8, No. 6, 1996, pp. 539-543.

Sternberg, F., et al., "Calibration Problems of Subcutaneous Glucosensors when Applied 'In-Situ' in Man", *Hormone and Metabolic Research*, vol. 26, 1994, pp. 523-526.

Sternberg, R., et al., "Covalent Enzyme Coupling on Cellulose Acetate Membranes for Glucose Sensor Development", *Analytical Chemistry*, vol. 60, No. 24, 1988, pp. 2781-2786.

Sternberg, R., et al., "Study and Development of Multilayer Needle-Type Enzyme-Based Glucose Microsensors", *Biosensors*, vol. 4, 1988, pp. 27-40.

Suekane, M , "Immobilization of Glucose Isomerase", *Zettschrift fur Allgemeine Mikrobiologie*, vol. 22, No. 8, 1982, pp. 565-576.

Tajima, S., et al., "Simultaneous Determination of Glucose and 1,5-Anydroglucitol", *Chemical Abstracts*, vol. 111, No. 25, 1989, pp. 394.

Takamura, A., et al., Drug release from Poly(vinyl alcohol) Gel Prepared by Freeze-Thaw Procedure, *Journal of Controlled Release*, vol. 20, 1992, pp. 21-27.

Tarasevich, M. R., "Bioelectrocatalysis", *Comprehensive Treatise of Electrochemistry*, vol. 10, 1985, pp. 231-295.

Tatsuma, T., et al., "Enzyme Monolayer—and Bilayer-Modified Tin Oxide Electrodes for the Determination of Hydrogen Peroxide and Glucose", *Analytical Chemistry*, vol. 61, No. 21, 1989, pp. 2352-2355.

Taylor, C., et al., "'Wiring' of Glucose Oxidase Within a Hydrogel Made with Polyvinyl Imidazole Complexed with [(Os-4,4'-dimethoxy-2,2'-bipyridine)Cl]$^{+/2+}$", *Journal of ElectroAnalytical Chemistry*, vol. 396, 1995, pp. 511-515.

Thompson, M., et al., "In Vivo Probes: Problems and Perspectives", *Clinical Biochemistry*, vol. 19, 1986, pp. 255-261.

Travenol Laboratories, Inc., *An Introduction to "Eugly"*, Book 1, 1985, pp. 1-22.

Trojanowicz, M., et al., "Enzyme Entrapped Polypyrrole Modified Electrode for Flow-Injection Determination of Glucose", *Biosensors & Bioelectronics*, vol. 5, 1990, pp. 149-156.

Tsalikian, E., et al., "Accuracy of the GlucoWatch G2® Biographer and the Continuous Glucose Monitoring System During Hypoglycemia: Experience of the Diabetes Research in Children Network", *Diabetes Care*, vol. 27, No. 3, 2004, pp. 722-726.

Turner, A., et al., "Diabetes Mellitus: Biosensors for Research and Management", *Biosensors*, vol. 1, 1985, pp. 85-115.

Turner, R. F., et al., "A Biocompatible Enzyme Electrode for Continuous in vivo Glucose Monitoring in Whole Blood", *Sensors and Actuators B*, vol. 1, 1990, pp. 561-564.

Tuzhi, P., et al., "Constant Potential Pretreatment of Carbon Fiber Electrodes for In Vivo Electrochemistry", *Analytical Letters*, vol. 24, No. 6, 1991, pp. 935-945.

Umana, M., "Protein-Modified Electrochemically Active Biomaterial Surface", *U.S. Army Research Office, Analytical and Chemical Sciences Research Triangle Institute*, 1988, pp. 1-9.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Urban, G., et al., "Miniaturized Thin-Film Biosensors Using Covalently Immobilized Glucose Oxidase", *Biosensors & Bioelectronics*, vol. 6, 1991, pp. 555-562.

Velho, G., et al., "In Vitro and In Vivo Stability of Electrode Potentials in Needle-Type Glucose Sensors", *Diabetes*, vol. 38, No. 2, 1989, pp. 164-171.

Velho, G., et al., "Strategies for Calibrating a Subcutaneous Glucose Sensor", *Biomedica Biochimica Acta*, vol. 48, 1989, pp. 957-964.

Von Woedtke, T., et al., "In Situ Calibration of Implanted Electrochemical Glucose Sensors", *Biomedica Biochimica Acta*, vol. 48, 1989, pp. 943-952.

Vreeke, M. S., et al., "Hydrogen Peroxide Electrodes Based on Electrical Connection of Redox Centers of Various Peroxidases to Electrodes through a Three-Dimensional Electron-Relaying Polymer Network", *Diagnostic Biosensors Polymers*, Chapter 15, 1993, pp. 180-193.

Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", *Analytical Chemistry*, vol. 64, No. 24, 1992, pp. 3084-3090.

Wang, D. L., et al., "Miniaturized Flexible Amperometric Lactate Probe", *Analytical Chemistry*, vol. 65, No. 8, 1993, pp. 1069-1073.

Wang, J., et al., "Activation of Glassy Carbon Electrodes by Alternating Current Electrochemical Treatment", *Analytica Chimica Acta*, vol. 167, 1985, pp. 325-334.

Wang, J., et al., "Amperometric Biosensing of Organic Peroxides with Peroxidase-Modified Electrodes", *Analytica Chimica Acta*, vol. 254, 1991, pp. 81-88.

Wang, J., et al., "Screen-Printable Sol-Gel Enzyme-Containing Carbon Inks", *Analytical Chemistry*, vol. 68, No. 15, 1996, pp. 2705-2708.

Wang, J., et al., "Sol-Gel-Derived Metal-Dispersed Carbon Composite Amperometric Biosensors", *Electroanalysis*, vol. 9, No. 1, 1997, pp. 52-55.

Williams, D. L., et al., "Electrochemical-Enzymatic Analysis of Blood Glucose and Lactate", *Analytical Chemistry*, vol. 42, No. 1, 1970, pp. 118-121.

Wilson, G. S., et al., "Progress Toward the Development of an Implantable Sensor for Glucose", *Clinical Chemistry*, vol. 38, No. 9, 1992, pp. 1613-1617.

(56) References Cited

OTHER PUBLICATIONS

Yabuki, S., et al., "Electro-Conductive Enzyme Membrane", *Journal of the Chemical Society, Chemical Communications*, 1989, pp. 945-946.

Yang, C., et al., "A Comparison of Physical Properties and Fuel Cell Performance of Nafion and Zirconium Phosphate/Nafion Composite Membranes," *Journal of Membrane Science*, vol. 237, 2004, pp. 145-161.

Yang, L., et al., "Determination of Oxidase Enzyme Substrates Using Cross-Flow Thin-Layer Amperometry", *Electroanalysis*, vol. 8, No. 8-9, 1996, pp. 716-721.

Yao, S. J., et al., "The Interference of Ascorbate and Urea in Low-Potential Electrochemical Glucose Sensing", *Proceedings of the Twelfth Annual International Conference of the IEEE Engineering in Medicine and Biology Society*, vol. 12, Part 2, 1990, pp. 487-489.

Yao, T., "A Chemically-Modified Enzyme Membrane Electrode as an Amperometric Glucose Sensor", *Analytica Chimica Acta*, vol. 148, 1983, pp. 27-33.

Ye, L., et al., "High Current Density 'Wired' Quinoprotein Glucose Dehydrogenase Electrode", *Analytical Chemistry*, vol. 65, No. 3, 1993, pp. 238-241.

Yildiz, A., et al., "Evaluation of an Improved Thin-Layer Electrode", *Analytical Chemistry*, vol. 40, No. 7, 1968, pp. 1018-1024.

Zamzow, K., et al., "New Wearable Continuous Blood Glucose Monitor (BGM) and Artificial Pancreas (AP)", *Diabetes*, vol. 39, 1990, pp. 5A-20.

Zhang, Y., et al., "Application of Cell Culture Toxicity Tests to the Development of Implantable Biosensors", *Biosensors & Bioelectronics*, vol. 6, 1991, pp. 653-661.

Zhang, Y., et al., "Elimination of the Acetaminophen Interference in an Implantable Glucose Sensor", *Analytical Chemistry*, vol. 66, No. 7, 1994, pp. 1183-1188.

PCT Application No. PCT/US2010/047413, International Search Report and Written Opinion of the International Searching Authority dated Dec. 27, 2010.

PCT Application No. PCT/US2010/047413, Preliminary Report on Patentability and Written Opinion of the International Searching Authority dated Mar. 15, 2012.

U.S. Appl. No. 12/873,298, Advisory Action dated Nov. 28, 2012.

U.S. Appl. No. 12/873,298, Notice of Allowance dated Nov. 24, 2014.

U.S. Appl. No. 12/873,298, Office Action dated Apr. 26, 2012.

U.S. Appl. No. 12/873,298, Office Action dated Aug. 29, 2012.

European Patent Application No. 10812782.0 Extended European Search Report dated Dec. 15, 2014.

\* cited by examiner

ANALYTE MONITORING SYSTEM AND METHODS FOR MANAGING POWER AND NOISE

RELATED APPLICATIONS

The present application is a divisional of U.S. patent application Ser. No. 12/873,298, filed Aug. 31, 2010, now U.S. Pat. No. 8,993,331, which claims priority under § 35 U.S.C. 119(e) to U.S. Provisional Patent Application No. 61/238,557, entitled "Analyte Monitoring System and Methods for Managing Power and Noise", filed on Aug. 31, 2009, and U.S. Provisional Patent Application No. 61/247,537 entitled "Analyte Measurement System for Managing Hardware and Temperature", filed on Sep. 30, 2009, the disclosures of each of which are incorporated herein by reference in their entirety for all purposes.

BACKGROUND

Diabetes Mellitus is an incurable chronic disease in which the body does not produce or properly utilize insulin. Insulin is a hormone produced by the pancreas that regulates blood sugar (glucose). In particular, when blood sugar levels rise, e.g., after a meal, insulin lowers the blood sugar levels by facilitating blood glucose to move from the blood into the body cells. Thus, when the pancreas does not produce sufficient insulin (a condition known as Type I Diabetes) or does not properly utilize insulin (a condition known as Type II Diabetes), the blood glucose remains in the blood resulting in hyperglycemia or abnormally high blood sugar levels.

The vast and uncontrolled fluctuations in blood glucose levels in people suffering from diabetes cause long-term, serious complications. Some of these complications include blindness, kidney failure, and nerve damage. Additionally, it is known that diabetes is a factor in accelerating cardiovascular diseases such as atherosclerosis (hardening of the arteries), leading to stroke, coronary heart disease, and other diseases. Accordingly, one important and universal strategy in managing diabetes is to control blood glucose levels.

The first step in managing blood glucose levels is testing and monitoring blood glucose levels by using conventional techniques, such as drawing blood samples, applying the blood to a test strip, and determining the blood glucose level using colorimetric, electrochemical, or photometric test meters. Another more recent technique for monitoring blood glucose levels is by using a continuous or automatic glucose monitoring system. Unlike conventional blood glucose meters, continuous analyte monitoring systems employ an insertable or implantable sensor, which continuously detects and monitors blood glucose levels. These blood glucose levels may then be displayed to a user to assist the user in managing the user's diabetes. However, as battery life drains from one or more components of the continuous analyte monitoring system, such as a receiver, data corresponding to the monitored blood glucose levels may be lost or become corrupt if the receiver of the analyte monitoring system shuts down due to lack of power in a rechargeable power source of the receiver. Additionally, noise produced by various components of the analyte monitoring system may interfere with a signal that conveys the monitored blood glucose levels.

INCORPORATED BY REFERENCE

The following patents, applications and/or publications are incorporated herein by reference for all purposes: U.S. Pat. Nos. 4,545,382; 4,711,245; 5,262,035; 5,262,305; 5,264,104; 5,320,715; 5,356,786; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,041,468; 7,167,818; and 7,299,082; U.S. Published Application Nos. 2004/0186365, now U.S. Pat. No. 7,811,231; 2005/0182306, now U.S. Pat. No. 8,771,183; 2006/0025662, now U.S. Pat. No. 7,740,581; 2006/0091006; 2007/0056858, now U.S. Pat. No. 8,298,389; 2007/0068807, now U.S. Pat. No. 7,846,311; 2007/0095661; 2007/0108048, now U.S. Pat. No. 7,918,975; 2007/0199818, now U.S. Pat. No. 7,811,430; 2007/0227911, now U.S. Pat. No. 7,887,682; 2007/0233013; 2008/0066305, now U.S. Pat. No. 7,895,740; 2008/0081977; 2008/0102441, now U.S. Pat. No. 7,822,557; 2008/0148873, now U.S. Pat. No. 7,802,467; 2008/0161666; 2008/0267823; and 2009/0054748, now U.S. Pat. No. 7,885,698; U.S. patent application Ser. No. 11/461,725, now U.S. Pat. No. 7,866,026; Ser. Nos. 12/131,012; 12/393,921, 12/242,823, now U.S. Pat. No. 8,219,173; Ser. No. 12/363,712, now U.S. Pat. No. 8,346,335; Ser. Nos. 12/495,709; 12/698,124; 12/698,129; 12/714,439; 12/794,721, now U.S. Pat. No. 8,595,607; and Ser. No. 12/842,013, and U.S. Provisional Application Nos. 61/317,243, 61/345,562, and 61/361,374.

SUMMARY

Embodiments described herein relate to systems and methods for selectively disabling components of an analyte monitoring device based on a percentage of power remaining in a power source of the analyte monitoring device. As such, the analyte monitoring device is configured to determine a temperature level of the power source of the analyte monitoring device, determine a level of power remaining in the power source of the analyte monitoring device, and selectively deactivate at least one component of the analyte monitoring device when at least one of the temperature levels of the power source reaches a predetermined temperature threshold or when the level of power remaining in the power source reaches a predetermined power threshold. Also disclosed herein are methods and systems for reducing noise caused by components of the analyte monitoring device during data transmission and/or reception.

These and other objects, features and advantages of the present disclosure will become more fully apparent from the following detailed description of the embodiments, the appended claims and the accompanying drawings.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the pres

DETAILED DESCRIPTION

Figure 1:
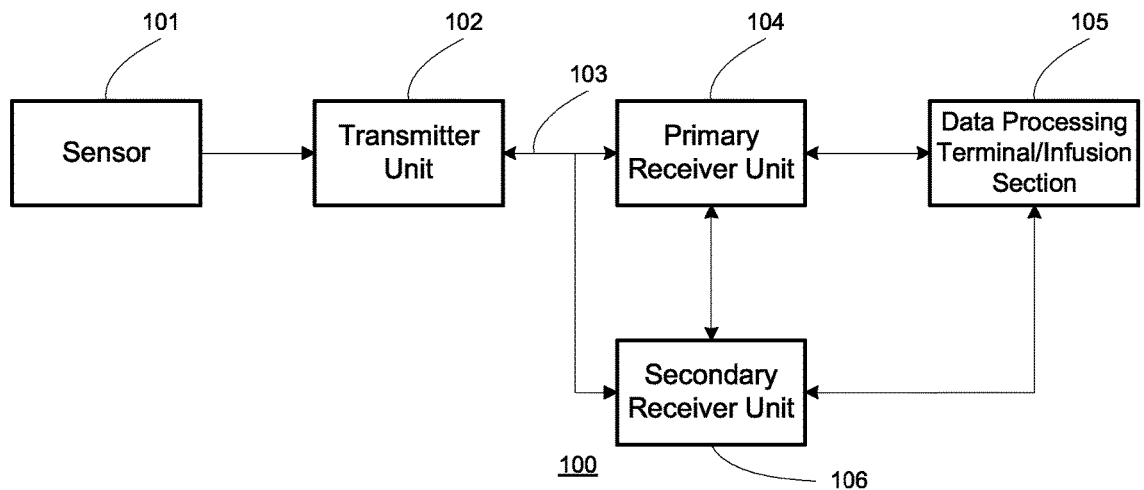
- FIG. 1 illustrates a block diagram of a data monitoring and management system according to embodiments of the present disclosure.

Before the present disclosure is described in detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges as also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Various exemplary embodiments of the analyte monitoring system and methods of the disclosure are described in further detail below. Although the disclosure is described primarily with respect to a glucose monitoring system, each aspect of the disclosure is not intended to be limited to the particular embodiment so described. Accordingly, it is to be understood that such description should not be construed to limit the scope of the disclosure, and it is to be understood that the analyte monitoring system can be configured to monitor a variety of analytes, as described below.

FIG. 1 illustrates a data monitoring and management system such as, for example, analyte (e.g., glucose) monitoring system 100 in accordance with embodiments of the present disclosure. In certain embodiments, the analyte monitoring system 100 may be a continuous monitoring system, a semi-continuous monitoring system, a discrete monitoring system or an on-demand monitoring system. The analyte monitoring system 100 includes a sensor 101, a transmitter unit 102 coupleable to the sensor 101, and a primary receiver unit 104 which is configured to communicate with the transmitter unit 102 via a bi-directional communication link 103. The primary receiver unit 104 may be further configured to transmit data to a data processing terminal 105 for evaluating the data received by the primary receiver unit 104. Moreover, the data processing terminal 105 in one embodiment may be configured to receive data directly from the transmitter unit 102 via a communication link which may optionally be configured for bi-directional communication. Accordingly, transmitter unit 102 and/or receiver unit 104 may include a transceiver.

Also shown in FIG. 1 is an optional secondary receiver unit 106 which is operatively coupled to the communication link and configured to receive data transmitted from the transmitter unit 102. Moreover, as shown in the Figure, the secondary receiver unit 106 is configured to communicate with the primary receiver unit 104 as well as the data processing terminal 105. Indeed, the secondary receiver unit 106 may be configured for bi-directional wireless communication with each or one of the primary receiver unit 104 and the data processing terminal 105. In one embodiment of the present disclosure, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, pager, mobile phone, or Personal Digital Assistant (PDA), for example. Alternatively, the secondary receiver unit 106 may be configured with the same or substantially similar functionality as the primary receiver unit 104. The receiver unit may be configured to be used in conjunction with a docking cradle unit, for one or more of the following functions: placement by bedside, re-charging, data management, night time monitoring, and/or bi-directional communication device.

In one aspect, sensor 101 may include two or more sensors each configured to communicate with transmitter unit 102. Furthermore, while only one, transmitter unit 102, communication link 103, and data processing terminal 105 are shown in the embodiment of the analyte monitoring system 100 illustrated in FIG. 1, in certain embodiments, the analyte monitoring system 100 may include one or more sensors, multiple transmitter units 102, communication links 103, and data processing terminals 105. Moreover, within the scope of the present disclosure, the analyte monitoring system 100 may be a continuous, semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present disclosure, the sensor 101 is physically positioned in or on the body of a user whose analyte level is being monitored. The sensor 101 may be configured to continuously sample the analyte level of the user and convert the sampled analyte level into a corresponding data signal for transmission by the transmitter unit 102. In certain embodiments, the transmitter unit 102 may be physically coupled to the sensor 101 so that both devices are integrated in a single housing and positioned on the user's body. The transmitter unit 102 may perform data processing such as filtering and encoding on data signals and/or other functions, each of which corresponds to a sampled analyte level of the user, and in any event transmitter unit 102 transmits analyte information to the primary receiver unit 104 via the communication link 103. Additional detailed description of the continuous analyte monitoring system, its various components including the functional descriptions of the transmitter are provided in, but not limited to, U.S. Pat. Nos. 6,134,461, 6,175,752, 6,121,611, 6,560,471, and 6,746,582, and U.S. Patent Publication No. 2008/0278332 and elsewhere, the disclosures of each of which are incorporated by reference for all purposes.

Figure 2:
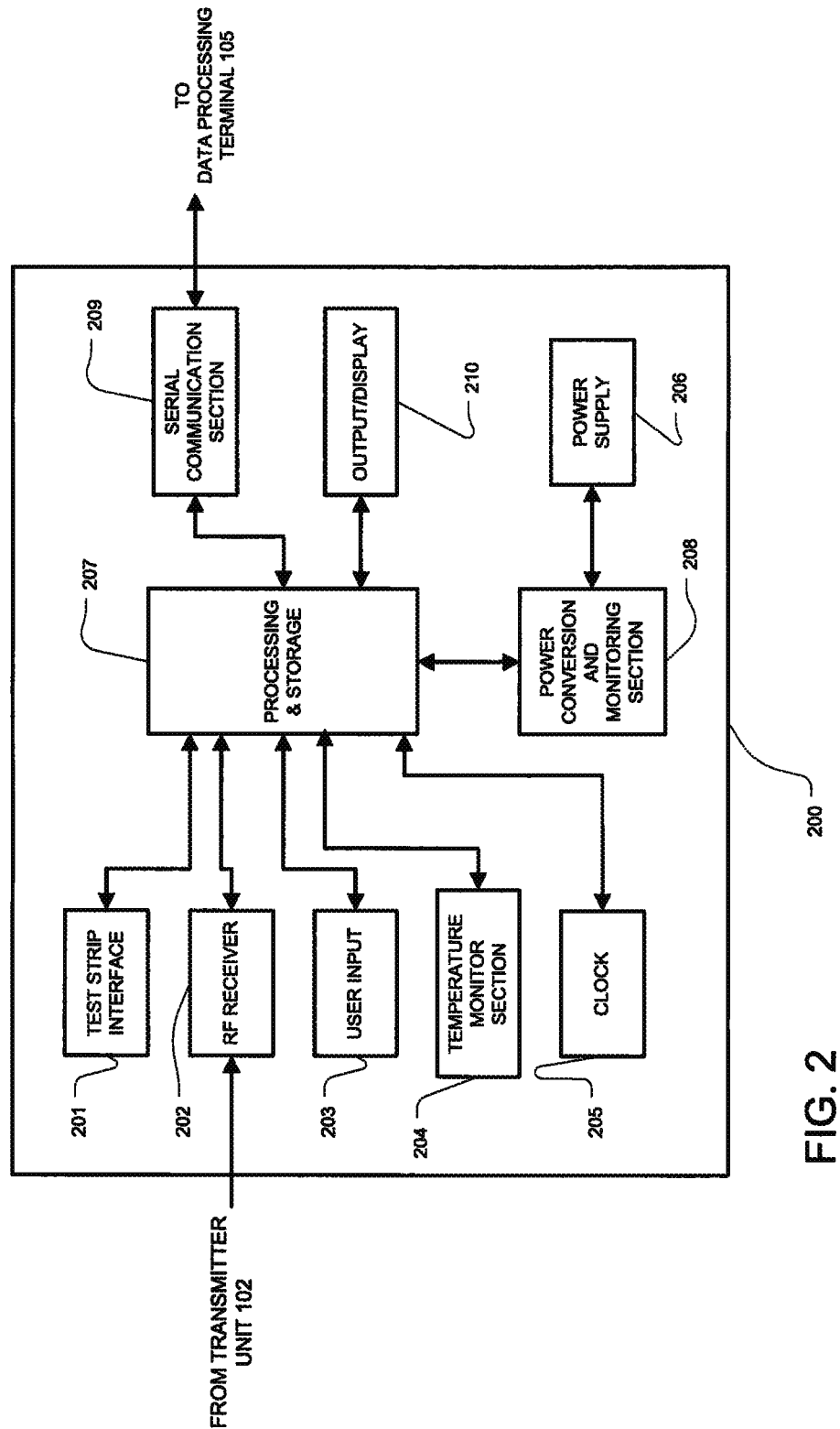
FIG. 2 is a block diagram of a receiver unit according to embodiments of the present disclosure.

FIG. 2 is a block diagram of a receiver 200 according to embodiments of the present disclosure. In certain embodiments, receiver 200 may be the primary receiver unit 104 (FIG. 1) or the secondary receiver unit 106 as described above. As illustrated in the block diagram, the receiver 200 includes an analyte test strip interface 201, (e.g., blood glucose test strip port), a radio frequency (RF) receiver 202, a user input mechanism 203 (e.g., one or more keys of a keypad, a touch-sensitive screen, a voice-activated input command unit etc.), a temperature detection section 204, and a clock 205, each of which is operatively coupled to a receiver processor 207. In certain embodiments, the receiver 200 also includes a power supply 206, such as, for example, a rechargeable battery, operatively coupled to a power conversion and monitoring section 208. Further, the power conversion and monitoring section are also coupled to the receiver processor 207. A receiver serial communication section 209, and an output 210, such as, for example a display, are each operatively coupled to the receiver processor 207. In certain embodiments and as briefly discussed above, the analyte monitoring system 100 is a continuous glucose monitoring system, and the test strip interface 201 includes a glucose level testing portion to manually receive a glucose test strip to determine the glucose level of a blood sample applied to the test strip. In response to receiving a test strip, the receiver 200 may be configured to output blood glucose information determined from the test strip on the display. Additionally, the test strip can be used to calibrate a sensor such as, for example sensor 101.

In accordance with an embodiment, the receiver 200 includes two sections. The first section is an analog interface section that is configured to communicate with the transmitter unit 102 via the communication link 103. In certain embodiments, the analog interface section may include an RF receiver and an antenna for receiving and amplifying the data signals from the transmitter unit 102, which are thereafter, demodulated with a local oscillator and filtered through a band-pass filter. The second section of the receiver is a data processing section which is configured to process the data signals received from the transmitter unit 102 such as by performing data decoding, error detection and correction, data clock generation, and data bit recovery.

In certain embodiments, various data processing functionalities are executed by the receiver 200 such as, for example, calibration of analyte levels received from the sensor 101 and the transmitter unit 102 and techniques for managing power and noise of the analyte monitoring system 100, based on the periodic transmission of data from the transmitter unit 102.

In certain embodiments, a receiver 200 has an operating mode which prevents a user from operating the receiver 200 or suspends or deactivates certain functionalities of the receiver during certain conditions. Such conditions may include a low battery level of the receiver 200, such as, for example, a low battery level that prompts hardware shutdown. Other conditions may include low or high operating temperatures of the receiver 200 that may cause data corruption or erroneous behavior if the receiver 200 were to continue operating under such conditions. As will be described in greater detail below, this suspended functionality mode is referred herein as a play dead mode. In play dead mode, the receiver 200 continues to run a main clock and perform certain internal operations to keep desired data updated and current. Such operations and/or data may include operations and data corresponding to sensor life, calibration, timing of the receipt of data packets and the like. Although certain operations remain active, other operations of the receiver 200 are suspended. In certain embodiments, the operations that are suspended include writing data to memory, such as, for example a flash memory of the receiver 200, outputting sounds such as alarms, tones and/or other notifications, displaying data on a display unit, or communicating commands to a remotely controlled device, such as, for example, a pump.

In certain embodiments, one or more processors of the receiver 200 utilize a battery monitoring algorithm which performs a charge counting routine when determining whether to enter the play dead mode. More specifically, the charge counting routine in certain embodiments includes determining an estimate corresponding to an amount of battery charge available on a well-functioning battery during the lifecycle of the receiver 200. In certain embodiments, the battery monitoring algorithm takes into account variations in batteries from different manufacturers as well as an estimate of degradation of the battery capacity due to aging over the lifetime of the battery.

Figure 3:
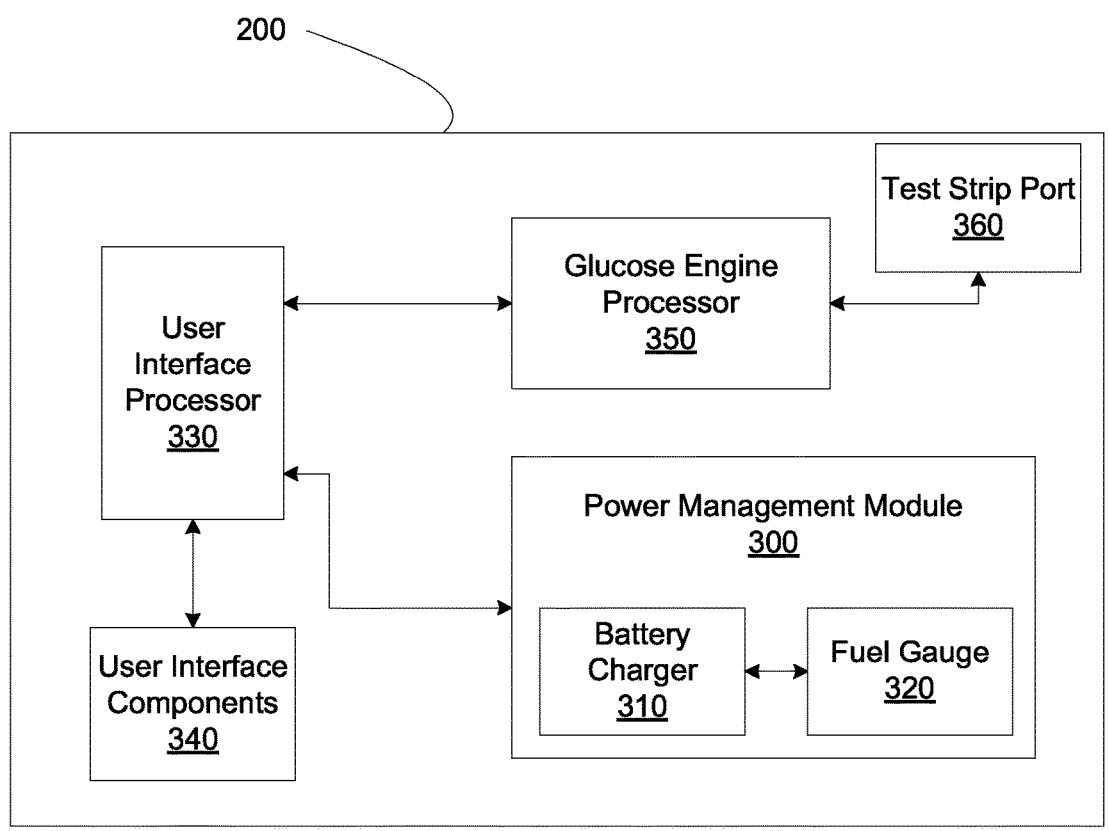
FIG. 3 is a block diagram of a battery management feature of a receiver according to embodiments of the present disclosure.

Referring to FIG. 3, in certain embodiments, the battery monitoring algorithm and associated battery management and charging functionalities of the receiver 200 is performed by power management module 300. In certain embodiments, the power management module 300 is equivalent to power conversion and monitoring section 208 (FIG. 2) and includes a battery charger 310 and a fuel gauge 320. In one aspect, the power management module 300 is configured to prevent a power supply 206 (e.g., rechargeable battery) of the receiver 200 from charging when a detected temperature of the receiver 200 and/or the battery is not in safe operating range. In certain embodiments, the power management module 300 is configured to prevent the battery from being continuously charged after the battery has been charging for a maximum charging period (e.g., more than about 3 hours). In certain embodiments, when the remaining power level of a battery of the receiver 200 reaches a predetermined minimum threshold level, the power management module 300 is configured to cut off power to one or more processors of the receiver 200, which may suspend or deactivate various functionalities of the receiver 200.

For example, the receiver 200 may have a user interface processor 330 configured to process commands received from, and output data to, various user interface components 340. In certain embodiments, the user interface components 340 may include, one or more buttons disposed on a housing of the receiver 200, a display, such as, for example a touch sensitive display, a sound synthesizer, a vibration component, and/or a backlight. Although specific components are mentioned, it is contemplated that the receiver may include additional user interface components configured to enable a user to interact with the receiver 200. In certain embodiments, the user interface processor 330 is configured to interact with the various user interface components 340 including updating the display of the receiver 200, processing received glucose data, maintaining a log of historical information, operating the sound synthesizer and/or the vibration component, and/or interface with the power management module 300. In addition to the user interface processor 330, the receiver 200 may also include glucose engine processor 350 configured to receive and process analyte data received from a transmitter, such as, for example, transmitter unit 102 (FIG. 1) and/or data received from a test strip port 360. In certain embodiments, test strip port 360 may be equivalent to test strip interface 201 (FIG. 2). Depending on how much power each of the above mentioned processors are consuming, one or more operations or functionalities of the receiver 200 that are controlled by each of the above mentioned processors may be deactivated or suspended when entering the play dead mode.

In certain embodiments, the battery monitoring algorithm discussed above incorporates several design constraints and considerations. For example, one consideration is discharge of the battery of the receiver 200. In one aspect, the battery of the receiver 200 is a lithium-ion battery. As these types of batteries may be damaged when deeply discharged (e.g., discharging the battery below a certain percentage of the charge capacity of the battery), the power management module 300 may be configured to cut or reduce power to one or more processors of the receiver 200 when the battery voltage drops below a certain voltage minimum threshold (e.g., about 3.3V).

In certain embodiments, when the voltage remaining in the battery drops below a certain threshold, for example about 3.6V, the battery is considered an empty battery and the power management module 300 reduces or cuts power to one or more of the processors to conserve the remaining battery power. In such situations, and as described above, when the power management module 300 cuts power from the battery, certain functionalities of the receiver 200 are disabled while other functionalities of the receiver 200 may remain active. In one aspect, one or more processors of the receiver 200 may be configured to determine which components and/or operations (e.g. writing to flash memory, updating a display, etc.) controlled by a particular processor are consuming the most power. The processor may then deactivate one or more operations and/or components that are consuming the most power while other operations and/or components controlled by that processor remain active.

For example, the user interface processor 330 may control a display and a light source of the receiver 200. When battery power reaches the predetermined minimum threshold, the user interface processor 330 may determine that continued operation of the light source will require more power than operation of the display. As such, the light source will be deactivated until the battery of the receiver 200 is recharged, but the display remains active. Although one component controlled by a processor may remain active while another component is deactivated as was described above, it is contemplated that as battery power continues to drain, the active component (e.g., the active display) controlled by the user interface processor 330 may be subsequently deactivated when remaining power of the battery reaches a second predetermined minimum threshold. When this threshold is reached, the processor of the receiver 200 may again determine which active component and/or operation is consuming the most battery power and temporarily deactivate that particular component or operation.

In another aspect, temperature damage to the battery may also be prevented using the power management module 300. For example, a lithium-ion battery can be damaged if the battery is exposed to extreme temperatures, especially hot temperatures. Additionally, low battery temperature may cause the internal resistance of the battery to increase significantly. The increase in internal resistance results in a voltage drop when the device turns on high current loads such as, for example, when a display of the receiver 200 is activated or when an alarm is output. It is beneficial to avoid or prevent voltage drops of a battery because a voltage drop may cause the operating system of the receiver 200 to unexpectedly reset. As a result of the reset, data may be lost. In certain embodiments, the temperature of the battery is monitored while the battery is being charged. If the temperature of the battery exceeds a threshold temperature, the processor of the receiver 200 issues a command to temporarily discontinue charging the battery.

Figure 4:
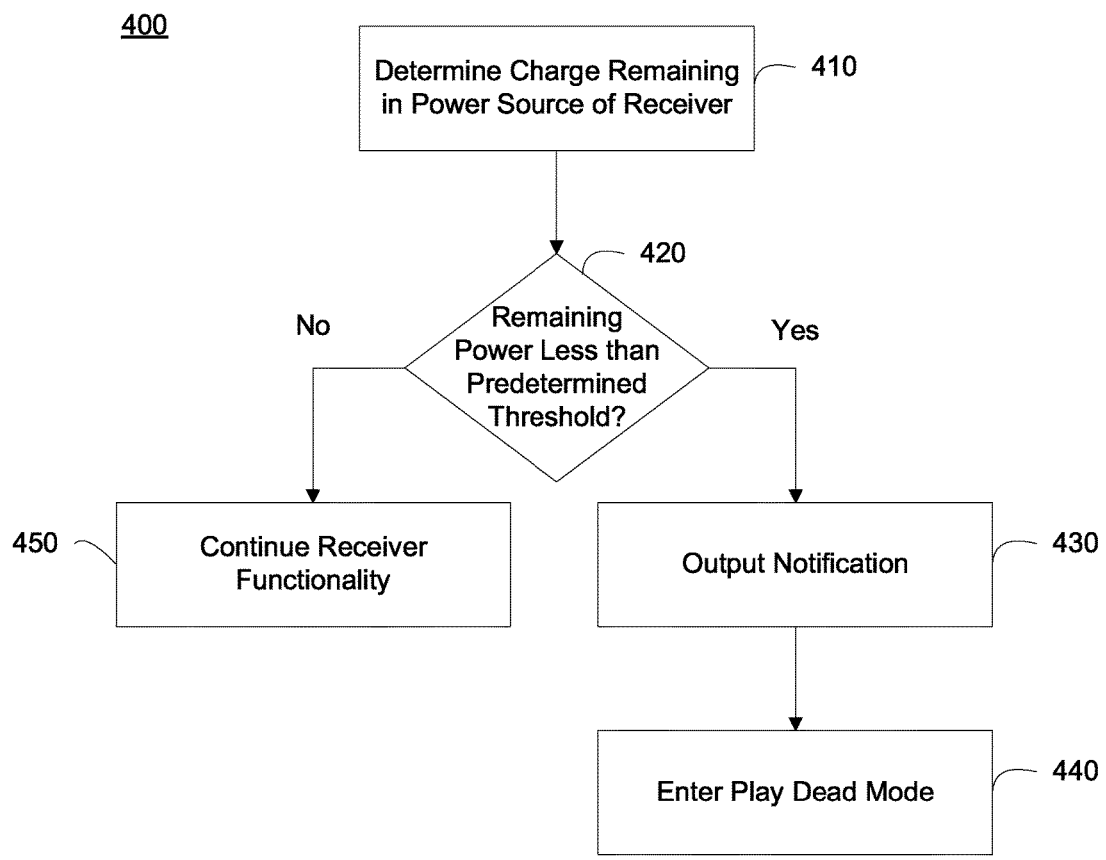
FIG. 4 is a flow chart illustrating a method for determining whether a receiver is to enter a play dead mode according to embodiments of the present disclosure.

FIG. 4 illustrates a method 400 for determining whether a receiver, such as, for example, receiver 200 (FIG. 2) is to enter a play dead mode, according to embodiments of the present disclosure. Referring to FIG. 4, initially, a processor of the receiver 200 determines an amount of power or charge remaining in a power source of the receiver 200 (410). In certain embodiments, a processor of the receiver 200, such as, for example, a user interface processor 330 (FIG. 3), is configured to collect and maintain battery information, such as charge count information (e.g., an amount of power remaining in the battery), at any given time. In addition to determining the battery information, the user interface processor 330 of the receiver 200 may be configured to determine battery aging error. For example, due to the age of a battery, a small percentage of battery capacity may be lost during its usage. Accordingly, this error may be detected and the actual capacity of the battery based on the current age of the battery is updated. Thus, when the remaining charge level of the battery is determined, the determination is based on the current capacity of the aged battery rather than the capacity of the battery when it was new.

In certain embodiments, when the receiver 200 is powered on, the charge count of the battery is determined based on certain conditions. For example, if the receiver 200 is recovering from a hard or soft reset, battery information that was previously stored in a memory of the receiver 200 is checked to determine if the battery information is valid. Such a determination may be made by the processor comparing the stored battery information to an estimate of the remaining power in the power source. If the battery information stored in the memory is validated, the charge count of the battery is set as the battery information that is stored in the memory. In situations where the system is reset due to a power on procedure, such as, for example, powering on the receiver 200, the charge count stored in the memory is retrieved and checked for validity. If the battery information in memory is valid, the stored battery information is compared to an actual voltage reading from the battery. If the stored battery information is within a predetermined range, such as ±0.5V of the actual voltage read from the battery, the charge count of the battery is set to the value that was stored in the memory. In another aspect, if it is determined by the user interface processor 330 that the battery voltage is below a minimum threshold, such as 3.6V or less, the charge count is set to zero and the receiver 200 enters play dead mode and/or prompts the user to begin recharging the battery. If the stored battery information is invalid, the charge count is initialized to zero and the user is prompted, via a display or alarm notification, that the battery of the receiver 200 needs to be recharged.

In certain embodiments, the user interface processor 330 of the receiver 200 receives a charge count interrupt signal, and based on the signal, determines when the battery is being charged, when the battery is fully charged, and when power from the battery is being discharged. For example, when the charge count interrupt signal is received by the processor and the signal is high, the user interface processor 330 is configured to increment a charge count. However, when the charge count interrupt signal is received and the signal is low, the user interface processor 330 subtracts one charge count. Thus, based on the charge count, the user interface processor 330 may determine how much power remains in the battery and/or when the charge count has reached a maximum count.

In certain embodiments, the user interface processor 330 of the receiver 200 is configured to calculate and display an amount of power remaining in the battery of the receiver 200. As discussed above, when the remaining battery power reaches a predetermined minimum threshold level, the user interface processor 330 is configured to issue a command to output a notification to the user that the receiver 200 is about to enter the play dead mode because the remaining battery power is at or below a threshold power level. In another aspect, the user interface processor 330 is also configured to notify the user when the battery of the receiver 200 is fully charged. In certain embodiments, the display of the receiver 200 is configured to visually output the remaining power of the battery of the receiver 200. In certain embodiments, the remaining power of the battery of the receiver 200 is output in the form of an icon that displays an amount of power remaining in the battery. It also serves as an indication that all subsystems (e.g., test strip port functionality, display functionality, etc.) of the receiver 200 can be used without the risk of data loss or data corruption due to sudden or unexpected receiver 200 shutdown.

In certain embodiments, the battery icon is output on the display having at least four indicators with each of the indicators representing a portion of the battery life. Although four indicators are specifically mentioned, it is contemplated that any number of indicators may be used. As battery life of the receiver 200 drains, each of the indicators of the battery icon may be output in a different color. For example, as battery life is depleted from a 100% charge to a 75% charge, the user interface processor 330 of the receiver 200 causes the first indicator of the battery icon to change from green, to yellow to red to indicate that the user is reaching 75% charge while the remaining three indicators of the battery icon are output in green. As power of the battery of the receiver 200 is continually discharged, the remaining three indicators are output in different colors to indicate the percentage of power remaining in the battery. In certain embodiments, the battery icon may also indicate the level or percentage of power remaining in the battery in which the user may continue to use all systems and functionalities of the receiver 200, such as, for example, the display or the test strip port 360. Additionally, the battery icon may display whether the battery of the receiver 200 is charging.

Referring back to FIG. 4, once the user interface processor 330 has determined the amount of charge remaining in the battery of the receiver 200, the determined amount of charge is compared to a minimum predetermined power threshold level (420). If it is determined that the charge count of the battery is greater than the predetermined threshold, all subsystems and functionalities of the receiver remain active (450). However, if it is determined that the charge count of the battery is less than the predetermined threshold, the user interface processor 330 is configured to output a notification (430) that the receiver 200 will be entering the play dead mode and that some functionalities of the receiver 200 will be deactivated. In one aspect, the user interface processor 330 may be configured to determine which components of the receiver 200 are consuming the most power and selectively deactivate the identified components. Additionally, the notification may also indicate which components and/or operations of the receiver 200 will be deactivated when the play dead mode is entered.

In certain embodiments, various alarms or other notifications may be output from the receiver 200 to warn the user that the power remaining in the battery is reaching a threshold level (e.g., 25% power). In another embodiment, multiple warnings or alerts may be output based on certain battery levels being reached. For example, when the amount of power remaining in the battery reaches a first level, a user is warned that the battery needs to be charged within a determined amount of time based on current battery power consumption. When the remaining amount of power in the battery reaches a second level, the receiver 200 enters the play dead mode (440). In another embodiment, the user interface processor 330 of the receiver 200 is configured to estimate a time frame based on the current battery usage as to when the receiver 200 will enter the play dead mode. If the estimated amount of time elapses, the receiver 200 enters play dead mode (440).

Additional description of alarms and the output of the alarms and play dead mode for certain embodiments are shown in Table 1 below.

TABLE 1

| Parameter | Description | Level |
|---|---|---|
| Maximum Charge count | The programmed battery capacity. | 12,000 |
| Level 0 threshold percentage | The battery percentage at which all bars displayed in the UI. | 75%-100% charge |
| Level 1 threshold percentage | The battery percentage at which 3 bars displayed in the UI. | 50%-75% charge |
| Level 2 threshold percentage | The battery percentage at which 2 bars displayed in the UI. | 25%-50% charge |
| Level 3 threshold percentage | The battery percentage at which 1 bar is displayed in the UI. | 0%-25% charge |
| Battery Low Alarm 1 percentage | The battery percentage at which the first low battery alarm displayed to the user. | <25% charge |

TABLE 1-continued

| Parameter | Description | Level |
|---|---|---|
| Battery Low Alarm 2 percentage | The battery percentage at which the second low battery alarm displayed to the user. | <3.65 V or <15% charge |
| Battery Warn Voltage | The battery voltage below which the battery low alarm should be raised. | 3.65 V |
| Battery Dead Voltage | The battery voltage below which system should be placed in play dead state. | 3.6 V |
| Battery Self Test Voltage | The battery voltage below which the self test (initiated by USB removal) will not be performed. | 3.7 V |

Figure 5:
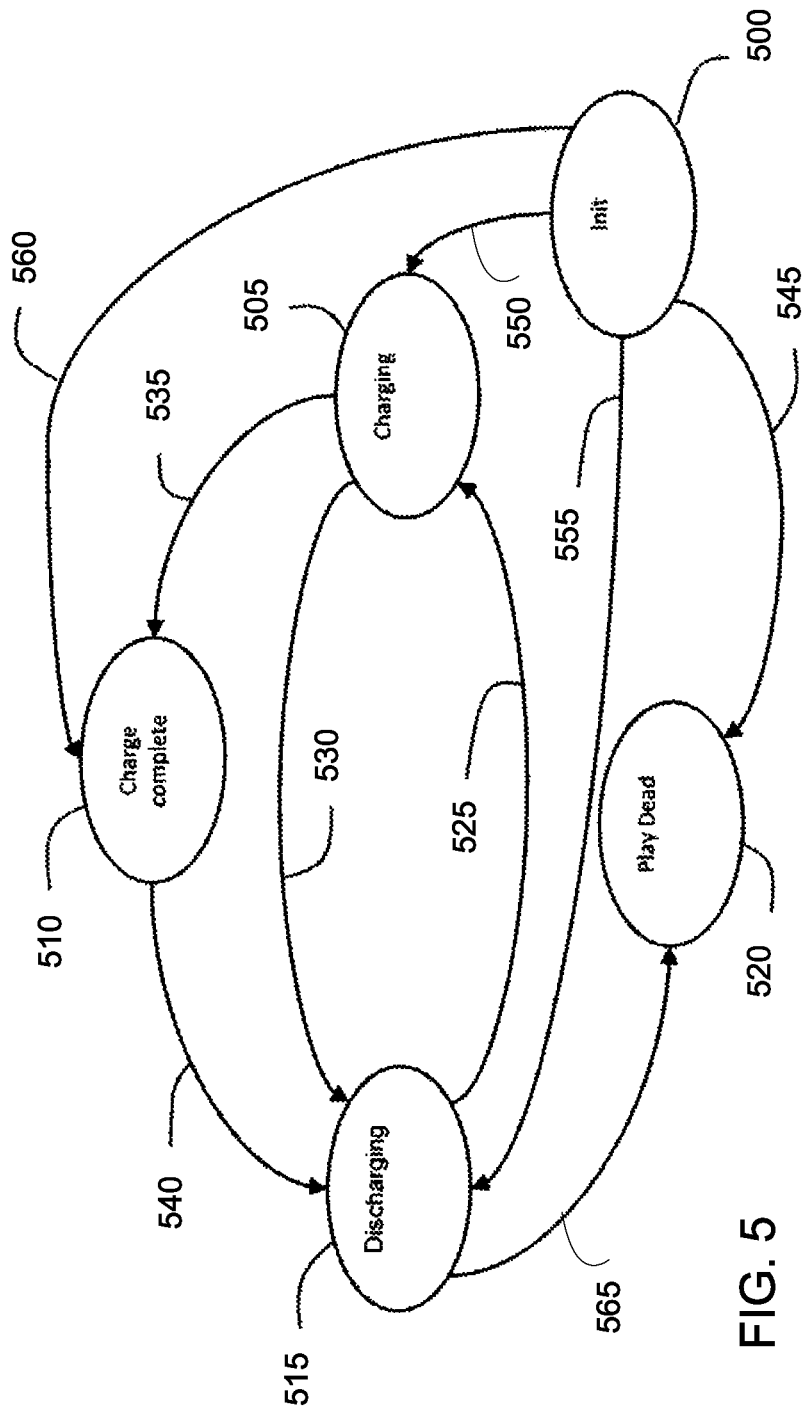
FIG. 5 is a state diagram of battery charge and discharge features of a receiver according to embodiments of the present disclosure.

FIG. 5 is a state diagram of battery charge and discharge features of a receiver, such as, for example, receiver 200 (FIG. 2) according to embodiments of the present disclosure. As shown in FIG. 5, various states of the battery include an initial state 500, a battery charging state 505, a charge complete 510 state, a discharging state 515, and play dead state 520. Although specific states have been discussed, it is understood that additional states may be used to govern the power supply.

In certain embodiments, the battery remains in the charging state 505 when the receiver 200 is connected to a peripheral power source and the battery voltage and the receiver temperature are in a safe operation range. In the charging state 505, all operations and functionalities of the receiver 200 are operable except for test strip measurements and a user initiated self test of the receiver 200. In certain embodiments, a self test enables a user to select and run a self test mode in which the receiver 200 automatically tests whether various components of the receiver are working properly. Such components may include a display, a speaker, a memory, a vibratory indicator, and/or a test strip port light. After each successive test, the results may be audibly and/or visually output to a user. Although specific self tests have been mentioned, it is contemplated that additional self tests related to other components of the receiver may be performed.

As discussed above, when in the charging state 505, an icon may be output on the display to indicate that a battery of the receiver 200 is currently being charged. In one aspect, the receiver 200 enters the charge complete state 510 when the battery is completely charged and a USB cable is connected to the receiver 200. However, as stated above, although the receiver 200 may still be connected to a power source, when the fully charged state 510 is reached, the processor, such as, for example, the user interface processor 330 (FIG. 3) may be configured to cut off power to the battery so as not to overcharge the battery. As power from the battery is being discharged (e.g., 100% to 20% battery life remaining) all functionalities of the receiver 200 are active, such as was described above with reference to FIG. 4. Additionally, the display may be configured to graphically output the remaining battery power.

When battery life reaches about 20% to 0%, the receiver 200 enters the play dead mode 520 described above. In the play dead mode 520, certain functionalities of the receiver 200 are inoperable. State transitions illustrated in FIG. 5 are further described in Table 2 below.

TABLE 2

| Transition | From | To | Description |
|---|---|---|---|
| 525 | Discharging | Charging | The receiver is placed in USB cradle or connected to a USB cable, and the battery is being charged. |
| 530 | Charging | Discharging | The receiver is removed from USB cradle or disconnected from the USB cable and the system is operating with battery power. |
| 535 | Charging | Charge complete | The battery is fully charged. |
| 540 | Charge complete | Discharging | The battery is in a completely charged state and the receiver is removed from USB cradle or the USB cable is removed. |
| 545 | Init | Play dead | At reset when the USB is not connected and the battery voltage is less than "PLAY_DEAD_VOLTAGE" or the charge count is less than 20% of the actual capacity. |
| 550 | Init | Charging | At reset when the USB is connected. |
| 555 | Init | Discharging | At reset when the USB is not connected and the battery voltage is greater than "PLAY_DEAD_VOLTAGE" and the charge count is greater than 20% of the actual capacity. |
| 560 | Init | Charge complete | At reset when the USB is connected and the battery charging is not initiated within 3 seconds. |
| 565 | Discharging | Play dead | Charge count drops below the "PLAY_DEAD_VOLTAGE". |

Figure 6:
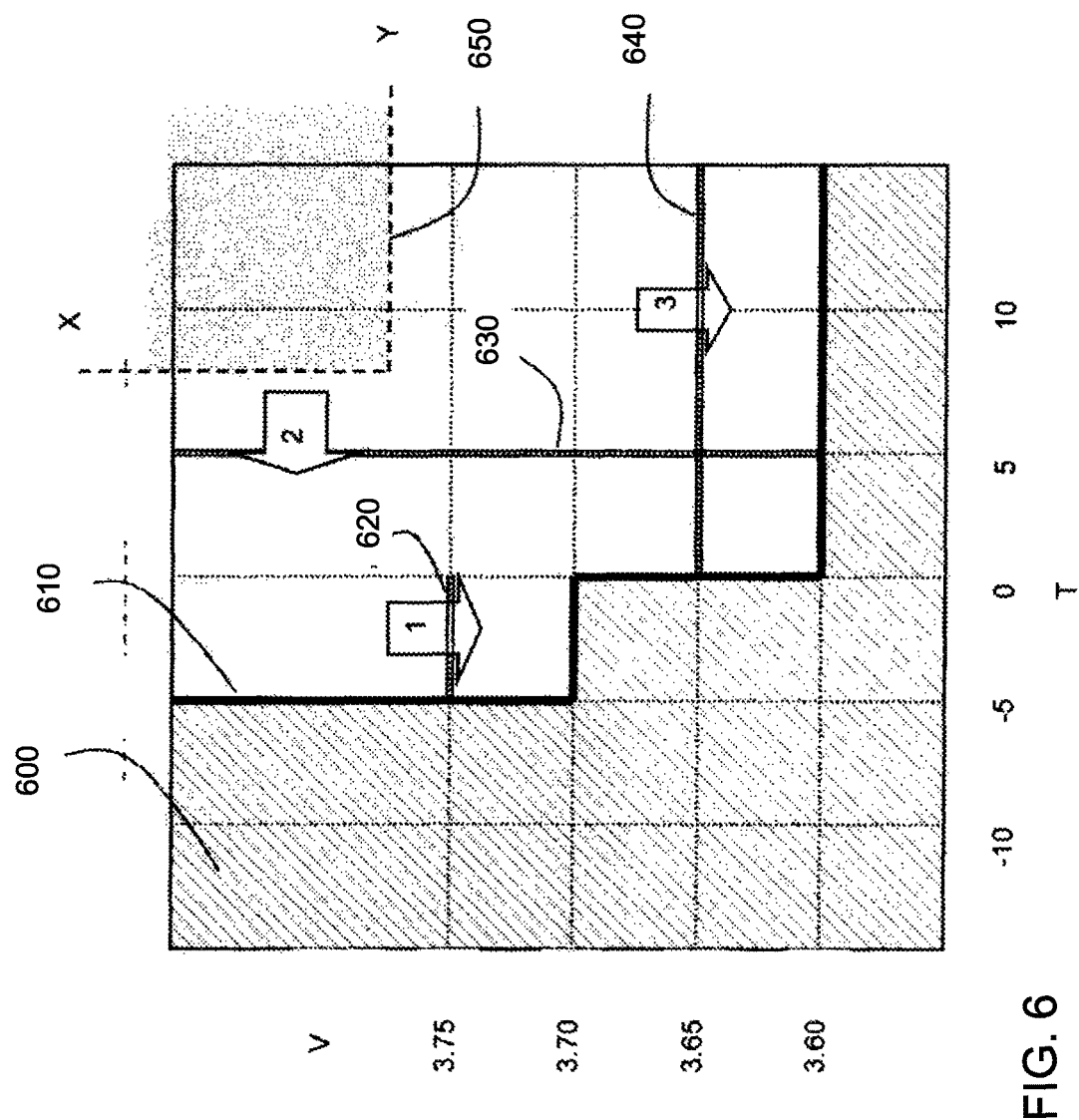
FIG. 6 illustrates temperature and voltage conditions of a receiver entering a play dead mode according to embodiments of the present disclosure.

Further aspects of the play dead mode are illustrated in FIG. 6. For example, in certain embodiments, the receiver 200 (FIG. 2) may be configured to enter play dead mode as a function of both voltage and temperature. An exemplary embodiment of the play dead mode is illustrated as the hatched region 600 of FIG. 6. For example, the receiver 200 enters the play dead mode at different minimum voltages depending upon the battery temperature. In one aspect, the receiver 200 may be configured to enter the play dead mode when one of two temperatures and corresponding minimum voltages are reached. For example, the two temperatures may be −5° C., and 0° C., and the two corresponding minimum voltages may be 3.6V and 3.7V. As indicated by solid black line 610, the receiver 200 enters the play dead mode if the battery temperature is less than a first temperature (e.g., −5° C.), regardless of the battery voltage. In another embodiment, the receiver 200 enters the play dead mode if the battery temperature is between the first and second temperatures (e.g., 0° C. and −5° C.) and the battery voltage is less than a first battery voltage (e.g., about 3.7V). If the battery temperature is greater than the second temperature (e.g., 0° C.) or if the voltage is less than the second battery voltage (e.g., 3.7V), the receiver 200 will also enter the play dead mode. It is understood that a fewer or greater number of battery temperature and voltage points may be selected, based upon the application (e.g., battery characteristics and power demands). Moreover, the battery temperature and voltages that cause the transition to the play dead mode may be selectable and/or customizable by the user or health care professional.

With continued reference to FIG. 6, alarms are provided as illustrated by the solid and dashed lines 620, 630, 640. As indicated by arrow 1, an alarm is output if the voltage of the battery is less than 3.75V and the battery temperature is between 0° C. and −5° C. (620). As indicated by arrow 3, an alarm is output if the voltage is less than 3.65V and the battery temperature is greater than 0° C. (640). As indicated by arrow 2, an alarm sounds if the battery temperature is less than 5° C. and the voltage is greater than 3.6V (630). An auto-recover mode is identified by the dashed lines (650). In certain embodiments, the receiver 200 is configured to automatically exit the play dead mode via the auto-recover mode when the processor detects that the voltage level of the battery exceeds 3.8V and/or the battery temperature exceeds 8° C.

In another aspect of the present disclosure, the receiver 200 may be configured to reduce the overall electronic noise of the receiver 200 during periods when data transmission is occurring, such as, for example, when the receiver 200 is expecting a data packet from a transmitter unit, such as, for example, transmitter unit 102 (FIG. 1). To accomplish the noise reduction, a processor of the receiver 200, such as, for example, user interface processor 330 (FIG. 3) is configured to temporarily reduce the functionality of at least one component of the receiver 200 during the transmission of signals from the transmitter unit 102.

One implementation of the noise reduction is referred to herein as the "quiet mode" in which the user interface processor 330 of the receiver 200 temporarily reduces the intensity of light from a display, such as an OLED display, of the receiver 200. During the RF packet reception, the light level of the display is reduced for a short period of time which significantly reduces the noise caused by the display and improves RF performance. This reduction in light is virtually imperceptible to the user due to the very short duration of time in which the light has been reduced. In some embodiments, the duration is about 15 to about 100 milliseconds and occurs once every 60 seconds or at time intervals that are determined based on, for example, expected time windows in which data packets are to be received from the transmitter unit 102.

Figure 7:
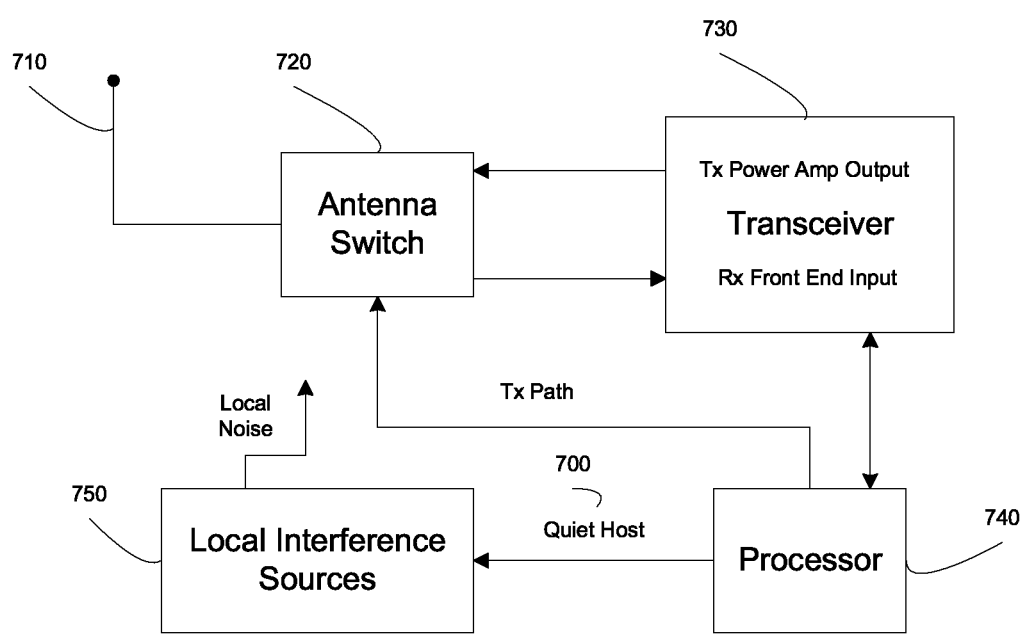
FIG. 7 is a block diagram of a portion of a receiver according to embodiments of the present disclosure.

Referring to FIG. 7, another implementation of noise reduction is to effectively disconnect an antenna of an RF receiver 202 (FIG. 2) of the receiver 200 (FIG. 2) using an antenna switch. As discussed herein, the signal generated by the sensor 101 is received from the transmitter unit 102 by an RF link, approximately once per minute. The RF reception signal path is from the antenna 710, through an antenna switch 720, into a transceiver 730. One purpose of the antenna switch 720 is to enable the antenna 710 to connect and disconnect to either the transmitter power amplifier or to the receiver 200. In certain embodiments, the antenna 710 is connected to the receiver 200 through the antenna switch 720 so as to enable the signal received from the transmitter unit 102 to be more accurate. A processor 740 (e.g., glucose engine processor 350 (FIG. 3)) of the receiver 200 controls the transceiver 730 and the antenna switch 720 in order to maximize noise reduction as will be described in greater detail below.

In certain embodiments, control of the antenna switch 710 is provided by at least one processor of the receiver 200, such as, for example, the glucose engine processor 350 (FIG. 3) described above. Other circuits on the receiver 200 that perform functions unrelated to data reception from the transmitter unit 102, such as, for example, the user interface processor 330, can generate RF noise that interferes with the signal. This circuitry is represented as local interference sources 750 in the block diagram.

In certain embodiments, the receiver 200 is sensitive to on channel signals at very low levels (e.g., about −110 dBm). However, this signal is desensitized by stronger signals such as, the local interference sources 750, even though the local interference sources 750 may not be on the same channel. As the local interference sources 750 are in close proximity to the antenna 710, the local interference sources 750 desensitize the RF receiver 202 and may corrupt the data received from the transmitter unit 102 or cause the data to be inaccurate.

Figure 8:
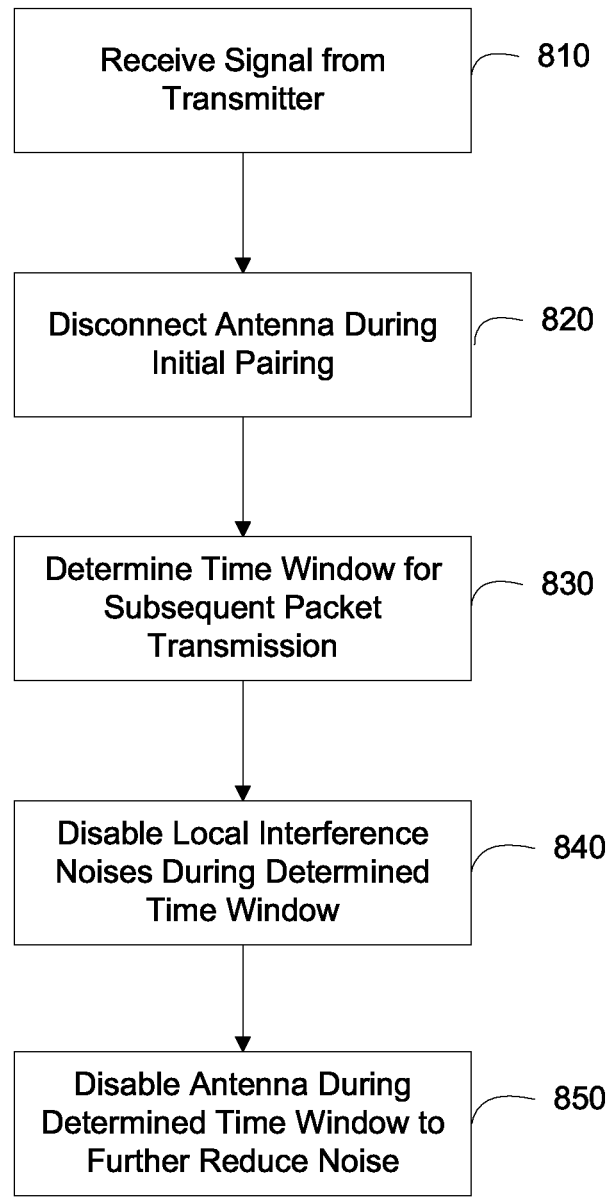
FIG. 8 is a flow chart illustrating a method for reducing noise according to embodiments of the present disclosure.

FIG. 8 illustrates a method 800 for reducing noise according to embodiments of the present disclosure. Referring to FIG. 8, in certain embodiments, the method 800 described below may be used with components that were described above with respect to FIG. 7. The routine for reducing noise begins when the receiver, such as, for example, receiver 200 receives a sensor signal from the transmitter, such as, for example, transmitter unit 102 (810). In certain embodiments, the sensor signal is first received during the establishment of a transmission link between the receiver 200 and the transmitter unit 102 or the initial pairing of the receiver 200 and transmitter unit 102. When establishing the transmission link, a processor 740 (FIG. 7) of the receiver 200 activates a transceiver 730 and waits for the data packet to be transmitted from the transmitter unit 102. Typically, the data packet will arrive between 0 and 70 seconds after the transceiver 730 is activated. Although this range is specifically mentioned, it is contemplated that the data packet may arrive outside this time window, such as for example, after 70 seconds. In order to reduce the effects of local interference sources, the antenna switch 720 (FIG. 7) is used to effectively disconnect the antenna (820) from an RF receiver 202 (FIG. 2) of the receiver 200 which in turn reduces the effect of noise on the receiver 200. Because the RF receiver 202 is not using the antenna 710, the signal received from the transmitter unit 102 is attenuated by approximately 20 dB. Although the signal is attenuated by 20 dB, the local noise level is also reduced by 20 dB which prevents the noise from substantially interfering and desensitizing the RF receiver 202 resulting in a more accurate signal. Further, even though the signal is attenuated by 20 dB, the receiver 200 may be in close proximity to the transmitter unit 102 such that the signal attenuation is acceptable. Disconnecting the antenna 710 during the initial pairing not only reduces noise, but also helps establish a communication range between the receiver 200 and the transmitter unit 102 when the antenna 710 is not used.

Once the receiver 200 has received the first data packet and established a range of communication without the antenna 710 being used, the receiver 200 is configured to determine a window of time (830) in which the next data packet will arrive from the transmitter unit 102. In certain embodiments, the window of time is based on predetermined settings (e.g., once per minute). In another embodiment, the window of time may be selected by a user or health care professional. Once the time window is determined, the processor 740 activates the transceiver 730 for a short duration to receive the next data packet based on the determined window of time. During the determined window of time, a processor (e.g., glucose engine processor 350 (FIG. 3)) of the receiver 200 issues a command that causes one or more components (e.g., the local interference sources 750) of the receiver 200 to be deactivated (840) for a short period of time (e.g., 25 Msec) without substantially affecting the other operations of the receiver 200.

In certain embodiments, the processor 740 asserts a quiet host signal 700 during the determined time window to indicate to the rest of the circuitry that it should enter a low power mode. Additionally, if it is determined that the receiver 200 is within range of the transmitter unit 102 such that the antenna 710 is not needed, the processor 740 issues a command to the switch 720 to disable the antenna (850) during the transmission time window. As a result, the noise level is further reduced. In certain embodiments, the range may be a predetermined range based on the strength of the signal being transmitted from the transmitter unit 102 to the receiver 200. In another embodiment, the range is established during the initial pairing of the receiver 200 and the transmitter unit 102 while the antenna 710 of the receiver 200 has been disconnected as was described above. Further description of implementing a quiet mode can be found in, among others, U.S. Patent Publication No. 2009/0076359, now U.S. Pat. No. 7,801,582, the disclosure of which is incorporated herein by reference for all purposes.

In certain embodiments, the quiet mode also refers to cessation of USB communication, such as, for example, communication between the receiver 200 and peripheral device, such as, for example, a remote computer. In one aspect, as will be described in detail below, the quiet mode also refers to the design of quiet mode blockers.

In certain embodiments, the receiver 200 may have several different power modes. Such modes include power saving modes in which the power of external devices such as sound chips and LCD controllers are turned off. In such modes, the power consumption of one or more processors of the receiver is maintained at a minimum level. In certain embodiments, at least one processor, such as, for example, the user interface processor 330 (FIG. 3) of the receiver 200 includes three modes to manage power consumption. In the first mode (e.g., a run mode), all components (e.g., a display, test strip port, flash memory, etc.) controlled by the user interface processor 330 are active. In this mode, power consumption is at a maximum rate. The second mode is a doze mode. In the doze mode, at least one processor of the receiver 200, such as, for example, the user interface processor 330 is essentially deactivated while a second processor, such as, for example, the glucose engine processor 350, enables required peripherals to run (e.g., calibration modules, internal clocks, etc.). In the stop mode, both of the processors of the receiver 200 are shut down and only a real time clock of the receiver 200 is active.

Figure 9:
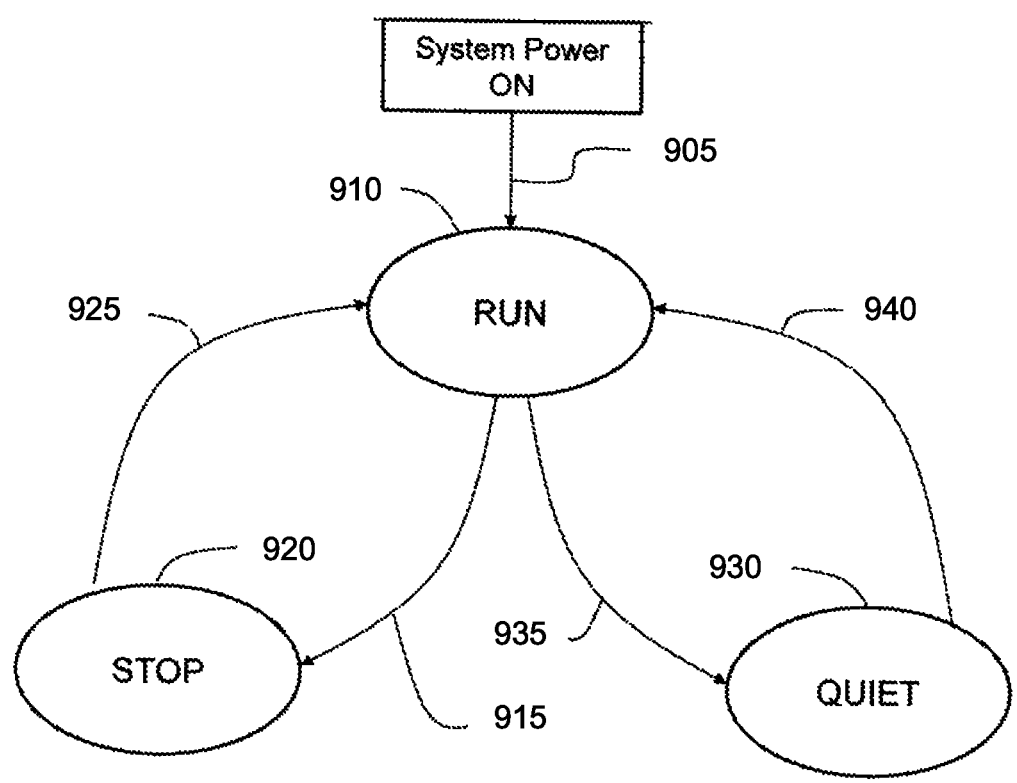
FIG. 9 is a state diagram of a power mode of a receiver according to embodiments of the present disclosure.

FIG. 9 is a state diagram machine that illustrates the various states of power management of a receiver 200 as was described above. These states include a "RUN_MODE" state 910, in which at least one processor of the receiver, such as, for example, a user interface processor 330 (FIG. 3) is in the run mode, referred to above. In the "STOP_MODE" state 920, the user interface processor 330 of the receiver 200 is in the stop mode as was described above. In the "QUIET_MODE" state 930, the timers of the operating system of the receiver 200 and most interrupts are disabled, and one or more processors of the receiver 200 are placed into the stop mode as was described above.

In certain embodiments, to reach the power saving function, the receiver 200 must verify that there are no pending instructions that need to be executed prior to entering the power saving state. As such, blockers are used to indicate if a task or other executable action is in process and has not yet been completed. In certain embodiments, each blocker is a flag. If all the blockers are released (e.g., no flags are set), the receiver 200 enters the play dead mode such as was described above. In certain embodiments, the receiver uses the following exemplary blockers as set forth in Table 3:

TABLE 3

| Blocker | Significance |
| --- | --- |
| "BLOCKER_AUDIO" | Set by audio task to indicate that the sound chip is playing. |

TABLE 3-continued

| Blocker | Significance |
| --- | --- |
| "BLOCKER_BACKLIGHT_PWM" | Set by UI state machine to indicate that the back light is on now. |
| "BLOCKER_WAKE_HOST" | Set by "WAKE_HOST" signal. If this flag is locked, the glucose engine 490 communicates with UI processor 410 and UI cannot get into power saving mode. |
| "BLOCKER_USB_IN" | Set by "USB_IN" signal. If this flag is set, a cable is connected to USB port and ready for connecting to a PC. (Note: In some embodiments, the system uses "BLOCKER_USB_WALLBRICK" signal to indicate if the cable is connected.) |
| "BLOCKER_USB_DATA" | The UI is in the data session with a PC and cannot get into quiet mode or stop mode. |

Referring back to FIG. 9, the transitions between the states, in certain embodiments, are illustrated and summarized in Table 4 below. After power to the receiver 200 is turned on, the receiver 200 enters the "RUN_MODE" state 910 (e.g., transition 905). The receiver 200 transitions from the "RUN_MODE" state 910 to the "STOP_MODE" state 920 (transition 915) when any of the blockers are not set and when a task is not scheduled to run. In entering the "STOP_MODE" state 920, at least one processor of the receiver 200 (e.g., the user interface processor 330) is deactivated and the receiver 200 enters the low power state.

TABLE 4

| Transition | From | To | Conditions | Description |
| --- | --- | --- | --- | --- |
| 915 | RUN | STOP | No blocker set and there is no task scheduled to run | PLLs are turned off and the system enters the low power state. |
| 925 | STOP | RUN | Press of button on receiver or OS timer or USB cable plug-in or Interrupt from glucose engine 490 or Transition of the "QUIET_HOST" signal to "HIGH" or Transition of "HOST_AWAKE" signal to "HIGH" | PLLs are turned on and system resumes normal power state. |
| 935 | RUN | QUIET | No blocker set Transition of "QUIET_HOST" signal to "HIGH" | PLLs are turned off and the OS timers stop. |
| 940 | QUIET | RUN | Transition of "QUIET_HOST" signal to "LOW" | PLLs are turned on and system resumes normal power state. |

In one aspect, the receiver 200 is configured to transition from the "STOP_MODE" state 920 to the "RUN_MODE" state 910 (transition 925) under certain conditions. For example, an interrupt signal can "wake up" the user interface processor 330 after the user interface processor 330 has entered the play dead mode such that the user interface processor returns to normal operation. In certain embodiments, a press of a button on the receiver 200, an OS timer, a USB cable plug-in, and interrupt from the glucose engine processor 350, may wake up the deactivated user interface processor 330 so that receiver 200 runs in normal mode having all functionalities. In addition, the transition of the "QUIET_HOST" signal to "HIGH" by the glucose engine processor 350, or the transition of the "HOST_AWAKE" signal to "HIGH" will also transition the system from "STOP_MODE" state 920 to the "RUN_MODE" state 910.

Referring to the quiet mode 930, when in the quiet mode 930, the phase locked loops of each processor (e.g., the user interface processor 330 and the glucose engine processor 350) are shut down and clock 205 (FIG. 2) is stopped. The receiver 200 enters the "QUIET_MODE" state 930 from the "RUN_MODE" state 910 when triggered by "QUIET_HOST" signal such as described above with reference to FIGS. 7 and 8. For example, the receiver 200 could transition to the "QUIET_MODE" state 930, if and only if, the glucose engine processor 350 raises the "QUIET_HOST" signal (transition 935). The glucose engine processor 350 raises the "QUIET_HOST" signal just prior to reception of the RF packet from the transmitter unit 102, for example, once about every 50-70 seconds. In some embodiments, transmission occurs once about every 60 seconds±500 Msec. Once the receiver 200 has entered the quite mode 930, this mode will persist for a predetermined amount of time (e.g., about 100 Msec). When in the "QUIET_MODE" state 930, the falling edge of the "QUIET_HOST" transitions the receiver 200 out of the "QUIET_MODE" state 930 to the "RUN_MODE" state 910 (transition 940).

In certain embodiments, additional considerations are provided prior to the receiver entering the quiet mode. For example, if the system detects a USB connection when the system is in "QUIET_MODE" state 930, there will be no USB interrupt because the USB is disabled in quiet mode. If the user interface detects a "QUIET_HOST" rising edge during uploading of data to a PC through the USB port, this request from glucose engine processor 350 to quiet the system will be ignored.

There are occasions that continuous communications between the receiver 200 and an external device (e.g., a remote computer) are required for an extended period (e.g., for debugging, product engineering, hardware verification and validation, historical data upload, etc.). During such extended communications, it may be desirable to block the quiet mode entirely. Once the quiet mode is deactivated, communication between the remote computer and the receiver may occur. In certain embodiments, the communication link between the remote computer and receiver only occurs when data packets are not being received by the receiver. At the end of the period of time between packets, the PC application closes the communication link and waits for a signal which indicates that the packet transmission has been completed. In some embodiments, this process will continue as long as the PC application wants to communicate with the device. This technique may avoid the dangling and hanging of the PC application as a result of the receiver going to the quiet mode and shutting down the USB clock before the PC application closes the USB port.

In yet another embodiment, noise reduction techniques are also employed by placement of the antenna in relation to the noise generating circuits. In such embodiments, the antenna may be placed in an area so as to isolate the antenna from the noise source by being as far as physically possible from the noise source. Conversely, it is also contemplated that noise sources may be placed as far as possible from the antenna. Additional design features may be included to increase the isolation, such as ground planes, metal shields, and slots cut in the printed circuit board.

Additionally, it is contemplated that the antenna may be placed to improve signal strength by minimizing obstacles between the signal and antenna. Such considerations include hand placement positions when a user is holding the device as the user's hand may block the signal. Accordingly, the antenna may be placed on an outside edge that will not be covered by the hand of the user.

In the manner described above, an analyte monitoring device, such as, for example, a receiver, may be configured to enter an operating mode (e.g., a power conservation mode) in which certain functionalities and/or components of the analyte monitoring device are selectively disabled. In certain embodiments, this operating mode is entered when the remaining power of a power source of the analyte monitoring device has reached a predetermined minimum threshold level. In certain embodiments, the functionalities and/or components that are disabled are those components and/or functionalities that require the most battery power. Thus, disabling the components and/or functionalities that consume the most power may prolong the time before the analyte monitoring system shuts down due to lack of power which may result in the loss of data. Other conditions that may prompt the analyte monitoring device to enter the operating mode disclosed herein may include low or high operating temperatures of the analyte monitoring device that may cause data corruption or erroneous behavior if the analyte monitoring device were to continue operating under such conditions.

In certain embodiments of the present disclosure, a method is described in which one or more components of the analyte monitoring device are selectively deactivated during a time window in which the analyte monitoring device is to receive and/or transmit data. Because the one or more components are deactivated, the noise generated by those components is reduced which results in an enhanced and more accurate signal.

Certain aspects of the present disclosure may include determining a temperature level of a power source of an analyte monitoring device, determining a level of power remaining in the power source of the analyte monitoring device, and selectively deactivating at least one component of the analyte monitoring device when at least one of the temperature levels of the power source reaches a predetermined temperature threshold or when the level of power remaining in the power source reaches a predetermined power threshold.

In certain embodiments, the at least one component may be a display.

In certain embodiments, the display may be an organic light emitting diode (OLED) display.

In certain embodiments, the at least one component may be a test strip interface.

In certain embodiments, the at least one component may be a memory device.

In certain embodiments, the memory device may be a flash memory device.

In certain embodiments, the predetermined temperature threshold may be about zero degrees Celsius.

In certain embodiments, the predetermined temperature threshold may be about negative five degrees Celsius.

In certain embodiments, the predetermined power threshold may be about 3.6V.

In certain embodiments, the predetermined power threshold may be about 3.7V.

In certain embodiments, selectively deactivating the at least one component may comprise determining an amount of power needed by the at least one component and deactivating the at least one component when the determined amount of power exceeds a threshold level.

In other certain aspects of the present disclosure, an apparatus may include one or more processors, and a memory operatively coupled to the one or more processors, the memory for storing instructions which, when executed by the one or more processors, causes the one or more processors to determine a temperature level of a power source of the apparatus, determine a level of power remaining in the power source of the apparatus, and selectively deactivate at least one component of the apparatus when at least one of the temperature level of the power source reaches a predetermined temperature threshold or when the level of power remaining in the power source reaches a predetermined power threshold.

Other certain aspects of the present disclosure may include providing a receiving unit comprising a radio frequency (RF) receiver, receiving a signal relating to an analyte concentration of a patient, determining a time window for receiving a subsequent signal corresponding to additional analyte concentrations of the patient, and selectively deactivating at least one of an antenna of the receiving unit or at least one component of the receiving unit during the determined time window.

In certain embodiments, the antenna may be deactivated using a switch.

Certain embodiments may include determining a transmission range between the receiving unit and the transmitter.

Certain embodiments may include deactivating the antenna when the determined transmission range is within a predetermined transmission range threshold.

In certain embodiments, the transmission range may be based on the strength of the signal.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. A method comprising:
   determining, by a processor of an analyte monitoring device, a temperature level of a power source of the analyte monitoring device;
   determining, by the processor, whether to cause the analyte monitoring device to enter a power saving mode in which an operation of at least one component of the analyte monitoring device is suspended based on: the temperature level of the power source and whether one or more executable actions are in process;
   determining, by the processor, whether the one or more executable actions are in process based on one or more blocker flags, wherein each respective blocker flag of the one or more blocker flags is indicative of whether a respective executable action of the one or more executable actions is in process; and
   causing, by the processor, the analyte monitoring device to enter the power saving mode based on: the temperature level of the power source and when the one or more executable actions are determined not to be in process based on the one or more blocker flags.

2. The method of claim 1, wherein the at least one component is a display.

3. The method of claim 2, wherein the display is an organic light emitting diode (OLED) display.

4. The method of claim 1, wherein the at least one component includes a test strip interface.

5. The method of claim 1, wherein the at least one component includes a data storage device.

6. The method of claim 1, wherein causing, by the processor, the analyte monitoring device to enter the power saving mode based on the temperature level of the power source comprises:
   causing, by the processor, the analyte monitoring device to enter the power saving mode based on the temperature level being approximately zero degrees Celsius.

7. The method of claim 1, wherein causing, by the processor, the analyte monitoring device to enter the power saving mode based on the temperature level of the power source comprises:
   causing, by the processor, the analyte monitoring device to enter the power saving mode based on the temperature level being approximately negative five degrees Celsius.

8. The method of claim 1, further comprising:
   determining a level of power remaining in the power source of the analyte monitoring device, wherein causing, by the processor, the analyte monitoring device to enter the power saving mode comprises causing, by the processor, the analyte monitoring device to enter the power saving mode based on the level of power remaining in the power source.

9. The method of claim 1, further comprising:
   determining an amount of power needed by the at least one component, wherein causing, by the processor, the analyte monitoring device to enter the power saving mode comprises causing, by the processor, the analyte monitoring device to enter the power saving mode based on the amount of power needed by the at least one component.

10. The method of claim 1, wherein causing, by the processor, the analyte monitoring device to enter the power saving mode comprises causing, by the processor, the analyte monitoring device to enter the power saving mode from a non-power saving mode.

11. The method of claim 10, further comprising:
    maintaining, by the processor while the analyte monitoring device is operating in the power saving mode, a set of components to keep data of the analyte monitoring device updated and current.

12. The method of claim 11, wherein the set of components maintained by the processor include components for at least one of:
    maintaining data corresponding to sensor life,
    operations for calibration, or
    timing of receipt of data packets.

13. The method of claim 1, further comprising:
    determining a minimum voltage associated with the temperature level of the power source, wherein causing, by the processor, the analyte monitoring device to enter the power saving mode comprises causing, by the processor, the analyte monitoring device to enter the power saving mode when the processor determines that the voltage of the power source is less than the minimum voltage associated with the temperature level of the power source.

14. The method of claim 13, wherein the minimum voltage is customizable by a user.

15. The method of claim 11, wherein the data of the analyte monitoring device corresponds to continuously sampled analyte level.

16. The method of claim 1, wherein the at least one component comprises a component configured to perform at least one of:
- write data to memory,
- output an alarm,
- output a notification,
- display data, or
- communicate commands to a remotely controlled device.

* * * * *